US008545837B2

(12) United States Patent
Zhu et al.

(10) Patent No.: US 8,545,837 B2
(45) Date of Patent: *Oct. 1, 2013

(54) METHODS AND COMPOSITIONS FOR CNS DELIVERY OF IDURONATE-2-SULFATASE

(75) Inventors: Gaozhong Zhu, Weston, MA (US); Kris Lowe, Boston, MA (US); Zahra Shahrokh, Weston, MA (US); James Christian, Grafton, MA (US); Richard Fahmer, Boxford, MA (US); Jing Pan, Boxborough, MA (US); Teresa Leah Wright, Lexington, MA (US); Pericles Calias, Melrose, MA (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/168,966

(22) Filed: Jun. 25, 2011

(65) Prior Publication Data

US 2011/0318323 A1    Dec. 29, 2011

Related U.S. Application Data

(60) Provisional application No. 61/358,857, filed on Jun. 25, 2010, provisional application No. 61/360,786, filed on Jul. 1, 2010, provisional application No. 61/387,862, filed on Sep. 29, 2010, provisional application No. 61/435,710, filed on Jan. 24, 2011, provisional application No. 61/442,115, filed on Feb. 11, 2011, provisional application No. 61/476,210, filed on Apr. 15, 2011, provisional application No. 61/495,268, filed on Jun. 9, 2011.

(51) Int. Cl.
*A61K 38/46* (2006.01)
*A61P 25/00* (2006.01)

(52) U.S. Cl.
USPC .................................................. 424/94.3

(58) Field of Classification Search
None
See application file for complete search history.

(56) References Cited

U.S. PATENT DOCUMENTS

| 6,118,045 A | 9/2000 | Reuser et al. |
| 6,217,552 B1 | 4/2001 | Barbut et al. |
| 6,534,300 B1 | 3/2003 | Canfield |

(Continued)

FOREIGN PATENT DOCUMENTS

| WO | WO 02/087510 | 11/2002 |
| WO | WO 03/032727 | 4/2003 |

(Continued)

OTHER PUBLICATIONS

Clarke, "Idursulfase for the treatment of mucopolysaccharidosis II", Expert Opin. Pharmacother. 9(2): 311-317 (2008).*

(Continued)

*Primary Examiner* — Patricia A Leith
*Assistant Examiner* — Erin M Bowers
(74) *Attorney, Agent, or Firm* — Choate Hall & Stewart, LLP; Fangli Chen; Justin P. Huddleson

(57) ABSTRACT

The present invention provides, among other things, compositions and methods for CNS delivery of lysosomal enzymes for effective treatment of lysosomal storage diseases. In some embodiments, the present invention includes a stable formulation for direct CNS intrathecal administration comprising an iduronate-2-sulfatase (I2S) protein, salt, and a polysorbate surfactant for the treatment of Hunters Syndrome.

30 Claims, 53 Drawing Sheets

(56) References Cited

U.S. PATENT DOCUMENTS

| | | | |
|---|---|---|---|
| 6,537,785 | B1 | 3/2003 | Canfield |
| 7,351,410 | B2 | 4/2008 | van Bree et al. |
| 7,396,811 | B2 | 7/2008 | LeBowitz et al. |
| 7,442,372 | B2 | 10/2008 | Kakkis |
| 7,560,424 | B2 | 7/2009 | LeBowitz et al. |
| 7,629,309 | B2 | 12/2009 | LeBowitz et al. |
| 2002/0052311 | A1 | 5/2002 | Solomon et al. |
| 2002/0099025 | A1 | 7/2002 | Heywood |
| 2003/0072761 | A1 | 4/2003 | LeBowitz et al. |
| 2003/0082176 | A1 | 5/2003 | LeBowitz et al. |
| 2004/0005309 | A1 | 1/2004 | LeBowitz et al. |
| 2004/0006008 | A1 | 1/2004 | LeBowitz et al. |
| 2004/0243058 | A1 | 12/2004 | Barbut et al. |
| 2004/0248262 | A1 | 12/2004 | Koeberl et al. |
| 2005/0048047 | A1* | 3/2005 | Kakkis ................... 424/94.61 |
| 2005/0208090 | A1 | 9/2005 | Keimel et al. |
| 2005/0244400 | A1 | 11/2005 | LeBowitz et al. |
| 2005/0281805 | A1 | 12/2005 | LeBowitz et al. |
| 2006/0029656 | A1 | 2/2006 | O'Donnell et al. |
| 2006/0177433 | A1 | 8/2006 | Treco et al. |
| 2008/0299640 | A1 | 12/2008 | LeBowitz et al. |
| 2009/0017005 | A1 | 1/2009 | Kakkis |
| 2009/0041741 | A1 | 2/2009 | Sly et al. |
| 2009/0130079 | A1 | 5/2009 | Dodge et al. |
| 2009/0191178 | A1 | 7/2009 | Zankel et al. |
| 2009/0291062 | A1 | 11/2009 | Fraunhofer et al. |
| 2009/0297592 | A1 | 12/2009 | Sakuraba et al. |
| 2010/0068195 | A1 | 3/2010 | Vellard et al. |
| 2012/0148558 | A1 | 6/2012 | Kakkis |
| 2012/0213762 | A1 | 8/2012 | LeBowitz et al. |

FOREIGN PATENT DOCUMENTS

| | | |
|---|---|---|
| WO | WO 03/032913 | 4/2003 |
| WO | WO 03/102583 | 12/2003 |
| WO | WO 2005/078077 | 8/2005 |
| WO | WO-2007/141346 A2 | 12/2007 |
| WO | WO 2009/137721 | 11/2009 |
| WO | WO 2011/163647 | 12/2011 |
| WO | WO 2011/163648 | 12/2011 |
| WO | WO 2011/163649 | 12/2011 |
| WO | WO 2011/163650 | 12/2011 |
| WO | WO 2011/163651 | 12/2011 |

OTHER PUBLICATIONS

Phosphate Buffer Calculator, http://www.egr.msu.edu/biofuelcell/tools/phosphate/phosphate.html, Dec. 31, 2000, accessed Aug. 28, 2012.*

Clarke, Expert Opin. Pharmacother. 9(2): 311-317 (2008).*

Kakkis et al., Mol. Genet. Metab. 83: 163-174 (2004).*

Altschul et al., "Basic logic alignment search tool," J. Mol. Biol., 215(3): 403-410, 1990.

Altschul et al., "Gapped BLAST and PSI-BLAST: a new generation of protein database search programs," Nucleic Acids Res. 25: 3389-3402, 1997.

Altschul et al., "Local alignment statistics," 266:460-80, Methods in Enzymology., 1996.

Ammaya et al., "Subcutaneous Reservoir and Pump for Sterile Access to Ventricular Cerebrospinal Fluid," Lancet 2(7315): 983-984, 1963.

Baskin, G. et al., "Genetic galactocerebrosidase deficiency (globoid cell leukodystrophy, Krabbe disease) in rhesus monkeys (Macaca mulatta)," Lab Anim. Sci., 48(5): 476-482, 1998.

Baum, H. et al., "The assay of arylsulphatases A and B in human urine," Clin Chim Acta. 4(3): 453-455, 1959.

Begley et al., "Lysosomal storage diseases and the blood-brain barrier," Curr Pharm Des 14(16): 1566-1580, 2008.

Belichenko et al., Penetration, diffusion, and uptake of recombinant human alpha-L-iduronidase after intraventricular injection into the rat brain, Mol. Genet. Metab., 86(1-2): 141-149, 2005.

Beniaminovitz et al., "Prevention of rejection in cardiac transplantation by blockage of the interleukin-2 receptor with a monoclonal antibody," N. Engl. J. Med. 342(9): 613-619, 2000.

Berard et al., "A review of interleukin-2 receptor antagonists in solid organ transplantation," Pharmacotherapy 19(10): 1127-1137, 1999.

Bielicki et al., "Recombinant human sulphamidase: expression, amplification, purification and characterization," Journal of Biochemistry, 329(Pt 1): 145-150, 1998.

Biswas S. et al., "Substrate reduction intervention by L-cycloserine in twitcher mice (globoid cell leukodystrophy) on a B6; CAST/Ei background," Neurosci. Lett., 347(1): 33-36, 2003.

Blasberg, R.G. et al., "Intrathecal chemotherapy: brain tissue profiles after ventriculocisternal perfusion," J Pharmacol Exp Ther. 195(1): 73-83, 1975.

Bobo et al., "Convection-enhanced delivery of macromolecules in the brain," Proc. Natl. Acad. Sci. U.S.A. 91(6), 2076-2080, 1994.

Bowman, R.H., "Inhibition of citrate metabolism by sodium fluoroacetate in the perfused rat heart and the effect on phosphofructokinase activity and glucose utilization," 93(2): 13C-15C, 1964.

Branco et al., "Selective deletion of antigen-specific, activated T cells by a humanized MAB to CD2 (MEDI-507) is mediated by NK cells," Transplantation 68(10): 1588-1596, 1999.

Butt MT, "Morphologic changes associated with intrathecal catheters for direct delivery to the central nervous system im preclinical studies," Toxicol. Pathol., 39(1): 213-219, 2011.

Cabrera-Salazar, M.A. et al., "Intracerebroventricular delivery of glucocerebrosidase reduces substrates and increases lifespan in a mouse model of neuronopathic Gaucher disease," Exp Neurol. 225(2): 436-444, 2010.

Chirmule et al., "Readministration of adenovirus vector in nonhuman primate lungs by blockage of CD40-CD40 ligand interactions," J. Virol. 74(7): 3345-3352, 2000.

Chiro et al., "Spinal descent of cerebrospinal fluid in man," Neurology 26(1): 1-8, 1976.

Dekaban AS., "Changes in brain weights during the span of human life: relation of brain weights to body heights and body weights," Ann Neurol 4: 345-356, 1978.

Desnick, R.J., "Enzyme replacement and enhancement therapies for lysosomal diseases," J. Inherit. Metab. Dis., 27(3): 385-410, 2004.

Eckhoff et al., "The safety and efficacy of a two-dose daclizumab (zenapax) induction therapy in liver transplant recipients," Transplantation 69(9): 1867-1872, 2000.

Ekberg et al., "Daclizumab prevents acute rejection and improves patient survival post transplantation: 1 year pooled analysis," Transpl. Int. 13(2): 151-159, 2000.

Elaprase (idursulfase), http://www.elaprase.com/pdf/Elaorase_Overview_Sheet110811.pdf, REV 5, 2011.

Fenstermacher et al., "Drug "diffusion" within the brain," Ann NY Acad Sci 531: 29-39, 1988.

Ficko-Blean E, et al., "Structural and mechanistic insight into the basis of mucopolysaccharidosis IIIB," PNAS, 105(18): 6560-6565, 2008.

Fishwild et al., "Differential effects of administration of a human anti-CD4 monoclonal antibody, HM6G, in nonhuman primates," Clin. Immunol. 92(2): 138-152, 1999.

Gaziev et al., "Chronic graft-versus-host disease: is there an alternative to the conventional treatment?," Bone Marrow Transplant, 25(7): 689-696, 2000.

GeneCards, Galactosylceramidase, http://www.genecards.org/cgi-bin/carddisp.pl?gene=GALC&search=Galactocerebrosidase, 2012.

Ghersi-Egea, J.F. et al, "Rapid distribution of intraventricularly administered sucrose into cerebrospinal fluid cisterns via subarachnoid velae in rat," Neuroscience 75(4): 1271-1288, 1996.

Graham et al., "Characteristics of a human cell line transformed by DNA from human adenovirus type 5," J. Gen Virol., 36(1): 59-74, 1977.

Grubb JH et al., "New strategies for enzyme replacement therapy for lysosomal storage diseases," Rejuvenation Research 13(2-3): 229-236, 2010.

Gummert et al., "Newer immunosuppressive drugs: a review," J. Am. Soc. Nephrol, 10(6): 1366-1380, 1999.

Hashimoto R, "N-terminal deletion mutants of insulin-like growth factor-II (IGF-II) show Thr7 and Leu8 important for binding to insulin and IGF-I receptors and Leu8 critical for all IGF-II functions," J Biol Chem., 270(30); 18013-18018, 1995.

Hemsley, Kim M. et al., "Injection of recombinant human sulfamidase into the CSF via the cerebellomedullary cistern in MPS IIIA mice," Mol Genet Metab. 90(3): 313-328, 2007.
Henry ML, "Cyclosporine and tacrolimus (FK506): a comparison of efficacy and safety profiles," Clin. Transplant, 13(3): 209-220, 1999.
Hong et al., "Immunosuppressive agents in organ transplantation: past, present, and future," Semin. Nephrol. 20(2): 108-125, 2000.
Hood RD, Development and Reproductive Toxicology: A practical approach, 276, 2006.
Hoogerbrugge, P.M., et al., "Effect of bone marrow transplantation on enzyme levels and clinical course in the neurologically affected," J. Clin. Invest., 81(6): 1790-1794, 1988.
Hovland DN, et al., "Six-month continuous intraputamenal infusion toxicity study of recombinant methionyl human glial cell line-derived neurotrophic factor (r-metHuGDNF in rhesus monkeys," Toxicol. Pathol., 35(7): 1013-1029, 2007.
Ideguchi et al., "Local adenovirus-mediated CFLA40immunoglobulin expression suppresses the immune responses to adenovirus vectors in the brain," Neuroscience 95(1): 217-226, 2000.
International Search Report for PCT/US11/41922, mailed Feb. 14, 2012.
International Search Report for PCT/US11/41924, mailed Nov. 7, 2011.
International Search Report for PCT/US11/41925, mailed Feb. 14, 2012.
International Search Report for PCT/US11/41927, mailed Mar. 9, 2012.
Ito et al., "Induction of CTL responses by simultaneous administration of liposomal peptide vaccine with anti-CD40 and anti-CTLA-4 mAb," J. Immunol. 164(3): 1230-1235, 2000.
Johanson CE, et al., "Multiplicity of cerebrospinal fluid functions: New challenges in health and disease," Cerebrospinal Fluid Res., 14(5): 10, 2008.
Johnson, K., "Globoid leukodystrophy in the cat," J. Am. Vet. Med. Assoc., 157(12): 2057-2064, 1970.
Joshi S. et al., "Targeting the brain: rationalizing the novel methods of drug delivery to the central nervous system," Neurocrit Care 6(3): 200-212, 2007.
Kobayashi T. et al., "The Twitcher mouse: an enzymatically authentic model of human globoid cell leukodystrophy (Krabbe disease)," Brain Res., 202(2): 479-483, 1980.
Krewson, CE et al., "Distribution of nerve growth factor following direct delivery to brain interstitium," Brain Res. 680(1-2): 196-206, 1995.
Kurlberg et al., "Blockage of the B7-CD28 pathway by CTLA4-Ig counteracts rejection and prolongs survival in small bowel transplantation," Scand. J. Immunol, 51(3): 224-230, 2000.
Lazorthes et al., Advances in Drug Delivery Systems and Application in Neurosurgery, 18: 143-192, 1991.
Lee, et al., "Single-dose intracerebroventricular administration of galactocerebrosidase improves survival in a mouse model of globoid cell leukodystrophy," FASEB Journal, 21(10): 2520-2527, 2007.
LeVine S. et al., "L-cycloserine slows the clinical and pathological course in mice with globoid cell leukodystrophy (twitcher mice)," J. Neurosci. Res., 60(2): 231-236, 2000.
Li HH, et al., "Mouse model of Sanfilippo syndrome type B produced by targeted disruption of the gene encoding alpha-N-acetylglucosaminidase," PNAS 96(25): 14505-14510, 1999.
Li, et al., "Attenuated plasticity in neurons and astrocytes in the mouse model of Sanfilippo syndrome type B," J Neurosci Res, 69(1): 30-8, 2002.
Lin, D., et al., "Central nervous system-directed AAV2/5-mediated gene therapy synergizes with bone marrow transplantation in the murine model of globoid-cell leukodystrophy," Mol. Ther., 15(1): 44-52, 2007.
Luca, Tonia, "Axons mediate the distribution of arylsulfatase A within the mouse hippocampus upon gene delivery," Mol Ther. 12(4): 669-679, 2005.
Marinova-Mutafchieva et al., "A comparative study into the mechanisms of action of anti-tumor necrosis factor alpha, anti-CD4, and combined anti-tumor necrosis factor alpha/anti-CD4 treatment in early collagen-induced arthritis," Arthritis Rheum 43: 638-644, 2000.
Mather et al., "Culture of testicular cells in hormone-supplemented serum-free medium," Ann N.Y. Acad. Sci., 383: 44-68, 1982.
Mather, "Establishment and characterization of two distinct mouse testicular epithelial cell lines," Biol. Reprod., 23: 243-251, 1980.
Matheus, MG et al., "Brain MRI findings in patients with mucopolysaccharidosis types I and Ii and mild clinical presentation," Neuroradiology 46(8): 666-672, 2004.
Meikle et al., "Diagnosis of lysosomal storage disorders: evaluation of lysosome-associated membrane protein LAMP-1 as a diagnostic marker," Clin Chem., 43(8 Pt 1): 1325-1335, 1997.
Middaugh et al., "Determination of the apparent thermodynamic activities of saturated protein solutions," J. Biol. Chem. 254(2): 367-370, 1979.
Moder, KG., "New medications for use in patients with rheumatoid arthritis," Ann. Allergy Asthma Immunol. 84(3): 280-284, 2000.
Nagaraja, TN et al., "In normal rat, intraventricularly administered insulin-like growth factor-1 is rapidly cleared from CSF with limited distribution into brain," Cerebrospinal Fluid Res. 2: 1-15, 2005.
Nail S.L. et al., "Fundamentals of freeze-drying, in Development and manufacture of protein pharmaceuticals," Nail S.L. editor New York: Kluwer Academic/Plenum Publishers, 281-353, 2002.
Neufeld EF, Muenzer J., "The mucopolysaccharidoses," In: Scriver CR, Beaudet AI, Sly WS, et al, eds. The Metabolic and Molecular Bases of Inherited Disease. www.ommbid.com 8th ed. New York, NY: McGraw-Hill; 2001:3421-3452.
Neufeld, E.F., Enzyme Replacement therapy. Lysosomal disorders of the Brain, ed. F.M.a.W. Platt, S.V. 2004: Oxford University Press: 327-338, 2004.
Nevins, TE., "Overview of new immunosuppressive therapies," Curr. Opin. Pediatr. 12(2): 146-150, 2000.
Nguyen et al., "Convective distribution of macromolecules in the primate brain demonstrated using computerized tomography and magnetic resonance imaging," J. Neurosurg. 98(3), 584-590, 2003.
Ohmi, et al., "Activated microglia in cortex of mouse models of mucopolysaccharidoses I and IIIB," Proc Natl Acad Sci, 100(4): 1902-7, 2002.
Ommaya et al., "Implantable devices for chronic access and drug delivery to the central nervous system," Cancer Drug Delivery, 1(2): 169-179, 1984.
Pardridge WM., "Drug transport in brain via the cerebrospinal fluid," Fluids Barriers CNS, 8(1): 7, 2011.
Passini, MA et al., "Distribution of a lysosomal enzyme in the adult brain by axonal transport and by cells of the rostral migratory stream," J Neurosci 22(15): 6437-6446, 2002.
Penn, RD et al., "Intrathecal ciliary neurotrophic factor delivery for treatment of amyotrophic lateral sclerosis (phase I trial)," Neurosurgery 40(1): 94-99, 1997.
Ponce RP, et al., "Immunogenicity of biologically-derived therapeutics: assessment and interpretation of nonclinical safety studies," Regul. Toxicol. Pharmacol., 54(2): 164-182, 2009.
Ponticelli et al., "Promising new agents in the prevention of transplant rejection," Drugs R.D. 1(1), 55-60, 1999.
Potter et al., "Review—the use of immunosuppressive agents to prevent neutralizing antibodies against a transgene product," Ann. N.Y. Acad. Sci. 875: 159-174, 1999.
Pritchard, D. et al., "Globoid cell leucodystrophy in polled Dorset sheet," Vet. Pathol., 17(4): 399-405, 1980.
Przepiorka et al., "A phase II study of BTI-322, a monoclonal anti-CD2 antibody, for treatment of steroid-resistant acute graft-versus-host disease," Blood 92(11): 4066-4071, 1998.
Qi et al., "Effect of tacrolimus (FK506) and sirolimus (rapamycin) mono- and combination therapy in prolongation of renal allograft survival in the monkey," Transplantation 69(7), 1275-1283, 2000.
Rieselbach RE et al., "Subarachnoid distribution of drugs after lumbar injection," N Engl J Med. 267(25): 1273-1278, 1962.
Saves, et al., "Intracerebral injection of sulfamidase delays neuropathology in murine MPS-IIIA," Mol Genet Metab., 82(4): 273-285, 2004.

Shahrokh et al., "Intrathecal delivery of protein therapeutics to treat genetic diseases involving the CNS, in: Injectable Drug Delivery 2010: Formulations Focus," ONdrugDelivery, pp. 16-20, 2010.

Simard JM et al., "Brain oedema in focal ischaemia: molecular pathophysiology and theoretical implications," Lancet Neurol. 6(3): 258-268, 2007.

Slavik et al., "CD28/CTLA-4 and CD80/CD86 families: signaling and function," Immunol Res. 19(1): 1-24, 1999.

Stamatovic SM, et al., "Brain endothelial cell-cell junctions: how to "open" the blood brain barrier," Curr. Neuropharmacol., 6(3): 179-192, 2008.

Stroobants S. et al., "Intracerebroventricular enzyme infusion corrects central nervous system pathology and dysfunction in a mouse model of metachromatic leukodystrophy," Hum Mol Genet. 20(14): 2760-2769, 2011.

Sturk, et al., "Combined Intracerebroventricular Intraperitoneal Enzyme Replacement Therapy Improves Survival and Reduces Brain Psychosine in a Mouse Model of Krabbe Disease," European Task Force on Brain and Neurogenerative Lysosomal Storage Diseases, http://www.brains4brain.eu/assets/files/abstract-francoforte-2009.pdf p. 42, 2009.

Tang, X. et al., "Design of freeze-drying processes for pharmaceuticals: Practical advice," Pharm. Res., 21(2): 191-200, 2004.

Toyoshima, E. et al., "Nerve conduction studies in the Twitcher mouse (murine globoid cell leukodystrophy)," J. Neurol. Sci., 74(2-3): 307-318, 1986.

Urlaub and Chasin, "Isolation of Chinese hamster cell mutants deficient in dihydrofolate reductase activity," Proc. Natl. Acad. Sci. USA, 77(7): 4216-4220, 1980.

Vedolin, L. et al., "Correlation of MR imaging and MR spectroscopy findings with cognitive impairment in mucopolysaccharidosis II," AJNR Am J Neuroradial 28(6): 1029-1033, 2007.

Vite, Charles H. et al., "Biodistribution and pharmacodynamics of recombinant human alpha-L-iduronidase (rhIDU) in mucopolysaccharidosis type I-affected cats following multiple intrathecal administrations," Mol Genet Metab 103(3): 268-274, 2011.

Vogler, C. et al., "Overcoming the blood-brain barrier with high-dose enzyme replacement therapy in murine mucopolysaccharidosis VII," Proc Natl Acad Sci USA 102(41): 14777-14782, 2005.

Waheed, A et al., "Purification of mammalian arylsulfatase A enzymes by subunit affinity chromatography," Int J Pept Protein Res., 26(4): 362-372, 1985.

Walkley, "Cell Pathology of lysosomal storage disorders," Brain Pathol., 8, 175-93, 1998.

Wang et al., "Lyophilization and development of solid protein pharmaceuticals," Int. J. Pharm., 203(1-2): 1-60, 2000.

Wang et al., "Treatment reduces or stabilizes brain imaging abnormalities in patients with MPS I and II," Molecular Genetics and Metabolism, 98(4): 406-11, 2009.

Watson et al., "Intrathecal administration of AAV vectors for the treatment of lysosomal storage in the brains of MPS I mice," Gene Ther., 13(11): 917-925, 2006.

Wenger, D.A. et al., Galactosylceramide Lipidosis: Globoid Cell Leukodystrophy (Krabbe Disease), in the Metabolic and Molecular Bases of Inherited Disease, C.R. Scriver, Beaudet, A., Sly, W.S. and Valle, D. Editor 2001 McGraw-Hill, 3669-3687, 2001.

Wenger, D.A., "Murine, canine and non-human primate models of Krabbe disease," Mol. Med. Today, 6(11): 449-451, 2000.

Williams N.A. et al., "The lyophilization of pharmaceuticals; A literature review." J. Parenter Sci. Technol., 38(2): 48-59, 1984.

Wiseman et al., "Daclizumab: a review of its use in the prevention of acute rejection in renal transplant recipients," Drugs 58(6): 1029-1042, 1999.

Written Opinion for PCT/US11/41922, mailed Feb. 14, 2012.
Written Opinion for PCT/US11/41924, mailed Nov. 7, 2011.
Written Opinion for PCT/US11/41925, mailed Feb. 14, 2012.
Written Opinion for PCT/US11/41927, mailed Mar. 9, 2012.

Yan Q et al., "Distribution of intracerebral ventricularly administered neurotrophins in rat brain and its correlation with trk receptor expression," Exp Neurol. 127(1): 23-36, 1994.

Yeager A. et al., "Prolonged survival and remyelination after hematopoietic cell transplantation in the twitcher mouse," Science, 225(4666): 1052-1054, 1984.

Sjoberg, M. et al., Long-term Intrathecal Morphine and Bupivacaine in Patients with Refractory Cancer Pain, Anesthesiology, 80:284-297 (1994).

Schlessingerman, A., Mass of an Adult, obtained from hypertextbook.com/facts/2003/AlexSchlessingerman.shtml, 2003, 2 pages.

Champion K. J. et al., Identification and characterization of a novel homozygous deletion in the x-N-acetylglucosaminidase gene in a patient with Sanfilippo type B syndrome (mucopolysaccharidosis IIIB), Molecular Genetics and Metabolism, 100: 51-56 (2010).

Cressent, A. et al., Improved Behavior and Neuropathology in the Mouse Model of Sanfilippo Type IIIB Disease after Adeno-Associated Virus-Mediated Gene Transfer in the Striatum, The Journal of Neuroscience, 24(45): 10229-10239 (2004).

Tippin, B. et al., Insulin-like Growth Factor-2 Peptide Fusion Enables Uptake and Lysosomal Delivery of N-Acetylglucosamindidase to Mucopolysaccharidosis IIIB Fibrboblasts, MPS Scientific Program: Plenary Papers, entire document: p. 100 (Jun. 26, 2010).

International Search Report for PCT/US2011/041928, 4 pages (Sep. 26, 2012).

Written Opinion for PCT/US2011/041928, 13 pages (Sep. 26, 2012).

* cited by examiner

Vehicle cerebral cortex 3 dose I2S cerebral cortex 3 dose I2S cerebellar cortex 12S positive neurons, glial cells, and meningeal cells were found within the layer I (Panel A), layer III (Panel B) and layer VI (Panel C) of the brain. This animal was in the 30 mg dose group.
(40X magnification)

30 mg dose group. Original magnification = 40X.

SEQUENCE LISTING

```
<160> NUMBER OF SEQ ID NOS: 2

<210> SEQ ID NO 1
<211> LENGTH: 525
<212> TYPE: PRT
<213> ORGANISM: Homo sapiens

<400> SEQUENCE: 1

Ser Glu Thr Gln Ala Asn Ser Thr Thr Asp Ala Leu Asn Val Leu Leu
1               5                   10                  15
```

```
Ile Ile Val Asp Asp Leu Arg Pro Ser Leu Gly Cys Tyr Gly Asp Lys
             20                  25                  30

Leu Val Arg Ser Pro Asn Ile Asp Gln Leu Ala Ser His Ser Leu Leu
         35                  40                  45

Phe Gln Asn Ala Phe Ala Gln Gln Ala Val Cys Ala Pro Ser Arg Val
50                      55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                 85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
            115                 120                 125

Ser Phe Pro Pro Tyr His Pro Ser Ser Glu Lys Tyr Glu Asn Thr Lys
        130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
            245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
            325                 330                 335

Tyr Val Pro Gly Arg Thr Ala Ser Leu Pro Glu Ala Gly Glu Lys Leu
        340                 345                 350

Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
        435                 440                 445
```

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
                500                 505                 510

Asp Ser Gln Gly Gly Asp Leu Phe Gln Leu Leu Met Pro
            515                 520                 525

<210> SEQ ID NO 2
<211> LENGTH: 550
<212> TYPE: PRT
<213> ORGANISM: Homo sapiens

<400> SEQUENCE: 2

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
                20                  25                  30

Thr Thr Asp Ala Leu Asn Val Leu Leu Ile Ile Val Asp Asp Leu Arg
            35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
    210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
    290                 295                 300

```
Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
                340                 345                 350

Val Ala Thr His Val Pro Leu Ile Phe Tyr Val Pro Gly Arg Thr Ala
            355                 360                 365

Ser Leu Pro Glu Ala Gly Glu Lys Leu Phe Pro Tyr Leu Asp Pro Phe
        370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
                420                 425                 430

Arg Glu Gly Lys Asn Leu Leu Lys His Phe Arg Phe Arg Asp Leu Glu
            435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
                500                 505                 510

Asn Phe Ser Asp Ile His Ala Gly Glu Leu Tyr Phe Val Asp Ser Asp
            515                 520                 525

Pro Leu Gln Asp His Asn Met Tyr Asn Asp Ser Gln Gly Gly Asp Leu
    530                 535                 540

Phe Gln Leu Leu Met Pro
545             550
```

METHODS AND COMPOSITIONS FOR CNS DELIVERY OF IDURONATE-2-SULFATASE

CROSS REFERENCE TO RELATED APPLICATIONS

This application claims priority to U.S. Provisional Patent Application Ser. Nos. 61/358,857 filed Jun. 25, 2010; 61/360,786, filed Jul. 1, 2010; 61/387,862, filed Sep. 29, 2010; 61/435,710, filed Jan. 24, 2011; 61/442,115, filed Feb. 11, 2011; 61/476,210, filed Apr. 15, 2011; and 61/495,268 filed on Jun. 9, 2011; the entirety of each of which is hereby incorporated by reference.

SEQUENCE LISTING

In accordance with 37 CFR 1.52(e)(5), a Sequence Listing in the form of a text file (entitled "SequenceListing.txt," created on Aug. 3, 2011, and 10 kilobytes in size) is incorporated herein by reference in its entirety.

This application relates to US applications entitled "CNS Delivery of Therapeutic Agents," filed on even date; "Methods and Compositions for CNS Delivery of Heparan N-Sulfatase," filed on even date; "Methods and Compositions for CNS Delivery of Arylsulfatase A," filed on even date; "Methods and Compositions for CNS Delivery of β-Galactocerebrosidase," filed on even date; "Treatment of Sanfilippo Syndrome Type B," filed on even date; the entirety of each of which is hereby incorporated by reference.

BACKGROUND

Enzyme replacement therapy (ERT) involves the systemic administration of natural or recombinantly-derived proteins and/or enzymes to a subject. Approved therapies are typically administered to subjects intravenously and are generally effective in treating the somatic symptoms of the underlying enzyme deficiency. As a result of the limited distribution of the intravenously administered protein and/or enzyme into the cells and tissues of the central nervous system (CNS), the treatment of diseases having a CNS etiology has been especially challenging because the intravenously administered proteins and/or enzymes do not adequately cross the blood-brain barrier (BBB).

The blood-brain barrier (BBB) is a structural system comprised of endothelial cells that functions to protect the central nervous system (CNS) from deleterious substances in the blood stream, such as bacteria, macromolecules (e.g., proteins) and other hydrophilic molecules, by limiting the diffusion of such substances across the BBB and into the underlying cerebrospinal fluid (CSF) and CNS.

There are several ways of circumventing the BBB to enhance brain delivery of a therapeutic agent including direct intra-cranial injection, transient permeabilization of the BBB, and modification of the active agent to alter tissue distribution. Direct injection of a therapeutic agent into brain tissue bypasses the vasculature completely, but suffers primarily from the risk of complications (infection, tissue damage, immune responsive) incurred by intra-cranial injections and poor diffusion of the active agent from the site of administration. To date, direct administration of proteins into the brain substance has not achieved significant therapeutic effect due to diffusion barriers and the limited volume of therapeutic that can be administered. Convection-assisted diffusion has been studied via catheters placed in the brain parenchyma using slow, long-term infusions (Bobo, et al., Proc. Natl. Acad. Sci. U.S.A. 91, 2076-2080 (1994); Nguyen, et al. J. Neurosurg. 98, 584-590 (2003)), but no approved therapies currently use this approach for long-term therapy. In addition, the placement of intracerebral catheters is very invasive and less desirable as a clinical alternative.

Intrathecal (IT) injection, or the administration of proteins to the cerebrospinal fluid (CSF), has also been attempted but has not yet yielded therapeutic success. A major challenge in this treatment has been the tendency of the active agent to bind the ependymal lining of the ventricle very tightly which prevented subsequent diffusion. Currently, there are no approved products for the treatment of brain genetic disease by administration directly to the CSF.

In fact, many have believed that the barrier to diffusion at the brain's surface, as well as the lack of effective and convenient delivery methods, were too great an obstacle to achieve adequate therapeutic effect in the brain for any disease.

Many lysosomal storage disorders affect the nervous system and thus demonstrate unique challenges in treating these diseases with traditional therapies. There is often a large build-up of glycosaminoglycans (GAGs) in neurons and meninges of affected individuals, leading to various forms of CNS symptoms. To date, no CNS symptoms resulting from a lysosomal disorder has successfully been treated by any means available.

Thus, there remains a great need to effectively deliver therapeutic agents to the brain. More particularly, there is a great need for more effective delivery of active agents to the central nervous system for the treatment of lysosomal storage disorders.

SUMMARY OF THE INVENTION

The present invention provides an effective and less invasive approach for direct delivery of therapeutic agents to the central nervous system (CNS). The present invention is, in part, based on the unexpected discovery that a replacement enzyme (e.g., iduronate-2-sulfatase (I2S)) for a lysosomal storage disease (e.g., Hunters Syndrome) can be directly introduced into the cerebrospinal fluid (CSF) of a subject in need of treatment at a high concentration (e.g., greater than about 3 mg/ml, 4 mg/ml, 5 mg/ml, 10 mg/ml or more) such that the enzyme effectively and extensively diffuses across various surfaces and penetrates various regions across the brain, including deep brain regions. More surprisingly, the present inventors have demonstrated that such high protein concentration delivery can be achieved using simple saline or buffer-based formulations and without inducing substantial adverse effects, such as severe immune response, in the subject. Therefore, the present invention provides a highly efficient, clinically desirable and patient-friendly approach for direct CNS delivery for the treatment of various diseases and disorders that have CNS components, in particular, lysosomal storage diseases. The present invention represents a significant advancement in the field of CNS targeting and enzyme replacement therapy.

As described in detail below, the present inventors have successfully developed stable formulations for effective intrathecal (IT) administration of an iduronate-2-sulfatase (I2S) protein. It is contemplated, however, that various stable formulations described herein are generally suitable for CNS delivery of therapeutic agents, including various other lysosomal enzymes. Indeed, stable formulations according to the present invention can be used for CNS delivery via various techniques and routes including, but not limited to, intraparenchymal, intracerebral, intravetricular cerebral (ICV), intrathecal (e.g., IT-Lumbar, IT-cisterna magna) administrations and any other techniques and routes for injection directly or indirectly to the CNS and/or CSF.

It is also contemplated that various stable formulations described herein are generally suitable for CNS delivery of other therapeutic agents, such as therapeutic proteins including various replacement enzymes for lysosomal storage diseases. In some embodiments, a replacement enzyme can be a synthetic, recombinant, gene-activated or natural enzyme.

In various embodiments, the present invention includes a stable formulation for direct CNS intrathecal administration comprising an iduronate-2-sulfatase (I2S) protein, salt, and a polysorbate surfactant. In some embodiments, the I2S protein is present at a concentration ranging from approximately 1-300 mg/ml (e.g., 1-250 mg/ml, 1-200 mg/ml, 1-150 mg/ml, 1-100 mg/ml, or 1-50 mg/ml). In some embodiments, the I2S protein is present at or up to a concentration selected from 2 mg/ml, 3 mg/ml, 4 mg/ml, 5 mg/ml, 10 mg/ml, 15 mg/ml, 20 mg/ml, 25 mg/ml, 30 mg/ml, 35 mg/ml, 40 mg/ml, 45 mg/ml, 50 mg/ml, 60 mg/ml, 70 mg/ml, 80 mg/ml, 90 mg/ml, 100 mg/ml, 150 mg/ml, 200 mg/ml, 250 mg/ml, or 300 mg/ml.

In various embodiments, the present invention includes a stable formulation of any of the embodiments described herein, wherein the I2S protein comprises an amino acid sequence of SEQ ID NO:1. In some embodiments, the I2S protein comprises an amino acid sequence at least 60%, 65%, 70%, 75%, 80%, 85%, 90%, 95%, or 98% identical to SEQ ID NO:1. In some embodiments, the stable formulation of any of the embodiments described herein includes a salt. In some embodiments, the salt is NaCl. In some embodiments, the NaCl is present as a concentration ranging from approximately 0-300 mM (e.g., 0-250 mM, 0-200 mM, 0-150 mM, 0-100 mM, 0-75 mM, 0-50 mM, or 0-30 mM). In some embodiments, the NaCl is present at a concentration ranging from approximately 137-154 mM. In some embodiments, the NaCl is present at a concentration of approximately 154 mM.

In various embodiments, the present invention includes a stable formulation of any of the embodiments described herein, wherein the polysorbate surfactant is selected from the group consisting of polysorbate 20, polysorbate 40, polysorbate 60, polysorbate 80 and combination thereof. In some embodiments, the polysorbate surfactant is polysorbate 20. In some embodiments, the polysorbate 20 is present at a concentration ranging approximately 0-0.02%. In some embodiments, the polysorbate 20 is present at a concentration of approximately 0.005%.

In various embodiments, the present invention includes a stable formulation of any of the embodiments described herein, wherein the formulation further comprises a buffering agent. In some embodiments, the buffering agent is selected from the group consisting of phosphate, acetate, histidine, succinate, Tris, and combinations thereof. In some embodiments, the buffering agent is phosphate. In some embodiments, the phosphate is present at a concentration no greater than 50 mM (e.g., no greater than 45 mM, 40 mM, 35 mM, 30 mM, 25 mM, 20 mM, 15 mM, 10 mM, or 5 mM). In some embodiments, the phosphate is present at a concentration no greater than 20 mM. In various aspects the invention includes a stable formulation of any of the embodiments described herein, wherein the formulation has a pH of approximately 3-8 (e.g., approximately 4-7.5, 5-8, 5-7.5, 5-6.5, 5-7.0, 5.5-8.0, 5.5-7.7, 5.5-6.5, 6-7.5, or 6-7.0). In some embodiments, the formulation has a pH of approximately 5.5-6.5 (e.g., 5.5, 6.0, 6.1, 6.2, 6.3, 6.4, or 6.5). In some embodiments, the formulation has a pH of approximately 6.0.

In various embodiments, the present invention includes stable formulations of any of the embodiments described herein, wherein the formulation is a liquid formulation. In various embodiments, the present invention includes stable formulation of any of the embodiments described herein, wherein the formulation is formulated as lyophilized dry powder.

In some embodiments, the present invention includes a stable formulation for intrathecal administration comprising an iduronate-2-sulfatase (I2S) protein at a concentration ranging from approximately 1-300 mg/ml, NaCl at a concentration of approximately 154 mM, polysorbate 20 at a concentration of approximately 0.005%, and a pH of approximately 6.0. In some embodiments, the I2S protein is at a concentration of approximately 10 mg/ml. In some embodiments, the I2S protein is at a concentration of approximately 30 mg/ml, 40 mg/ml, 50 mg/ml, 75 mg/ml, 100 mg/ml, 150 mg/ml, 200 mg/ml, 250 mg/ml, or 300 mg/ml.

In various aspects, the present invention includes a container comprising a single dosage form of a stable formulation in various embodiments described herein. In some embodiments, the container is selected from an ampule, a vial, a bottle, a cartridge, a reservoir, a lyo-ject, or a pre-filled syringe. In some embodiments, the container is a pre-filled syringe. In some embodiments, the pre-filled syringe is selected from borosilicate glass syringes with baked silicone coating, borosilicate glass syringes with sprayed silicone, or plastic resin syringes without silicone. In some embodiments, the stable formulation is present in a volume of less than about 50 mL (e.g., less than about 45 ml, 40 ml, 35 ml, 30 ml, 25 ml, 20 ml, 15 ml, 10 ml, 5 ml, 4 ml, 3 ml, 2.5 ml, 2.0 ml, 1.5 ml, 1.0 ml, or 0.5 ml). In some embodiments, the stable formulation is present in a volume of less than about 3.0 mL.

In various aspects, the present invention includes methods of treating Hunters Syndrome including the step of administering intrathecally to a subject in need of treatment a formulation according to any of the embodiments described herein.

In some embodiments, the present invention includes a method of treating Hunters Syndrome including a step of administering intrathecally to a subject in need of treatment a formulation comprising an iduronate-2-sulfatase (I2S) protein at a concentration ranging from approximately 1-300 mg/ml, NaCl at a concentration of approximately 154 mM, polysorbate 20 at a concentration of approximately 0.005%, and a pH of approximately 6.

In some embodiments, the intrathecal administration results in no substantial adverse effects (e.g., severe immune response) in the subject. In some embodiments, the intrathecal administration results in no substantial adaptive T cell-mediated immune response in the subject.

In some embodiments, the intrathecal administration of the formulation results in delivery of the I2S protein to various target tissues in the brain, the spinal cord, and/or peripheral organs. In some embodiments, the intrathecal administration of the formulation results in delivery of the I2S protein to target brain tissues. In some embodiments, the brain target tissues comprise white matter and/or neurons in the gray matter. In some embodiments, the I2S protein is delivered to neurons, glial cells, perivascular cells and/or meningeal cells. In some embodiments, the I2S protein is further delivered to the neurons in the spinal cord.

In some embodiments, the intrathecal administration of the formulation further results in systemic delivery of the I2S protein to peripheral target tissues. In some embodiments, the peripheral target tissues are selected from liver, kidney, spleen and/or heart.

In some embodiments, the intrathecal administration of the formulation results in cellular lysosomal localization in brain target tissues, spinal cord neurons and/or peripheral target tissues. In some embodiments, the intrathecal administration of the formulation results in reduction of GAG storage in the brain target tissues, spinal cord neurons and/or peripheral target tissues. In some embodiments, the GAG storage is reduced by at least 10%, 20%, 30%, 40%, 50%, 60%, 70%, 80%, 90%, 1-fold, 1.5-fold, or 2-fold as compared to a control (e.g., the pre-treatment GAG storage in the subject). In some embodiments, the intrathecal administration of the formulation results in reduced vacuolization in neurons (e.g., by at least 20%, 40%, 50%, 60%, 80%, 90%, 1-fold, 1.5-fold, or 2-fold as compared to a control). In some embodiments, the neurons comprise Purkinje cells.

In some embodiments, the intrathecal administration of the formulation results in increased I2S enzymatic activity in the brain target tissues, spinal cord neurons and/or peripheral target tissues. In some embodiments, the I2S enzymatic activity is increased by at least 1-fold, 2-fold, 3-fold, 4-fold, 5-fold, 6-fold, 7-fold, 8-fold, 9-fold or 10-fold as compared to a control (e.g., the pre-treatment endogenous enzymatic activity in the subject). In some embodiments, the increased I2S enzymatic activity is at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg or 600 nmol/hr/mg.

In some embodiments, the I2S enzymatic activity is increased in the lumbar region. In some embodiments, the increased I2S enzymatic activity in the lumbar region is at least approximately 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, or 10,000 nmol/hr/mg.

In some embodiments, the intrathecal administration of the formulation results in reduced intensity, severity, or frequency, or delayed onset of at least one symptom or feature of the Hunters Syndrome. In some embodiments, the at least one symptom or feature of the Hunters Syndrome is cognitive impairment; white matter lesions; dilated perivascular spaces in the brain parenchyma, ganglia, corpus callosum, and/or brainstem; atrophy; and/or ventriculomegaly.

In some embodiments, the intrathecal administration takes place once every two weeks. In some embodiments, the intrathecal administration takes place once every month. In some embodiments, the intrathecal administration takes place once every two months. In some embodiments, the administration interval is twice per month. In some embodiments, the administration interval is once every week. In some embodiments, the administration interval is twice or several times per week. In some embodiments, the administration is continuous, such as through a continuous perfusion pump. In some embodiments, the intrathecal administration is used in conjunction with intravenous administration. In some embodiments, the intravenous administration is no more frequent than once every week. In some embodiments, the intravenous administration is no more frequent than once every two weeks. In some embodiments, the intravenous administration is no more frequent than once every month. In some embodiments, the intravenous administration is no more frequent than once every two months. In certain embodiments, the intraveneous administration is more frequent than monthly administration, such as twice weekly, weekly, every other week, or twice monthly.

In some embodiments, intraveneous and intrathecal administrations are performed on the same day. In some embodiments, the intraveneous and intrathecal administrations are not performed within a certain amount of time of each other, such as not within at least 2 days, within at least 3 days, within at least 4 days, within at least 5 days, within at least 6 days, within at least 7 days, or within at least one week. In some embodiments, intraveneous and intrathecal administrations are performed on an alternating schedule, such as alternating administrations weekly, every other week, twice monthly, or monthly. In some embodiments, an intrathecal administration replaces an intravenous administration in an administration schedule, such as in a schedule of intraveneous administration weekly, every other week, twice monthly, or monthly, every third or fourth or fifth administration in that schedule can be replaced with an intrathecal administration in place of an intraveneous administration.

In some embodiments, intraveneous and intrathecal administrations are performed sequentially, such as performing intraveneous administrations first (e.g., weekly, every other week, twice monthly, or monthly dosing for two weeks, a month, two months, three months, four months, five months, six months, a year or more) followed by IT administations (e.g., weekly, every other week, twice monthly, or monthly dosing for more than two weeks, a month, two months, three months, four months, five months, six months, a year or more). In some embodiments, intrathecal administrations are performed first (e.g., weekly, every other week, twice monthly, monthly, once every two months, once every three months dosing for two weeks, a month, two months, three months, four months, five months, six months, a year or more) followed by intraveneous administations (e.g., weekly, every other week, twice monthly, or monthly dosing for more than two weeks, a month, two months, three months, four months, five months, six months, a year or more).

In some embodiments, the intrathecal administration is used in absence of intravenous administration.

In some embodiments, the intrathecal administration is used in absence of concurrent immunosuppressive therapy.

BRIEF DESCRIPTION OF THE DRAWINGS

The drawings are for illustration purposes only, not for limitation.

Figure 5:
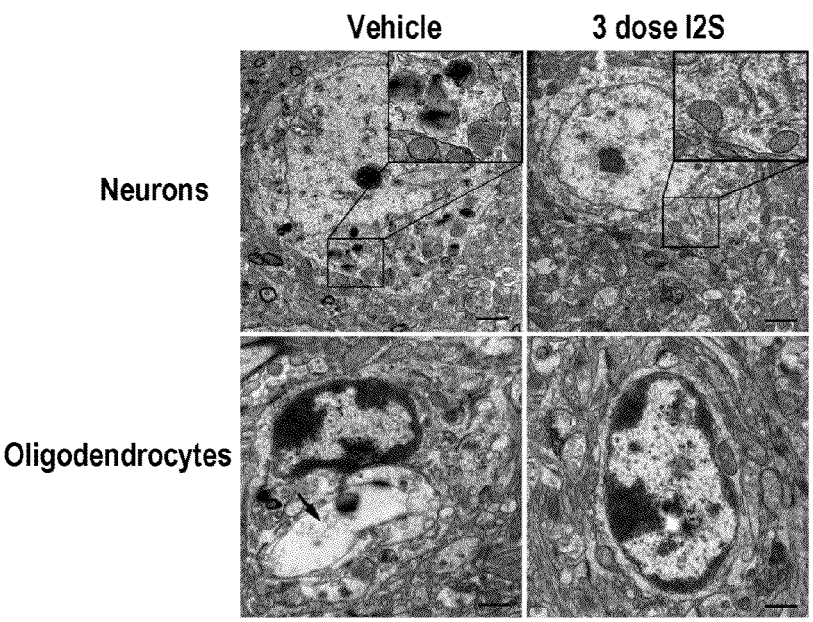

FIG. 5 depicts exemplary electron micrographs of brain cells showed pathological improvements at the ultrastructural level. Neurons of vehicle treated mice had lamellated inclusions, zebra body-like structures, and vacuoles containing granular storage material (insert), which was reduced in I2S injected mice. Oligodendrocytes of vehicle treated mice showed large electron-lucent storage vacuoles (arrow) while oligodendrocytes of I2S-injected mice had minimal vacuolation. Scale bar: in neurons, 2 μm; in oligodendrocytes, 500 nm.

Figure 6:
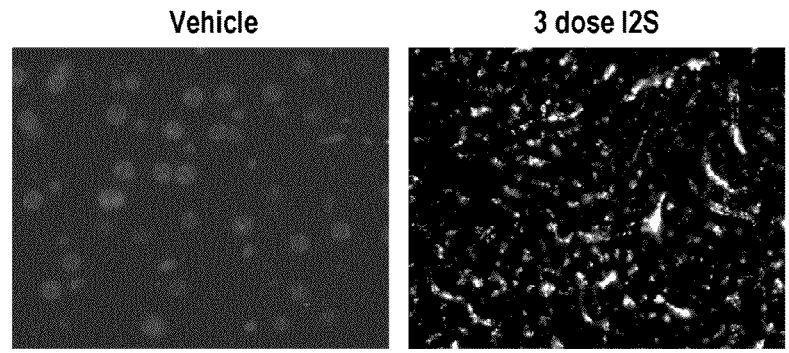

FIG. 6 depicts exemplary immunohistochemistry results demonstrating I2S detected in sinusoidal cells of the liver following intrathecal injections of 3 doses of I2S. 2S IHC staining in 2 dose injected livers was weaker (photo not shown). No positive I2S staining in the liver of vehicle controlled animals. 40×.

Figure 7:
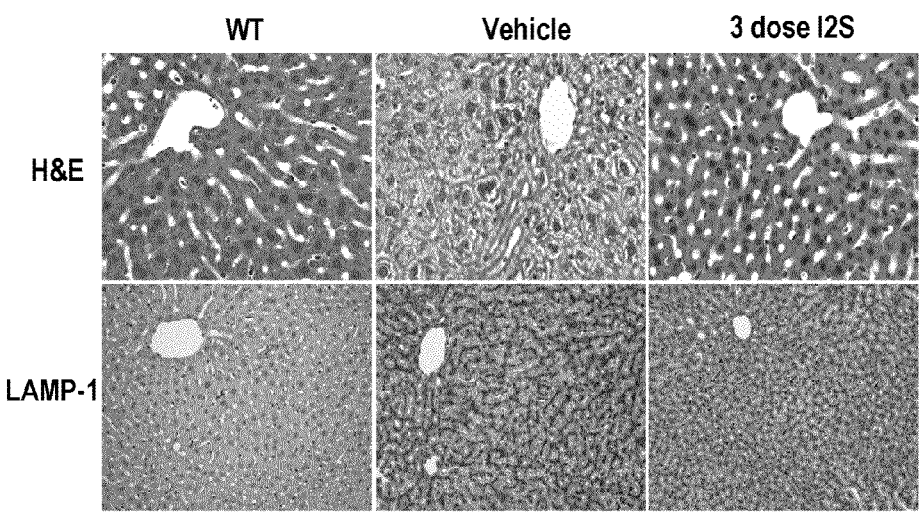
Figure 8A:
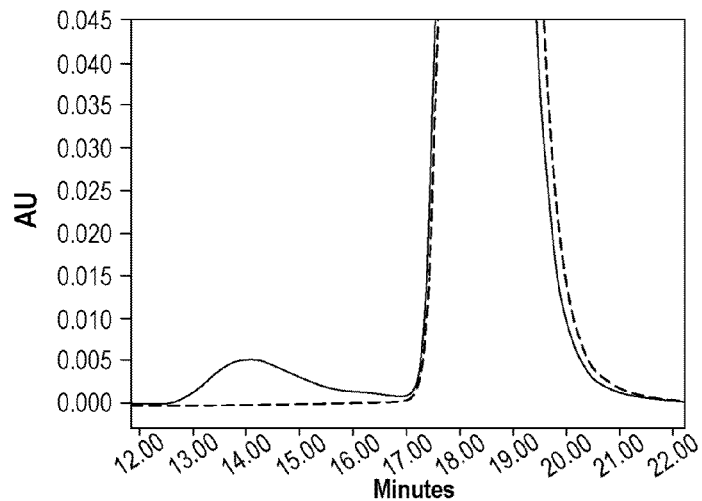
Figure 8B:
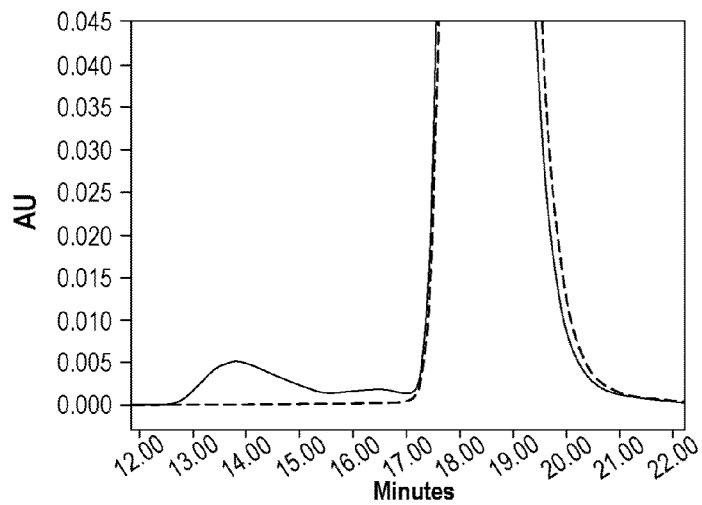
Figure 8C:
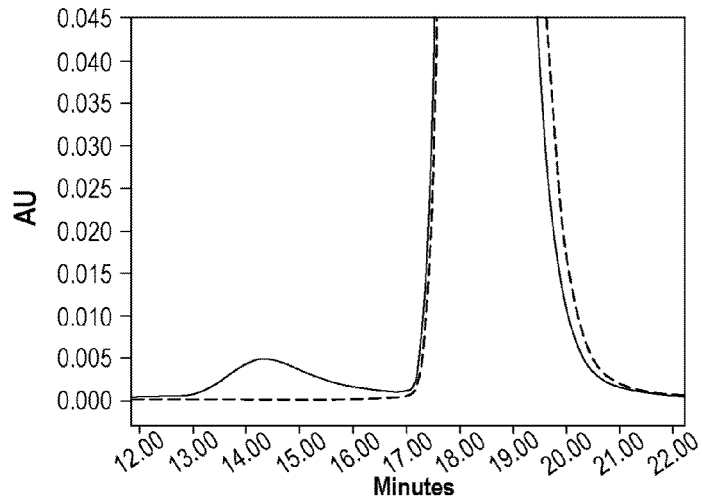
Figure 8D:
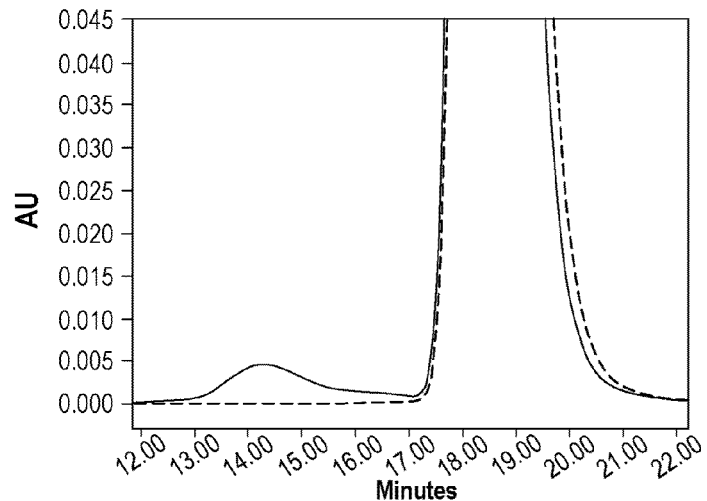
Figure 8E:
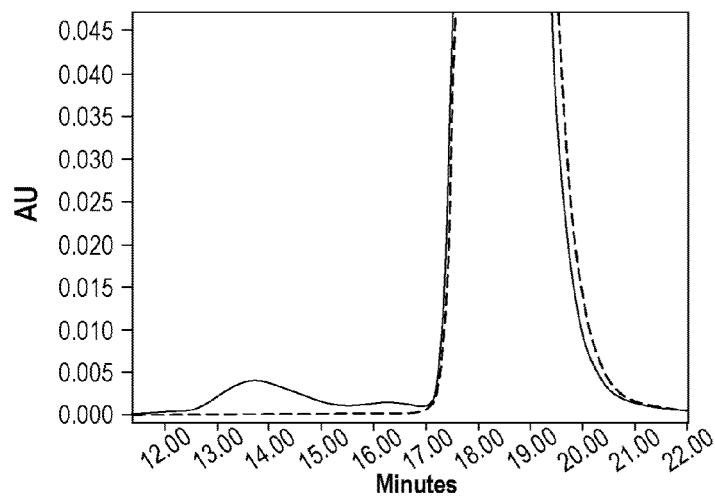
Figure 8F:
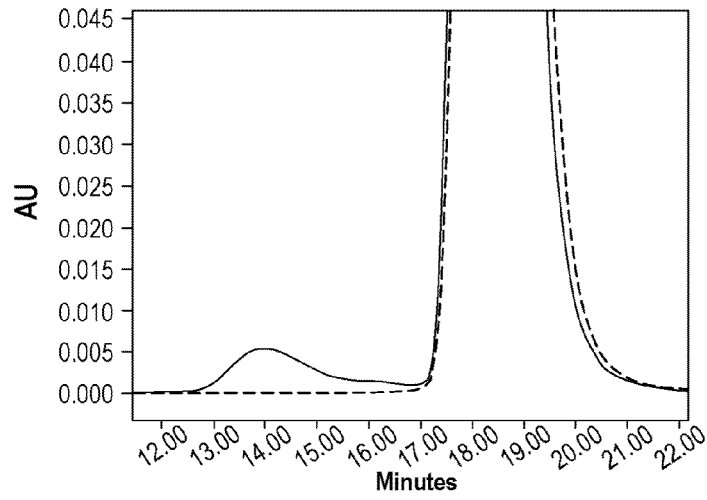
Figure 9A:
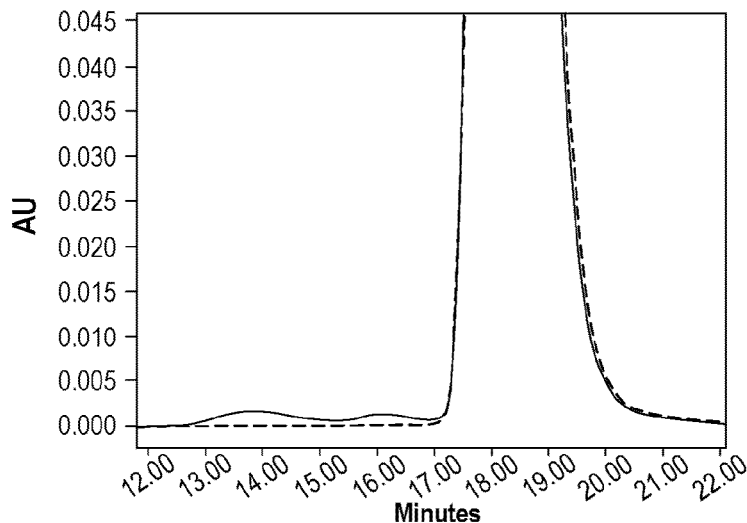
Figure 9B:
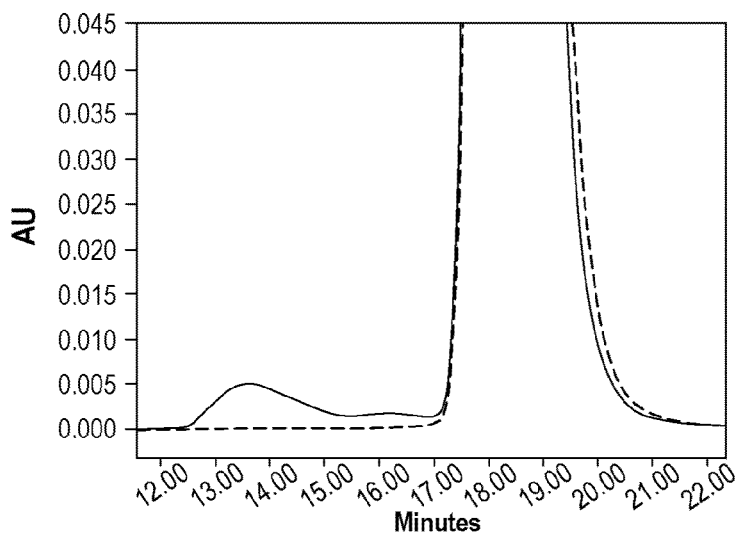
Figure 9C:
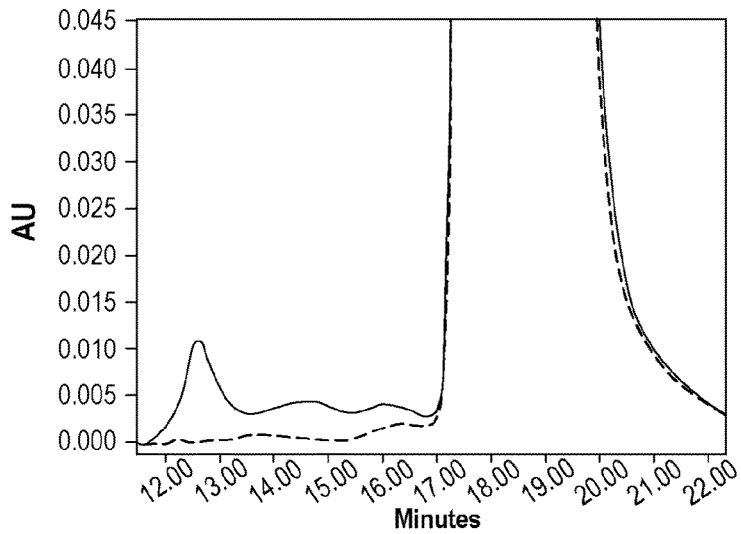
Figure 9D:
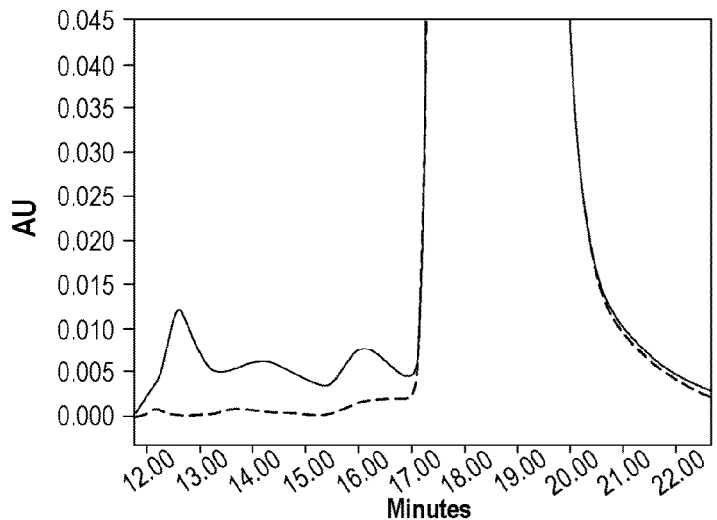
Figure 9E:
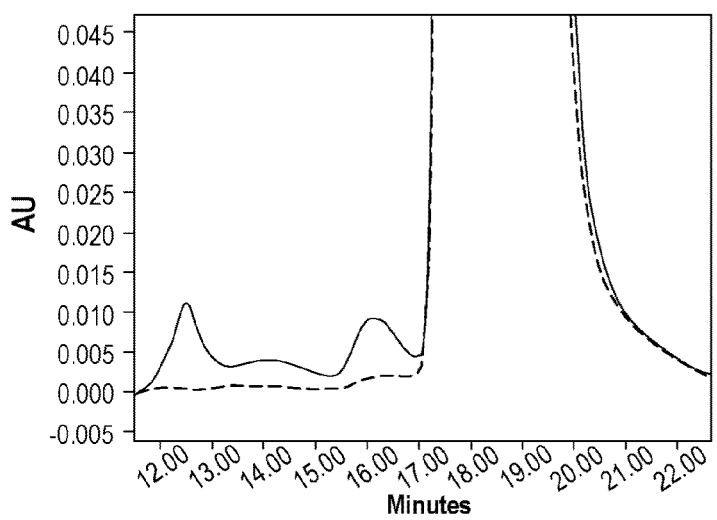
Figure 9F:
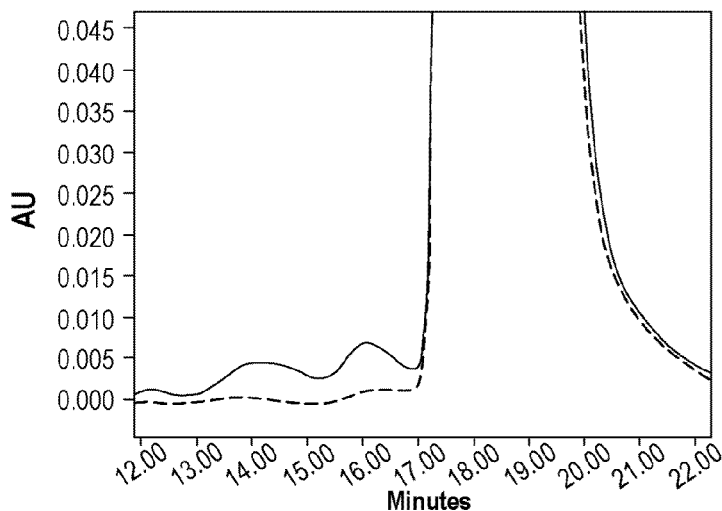
Figure 10A:
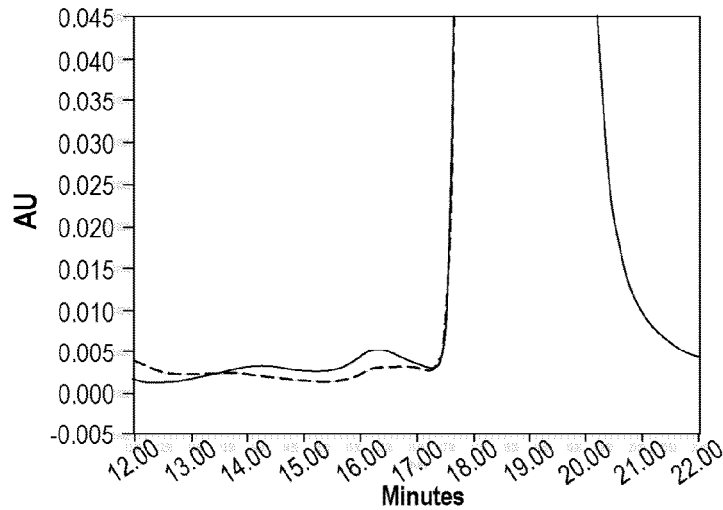
Figure 10B:
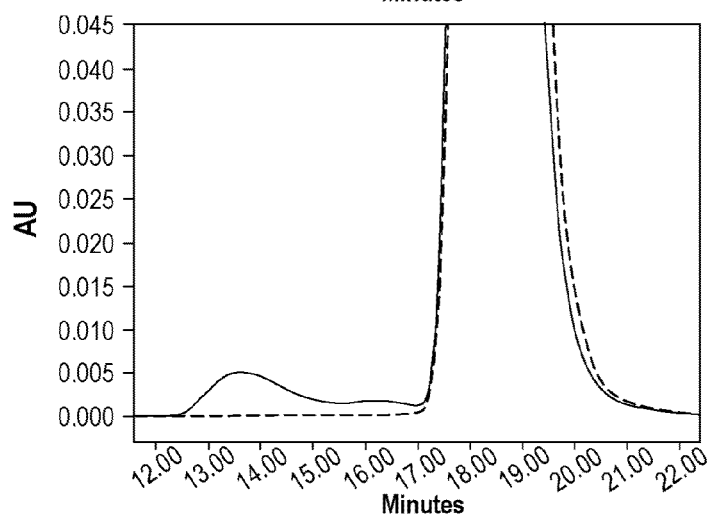
Figure 10C:
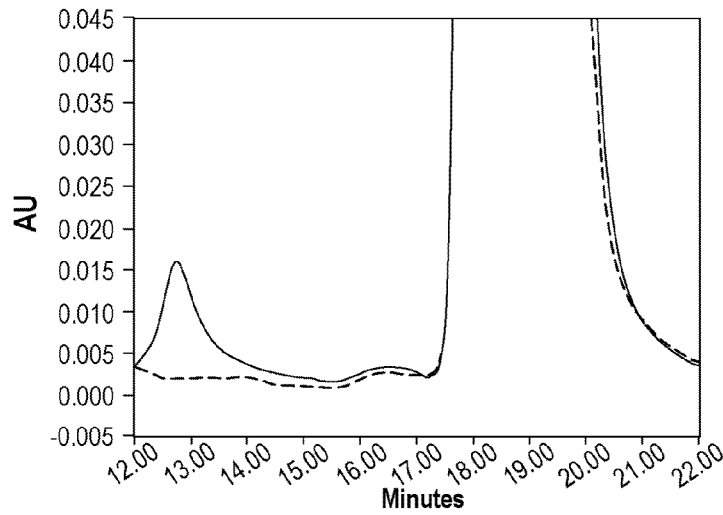
Figure 10D:
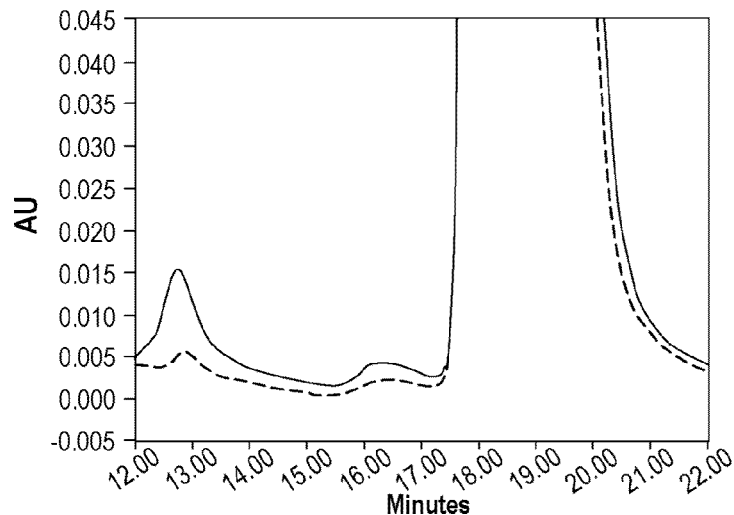
Figure 10E:
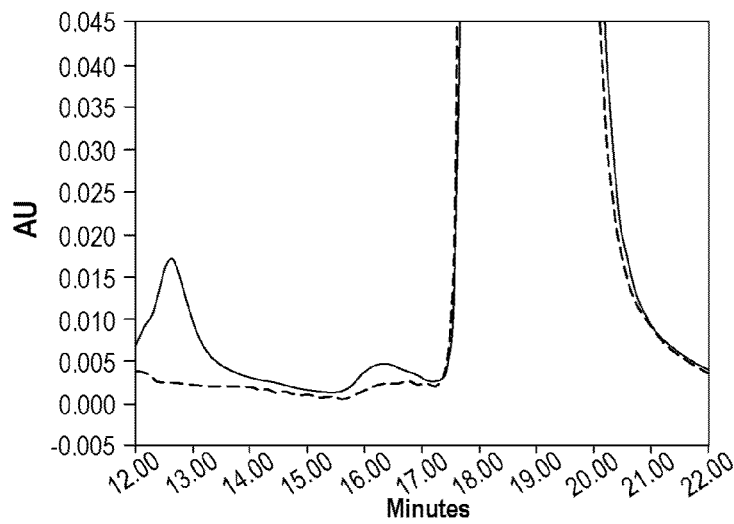
Figure 10F:
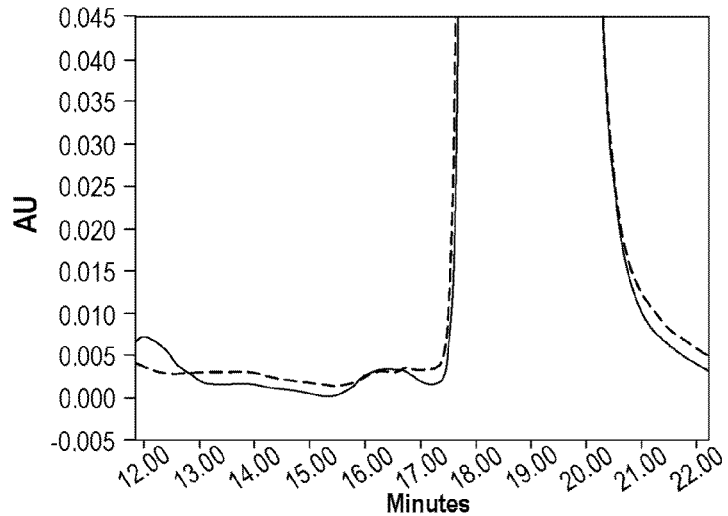
Figure 11A:
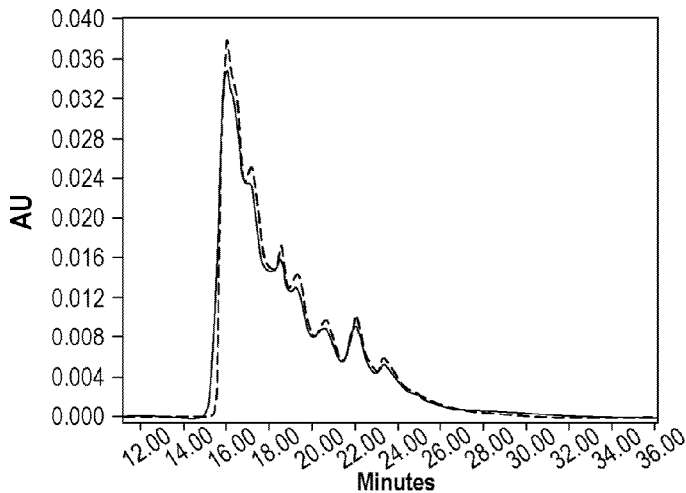
Figure 11B:
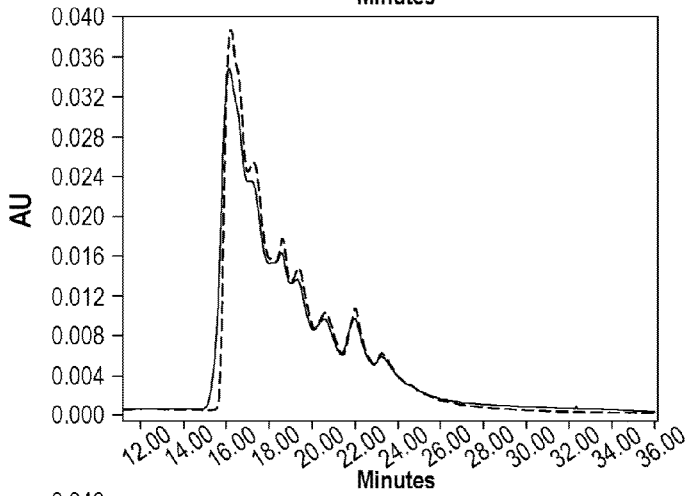
Figure 11C:
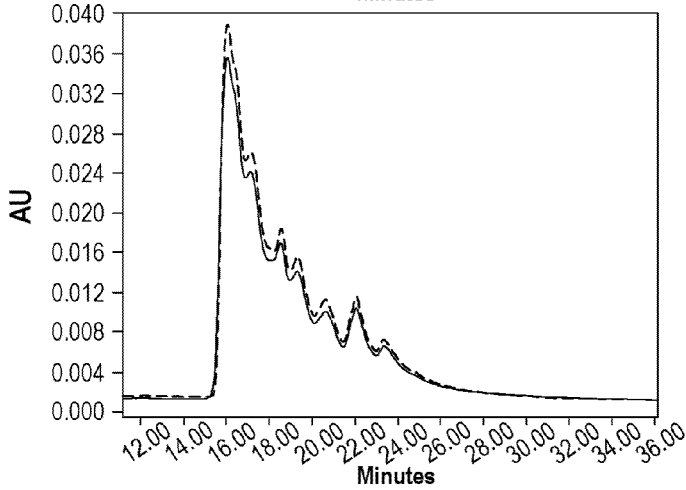
Figure 11D:
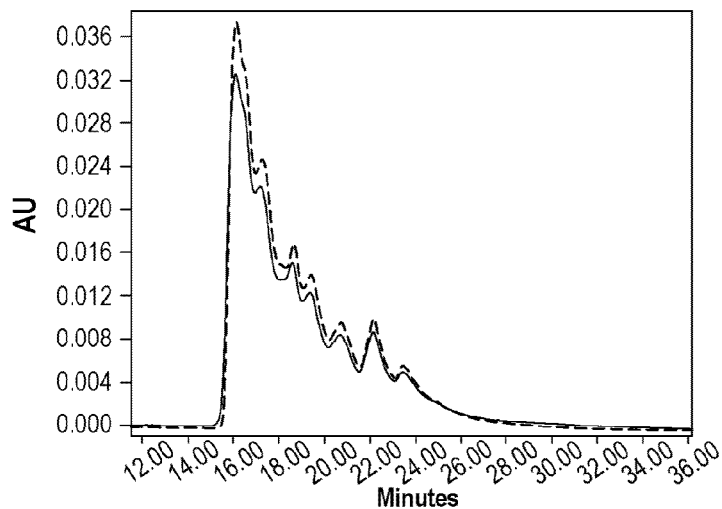
Figure 11E:
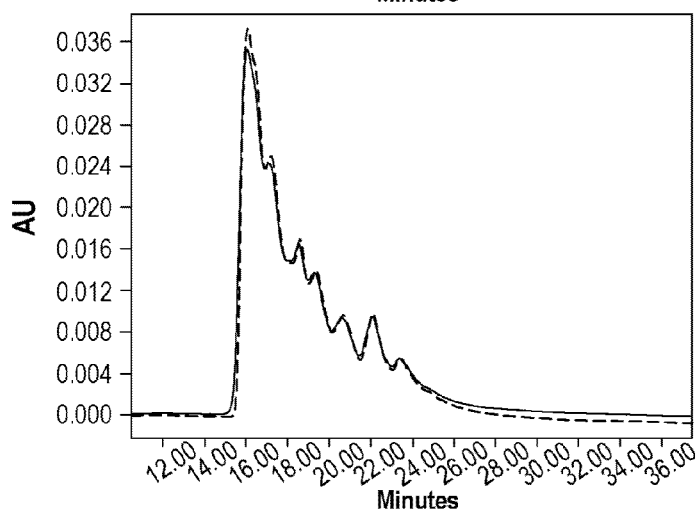
Figure 11F:
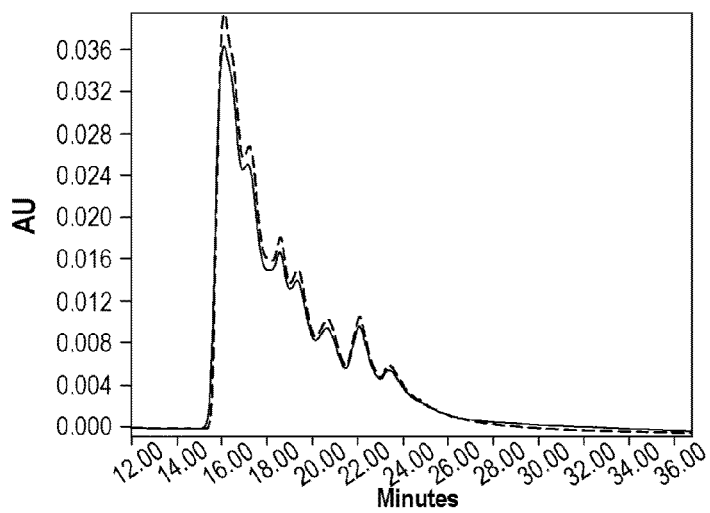
Figure 12A:
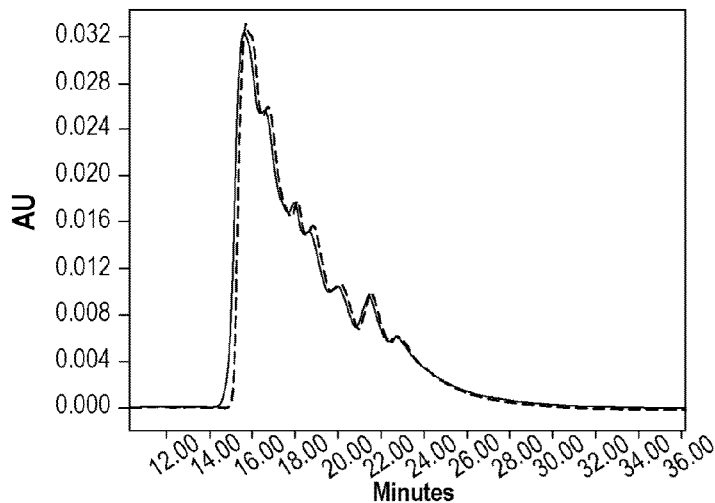
Figure 12B:
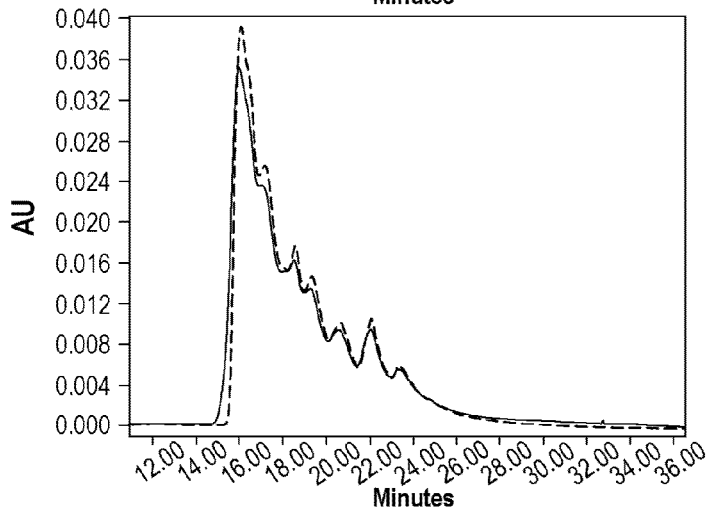
Figure 12C:
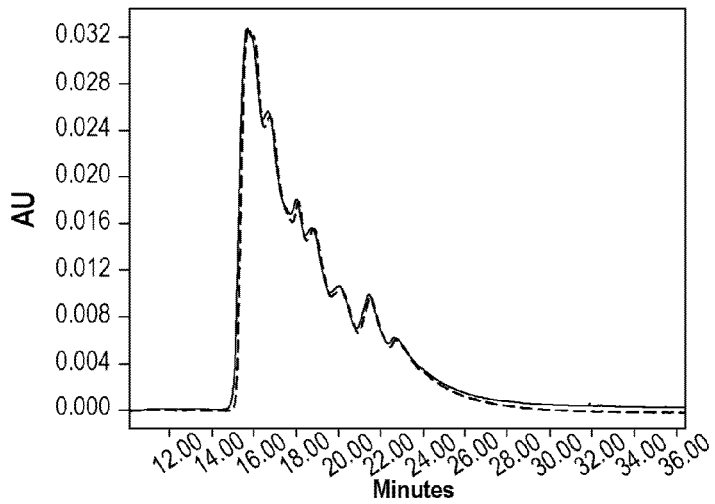
Figure 12D:
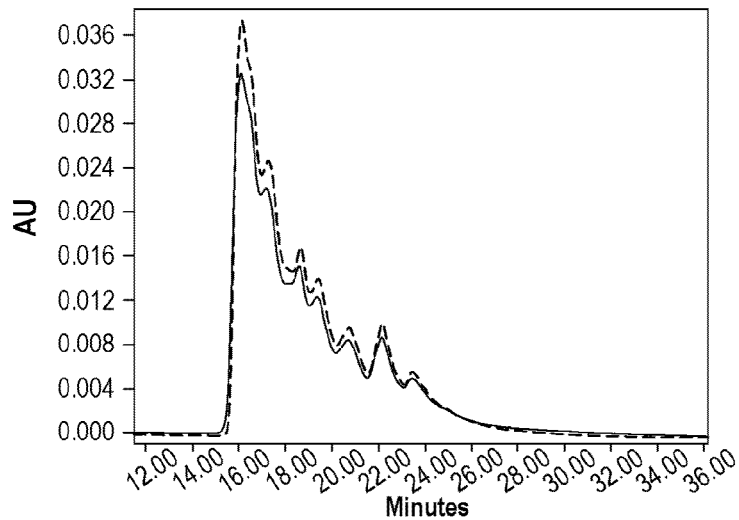
Figure 12E:
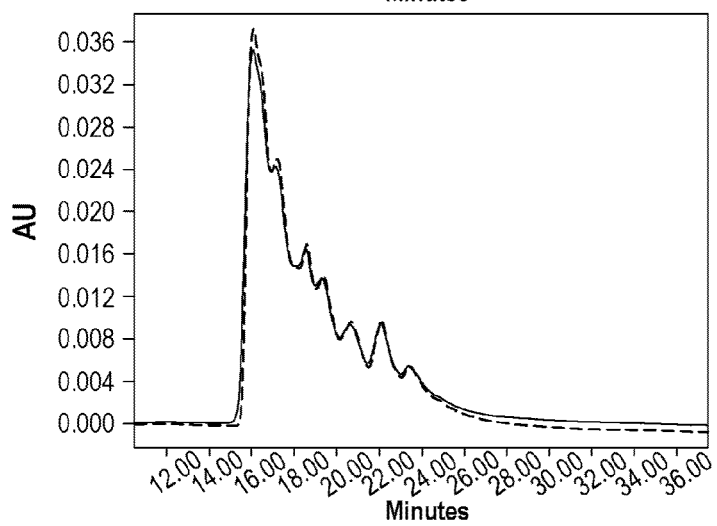
Figure 12F:
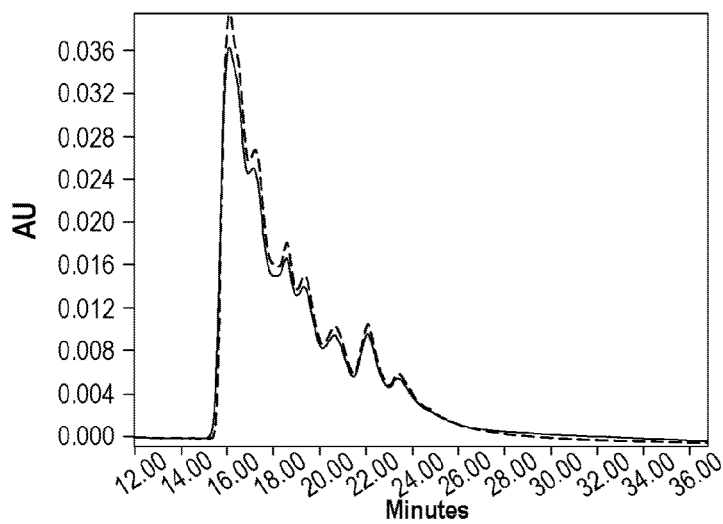
Figure 13A:
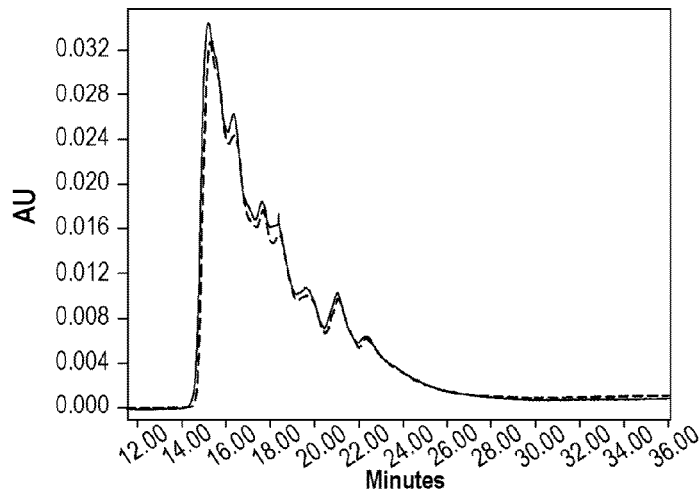
Figure 13B:
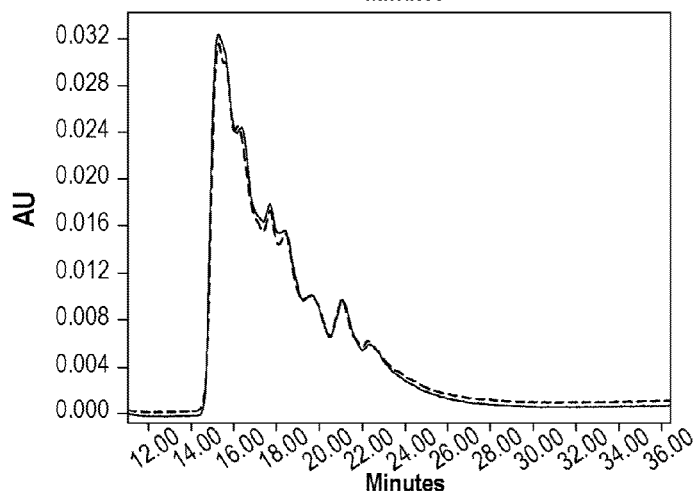
Figure 13C:
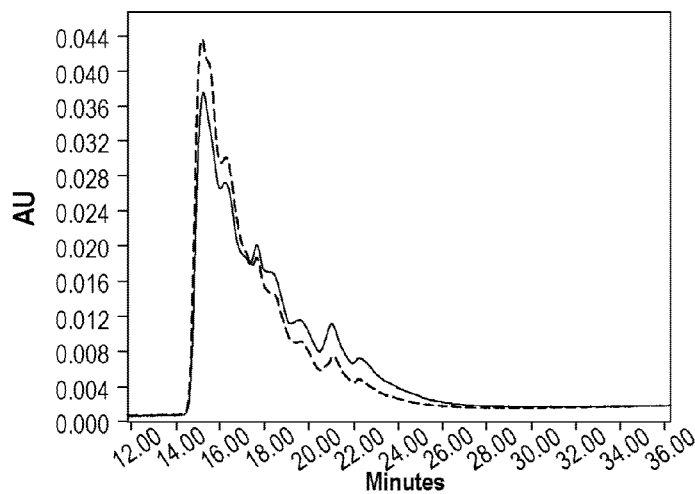
Figure 13D:
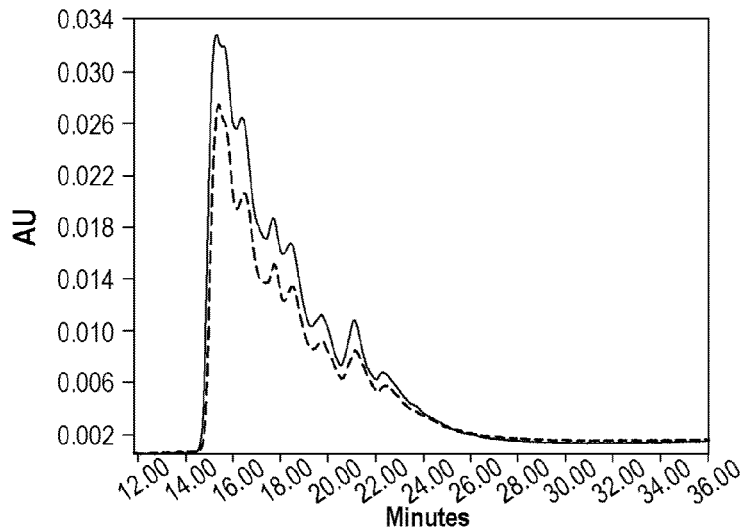
Figure 13E:
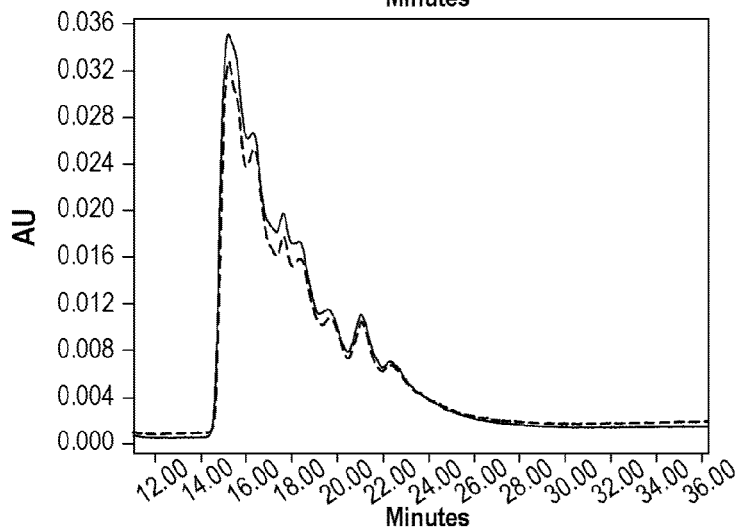
Figure 13F:
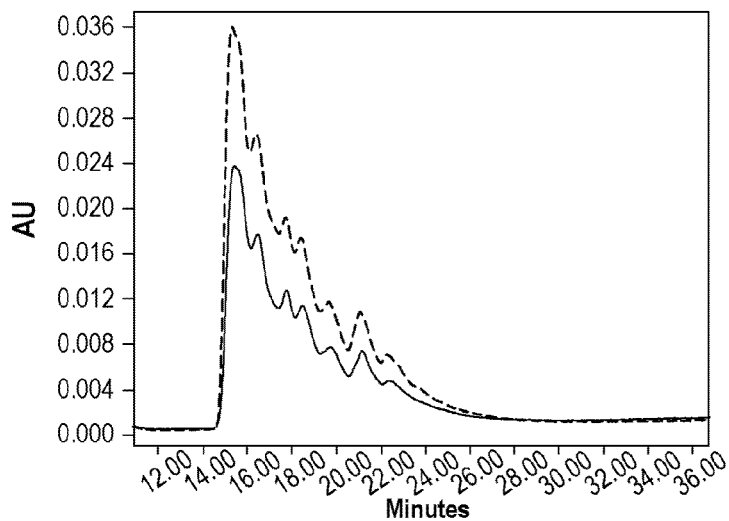

FIG. 7 depicts exemplary tissue from the liver. Severe cellular vacuolation and abnormally high lysosomal activity is revealed by H&E staining and strong LAMP-1 immunostaining were found in vehicle controlled animals compared to WT ones. Marked reduction of cellular vacuolation and LAMP-1 immunostaining was found after interthecal treatment with 3 and 2 (photo not shown) doses of I2S treatment. H&E staining revealed intracytoplasmic vacuolization was almost completely disappear with a nearly normal liver cell structure. H&E, 40×; LAMP-1, 20×.

FIG. 8A-F illustrate exemplary data comparing aggregation by SEC-HPLC for saline and phosphate formulations (all with 0.01% Polysorbate-20): 1 month at ≤−65° C. and 40° C.

FIG. 9 illustrates exemplary data comparing aggregation by SEC-HPLC method for saline and phosphate formulations (all with 0.01% Polysorbate-20): 6 month at ≤−65° C. and 25° C.

FIGS. 10A-F illustrate exemplary data comparing aggregation by SEC-HPLC method for saline and phosphate formulations (all with 0.01% Polysorbate-20): 24 months at ≤−65° C. and 2 to 8° C.

FIG. 11 illustrates exemplary data comparing charges by SAX-HPLC Method for saline and phosphate formulations (all with 0.01% Polysorbate-20): baseline versus 1 month at 40° C.

FIG. 12 illustrates exemplary data comparing charges by SAX-HPLC Method for saline and phosphate formulations (all with 0.01% Polysorbate-20): baseline versus 6 month at 25° C.

FIG. 13 illustrates exemplary data comparing charges by SAX-HPLC Method for Saline and Phosphate Formulations (all with 0.01% Polysorbate-20): baseline versus 24 month at 2 to 8° C.

Figure 14:
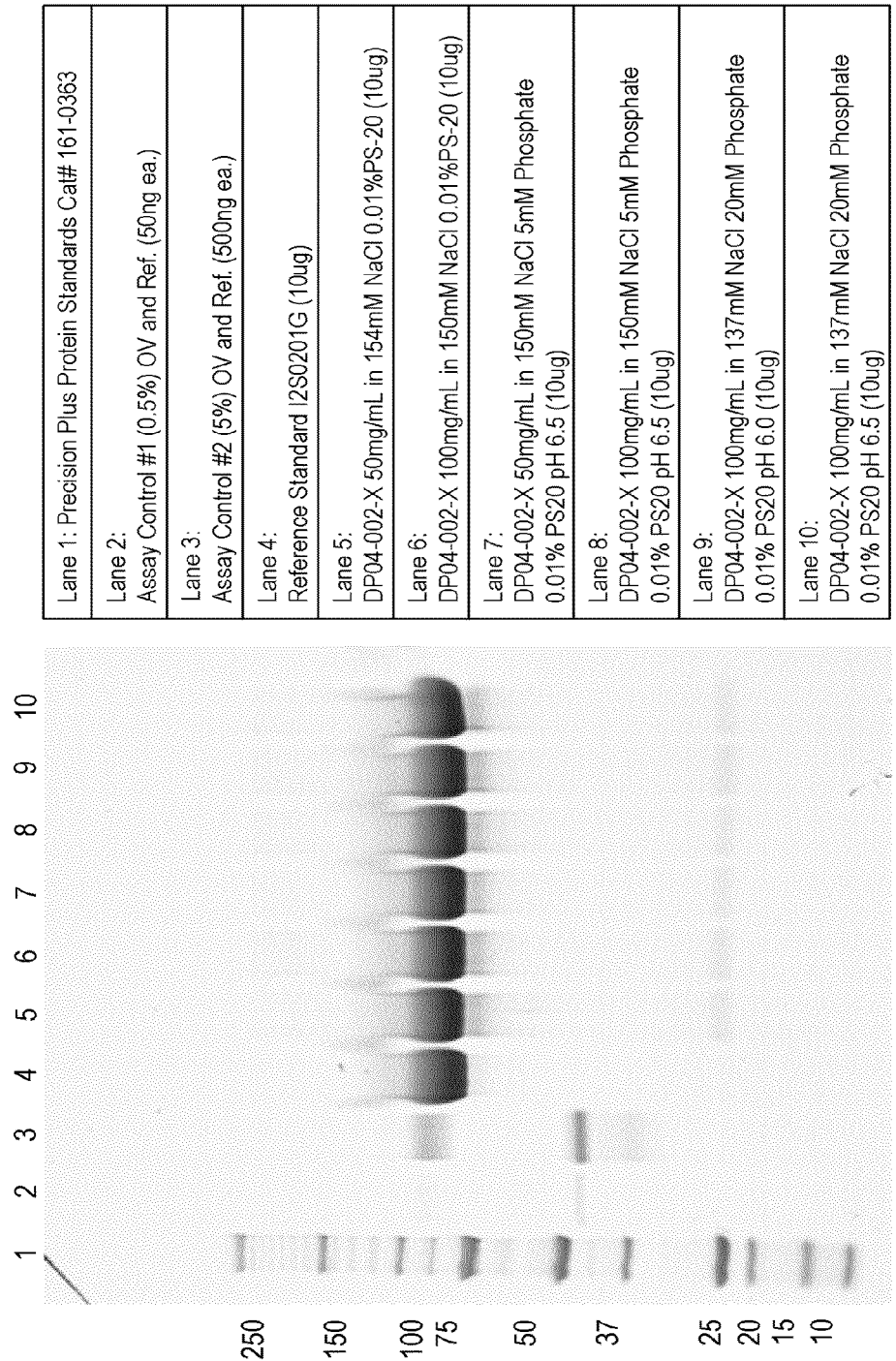

FIG. 14 illustrates exemplary data comparing SDS-PAGE, Coomassie staining for saline and phosphate formulations (all with 0.01% Polysorbate-20) at baseline and 1 month @ 40° C.

Figure 15A:
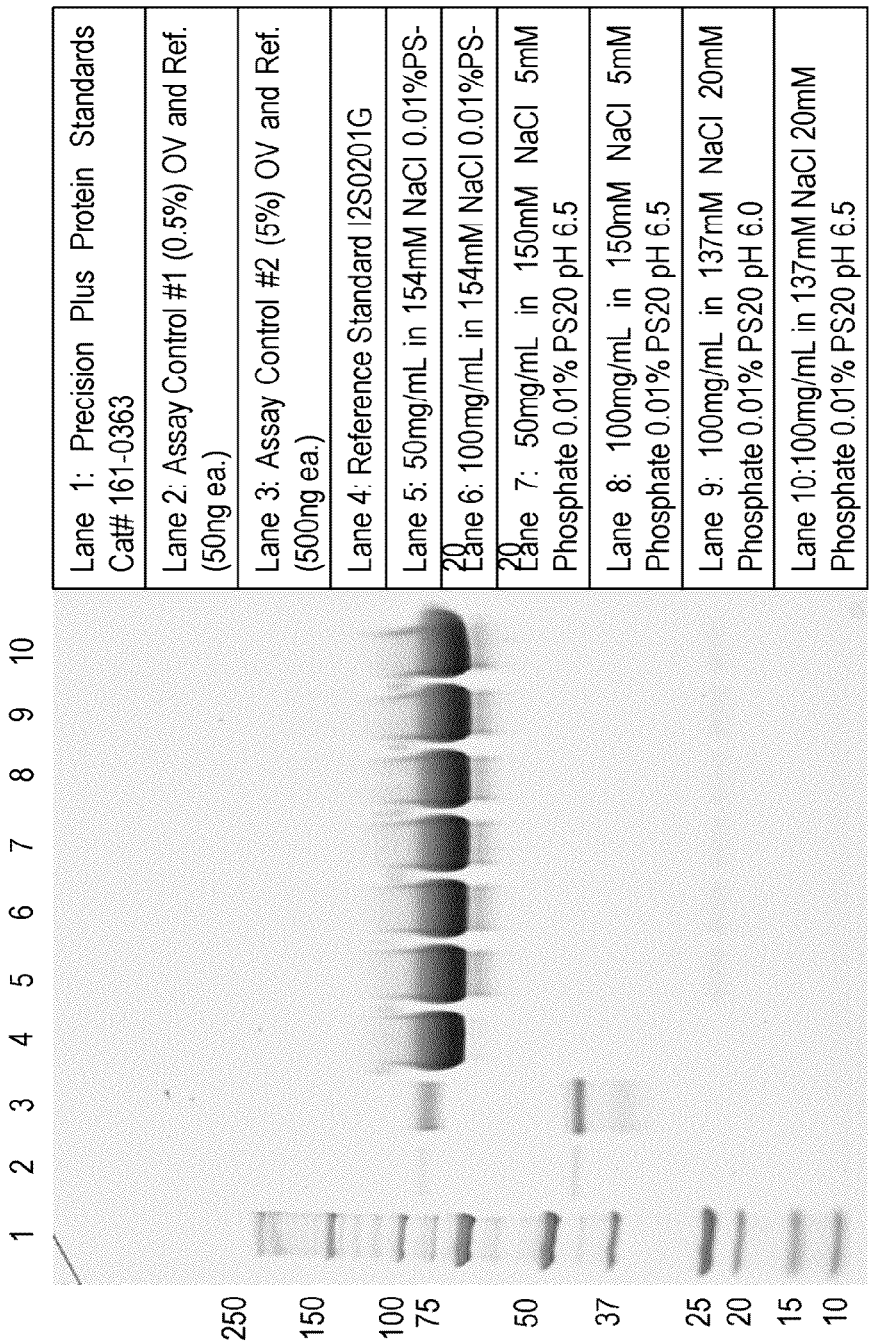
Figure 15B:
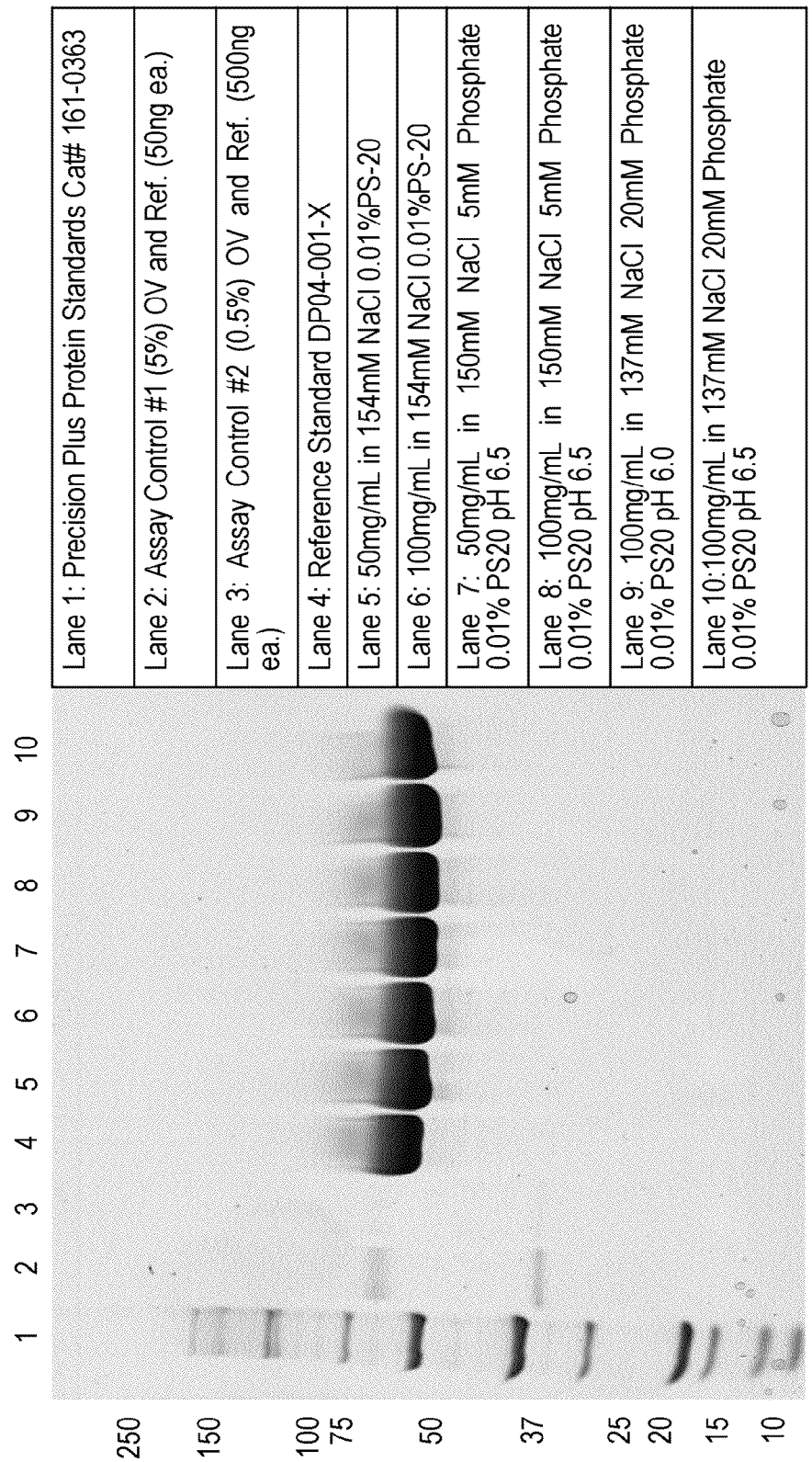

FIGS. 15A and B illustrate exemplary data comparing SDS-PAGE, Coomassie staining for saline and phosphate formulations (all with 0.01% Polysorbate-20) at 6 months 25° C. and over 16 months at 2-8° C.

Figure 16:
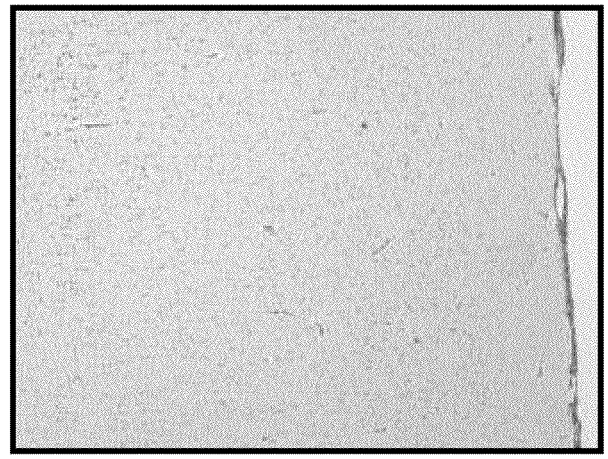

FIG. 16 depicts exemplary tissues showing cerebrum of a 3 mg treatment group animal. Positive I2S staining in meningeal cells. 4×.

Figure 17:
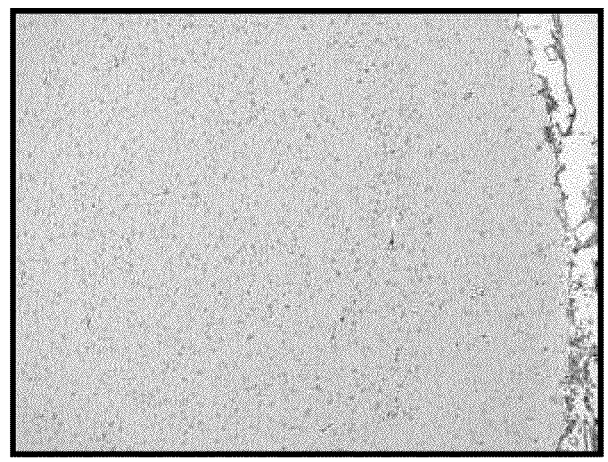

FIG. 17 depicts exemplary tissues showing cerebrum of a 30 mg treatment group animal. Positive I2S staining in neurons and meningeal cells. 4×

Figure 18:
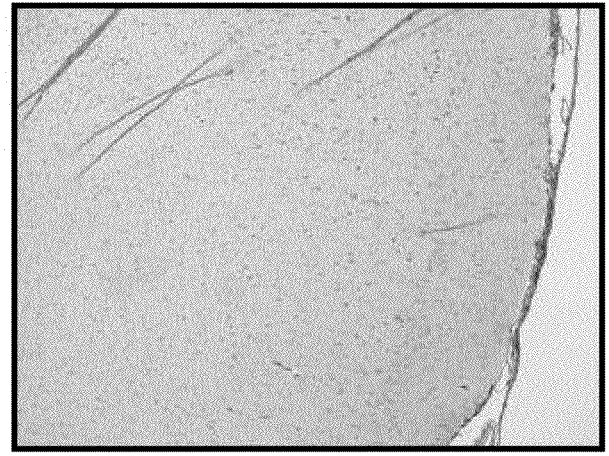

FIG. 18 depicts exemplary tissues showing cerebrum of 100 mg treatment group animal. Positive I2S staining neurons and meningeal cells was stronger than in 3 and 30 mg treated animals. 4×

Figure 19:
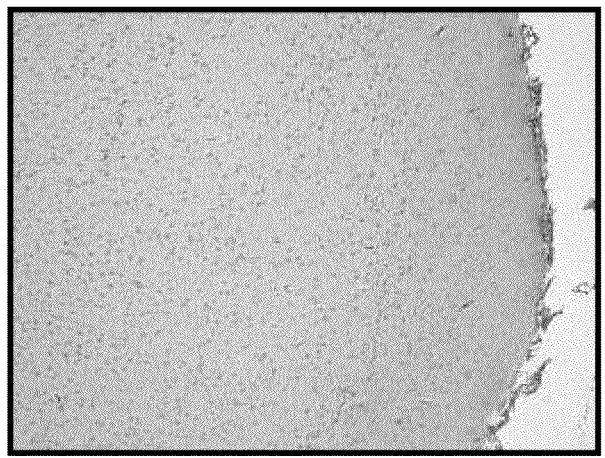

FIG. 19 depicts exemplary tissues showing cerebrum of a 150 mg treatment group animal. A large population of neurons was I2S positive along with strongly positive meningeal cells.

Figure 20:
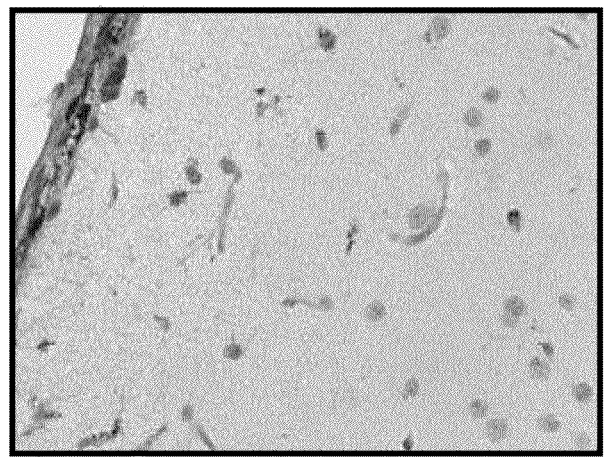

FIG. 20 depicts exemplary tissues showing I2S positive neurons and glial cells, along with meningeal cells, within layer I of the cerebrum in a 30 mg treatment group animal. 40×

Figure 21:
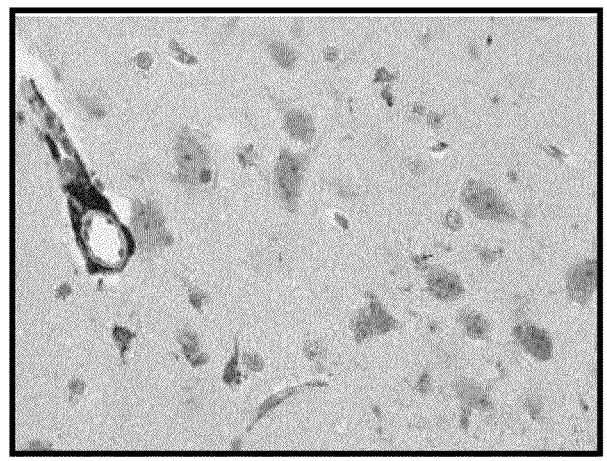

FIG. 21 depicts exemplary tissues showing I2S positive neurons, glial cells, along with perivascular cells, within layer III of the cerebrum in a 30 mg treatment group animal. 40×

Figure 22:
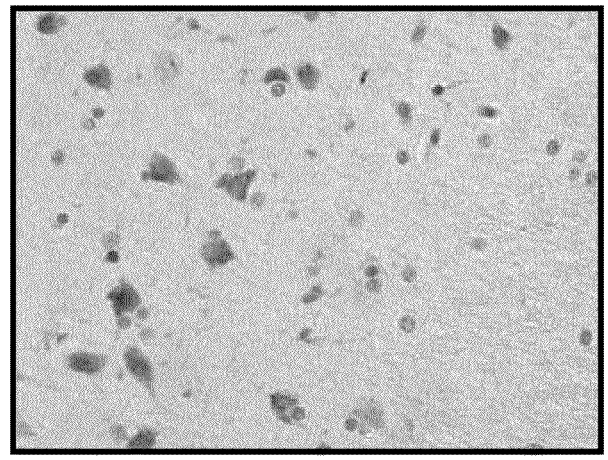

FIG. 22 depicts exemplary tissues showing I2S positive neurons and glial cells within the layer VI of cerebrum adjacent to the white matter in a 30 mg treatment group animal. 40×

Figure 23:
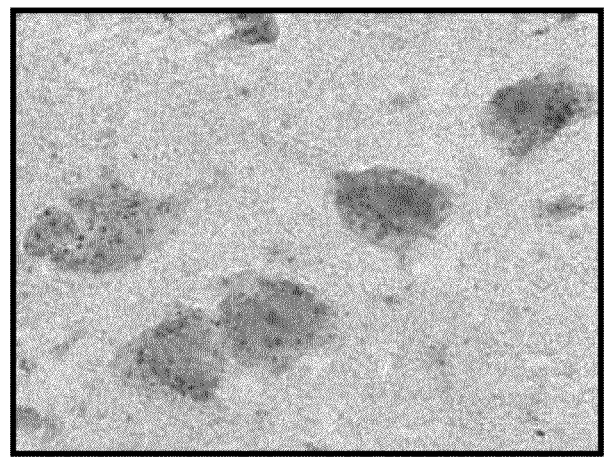

FIG. 23 depicts exemplary tissues showing strongly positive I2S staining in the neurons (cerebrum) of a 150 mg treatment group animal. 100×

Figure 24:
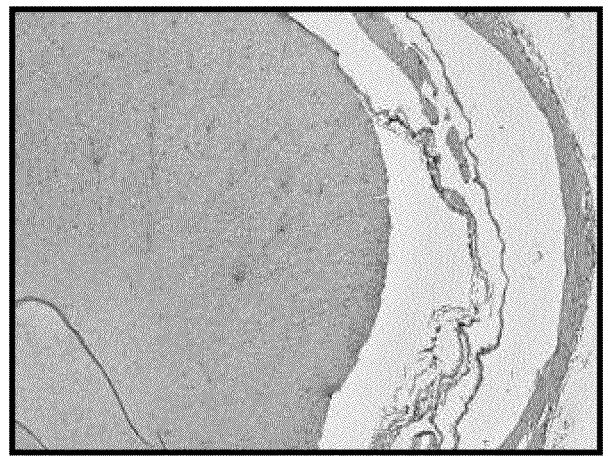

FIG. 24 depicts exemplary tissue showing I2S immunostaining of the cervical spinal cord in a 150 mg treatment group. 4×

Figure 25:
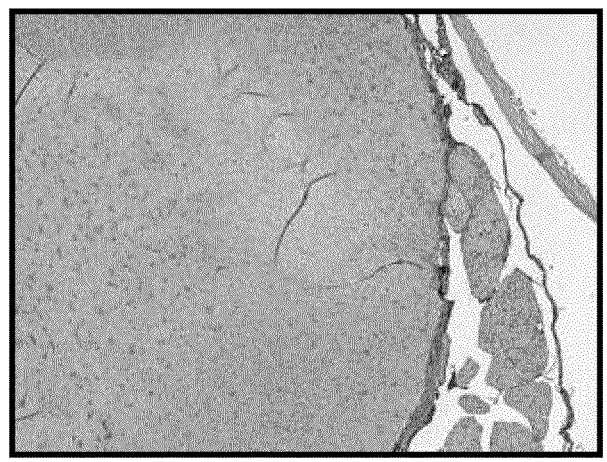

FIG. 25 depicts exemplary tissue showing strong I2S immunostaining in the lumbar spinal cord of a 150 mg treatment group animal. 4×

Figure 26:
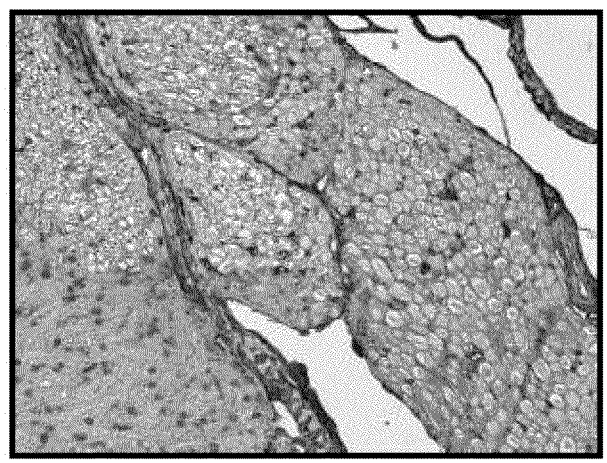

FIG. 26 depicts exemplary tissue showing strongly positive I2S immunostaining of meningial cells, glial cells, and epi/peri/endoneurium (connective cells) was found in the lumbar section of a 150 mg treatment group animal. 40×

Figure 27:
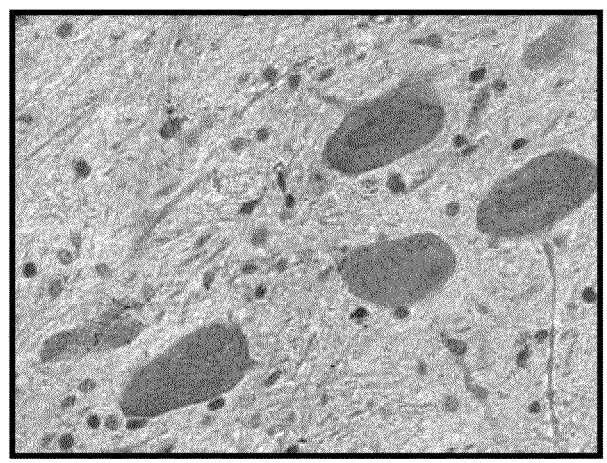

FIG. 27: The neurons in the lumbar spinal cord of a 150 mg treatment group animal were strongly I2S positive. 40×

Figure 28:
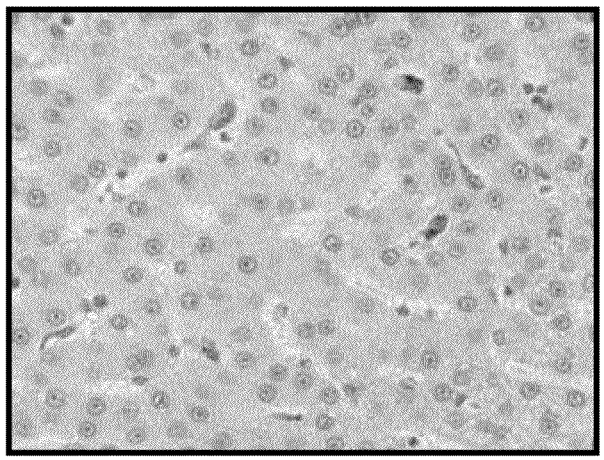

FIG. 28 depicts exemplary results from a liver from a 3 mg treatment group animal. Only sinusoidal cells were I2S positive. 40×

Figure 29:
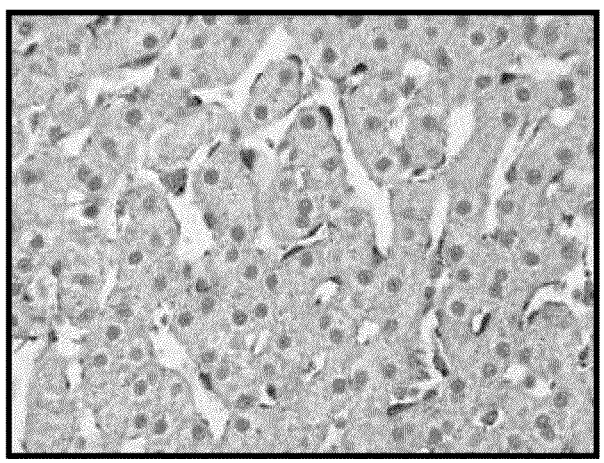

FIG. 29 depicts exemplary results from a liver from a 30 mg treatment group animal. Sinusoidal cells and hepatocytes were I2S positive. 40×

Figure 30:
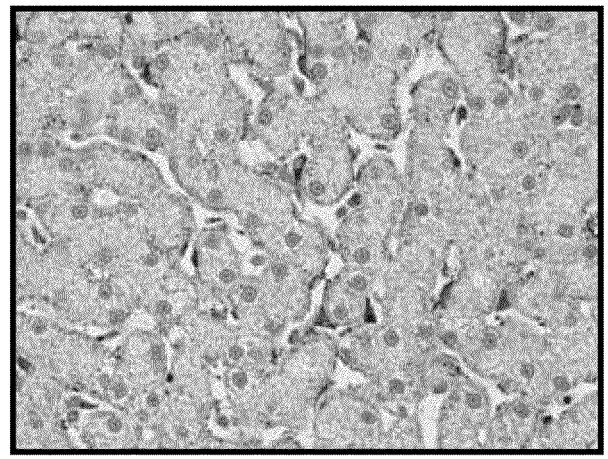

FIG. 30 depicts exemplary results from a liver from a 100 mg treatment group animal. I2S immunostaining was much stronger in the sinusoidal cells and the hepatocytes. 40×

Figure 31:
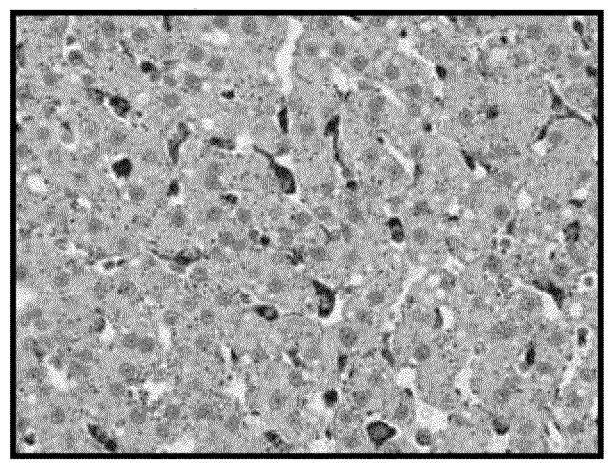

FIG. 31 depicts exemplary results from a liver from a 150 mg treatment group animal. Strongly positive I2S staining was identified in sinusoidal cells and hepatocytes. 40×

Figure 32:
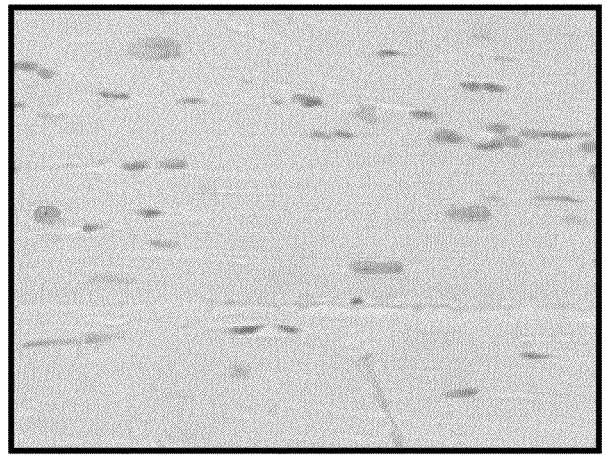

FIG. 32 depicts exemplary results from a heart from a 3 mg treatment group animal. I2S immunostaining was negative. 40×

Figure 33:
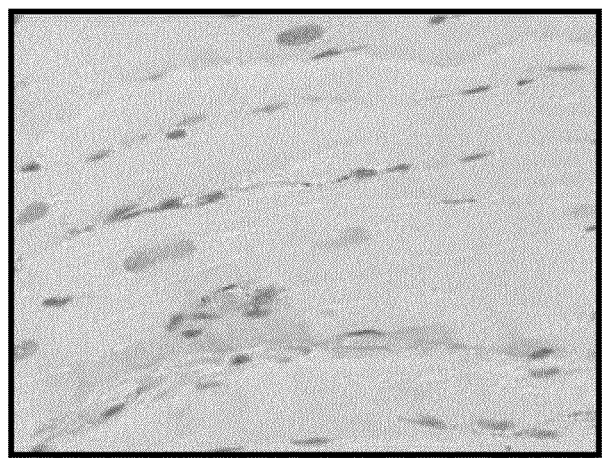

FIG. 33 depicts exemplary results from a heart from a 30 mg treatment group animal Interstitial cells were I2S positive. 40×

Figure 34:
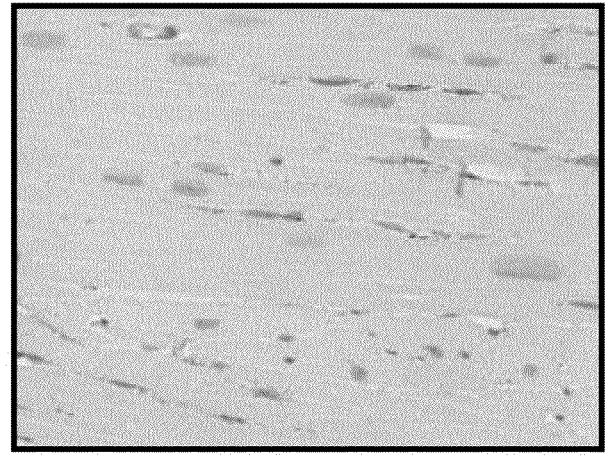

FIG. 34 depicts exemplary results from a heart from a 100 mg treatment group animal. Positive interstitial cell staining for I2S. 40×

Figure 35:
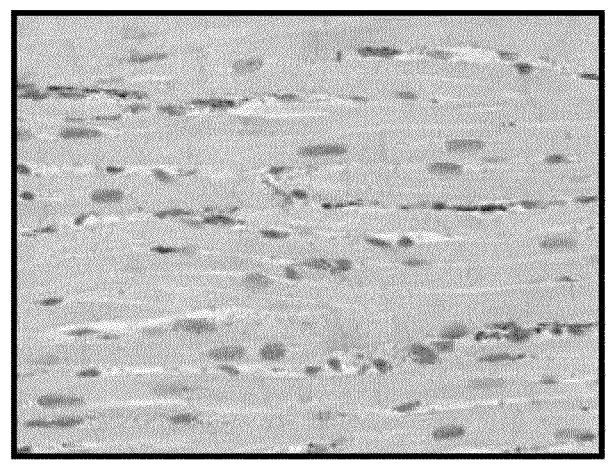

FIG. 35 depicts exemplary results from a heart from a 150 mg treatment group animal. Strongly positive interstitial cell staining for I2S. 40×

Figure 36:
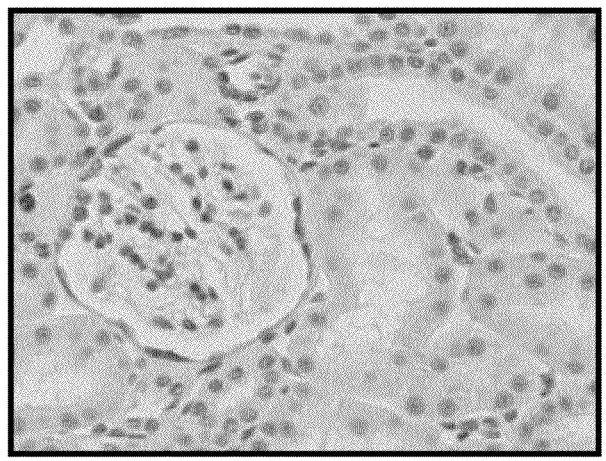

FIG. 36 depicts exemplary results from a kidney from a 3 mg treatment group animal. I2S immunostaining was negative. 40×

Figure 37:
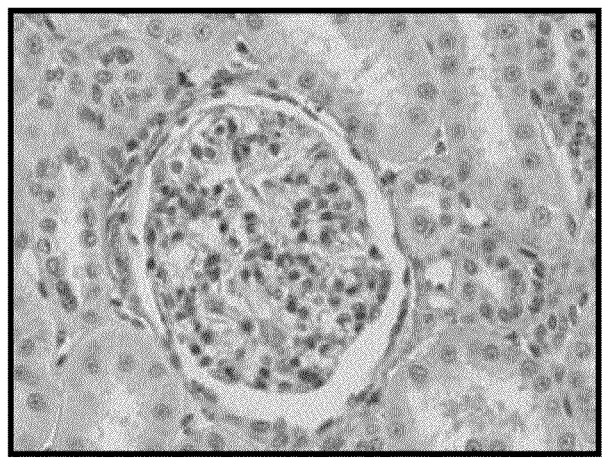

FIG. 37 depicts exemplary results from a kidney from a 30 mg treatment group animal. Glomerular and interstitial cells were I2S positive.

Figure 38:
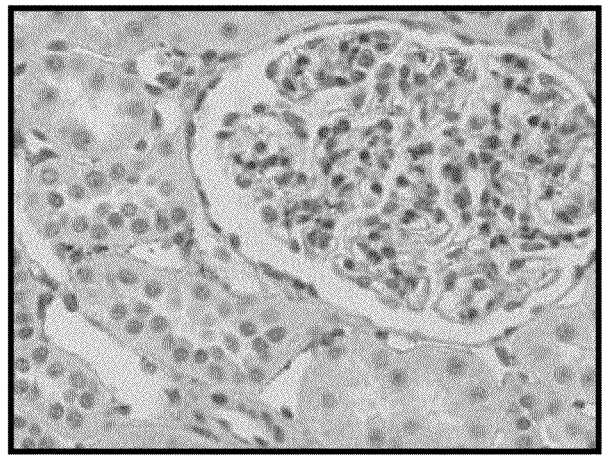

FIG. 38 depicts exemplary results from a kidney from a 100 mg treatment group animal. Increased glomerular and interstitial cell staining for I2S. 40×

Figure 39:

FIG. 39 depicts exemplary results from a kidney from a 150 mg treatment group animal. Positive I2S staining of proximal tubular, glomerular and interstitial cells. 40×

Figure 40:
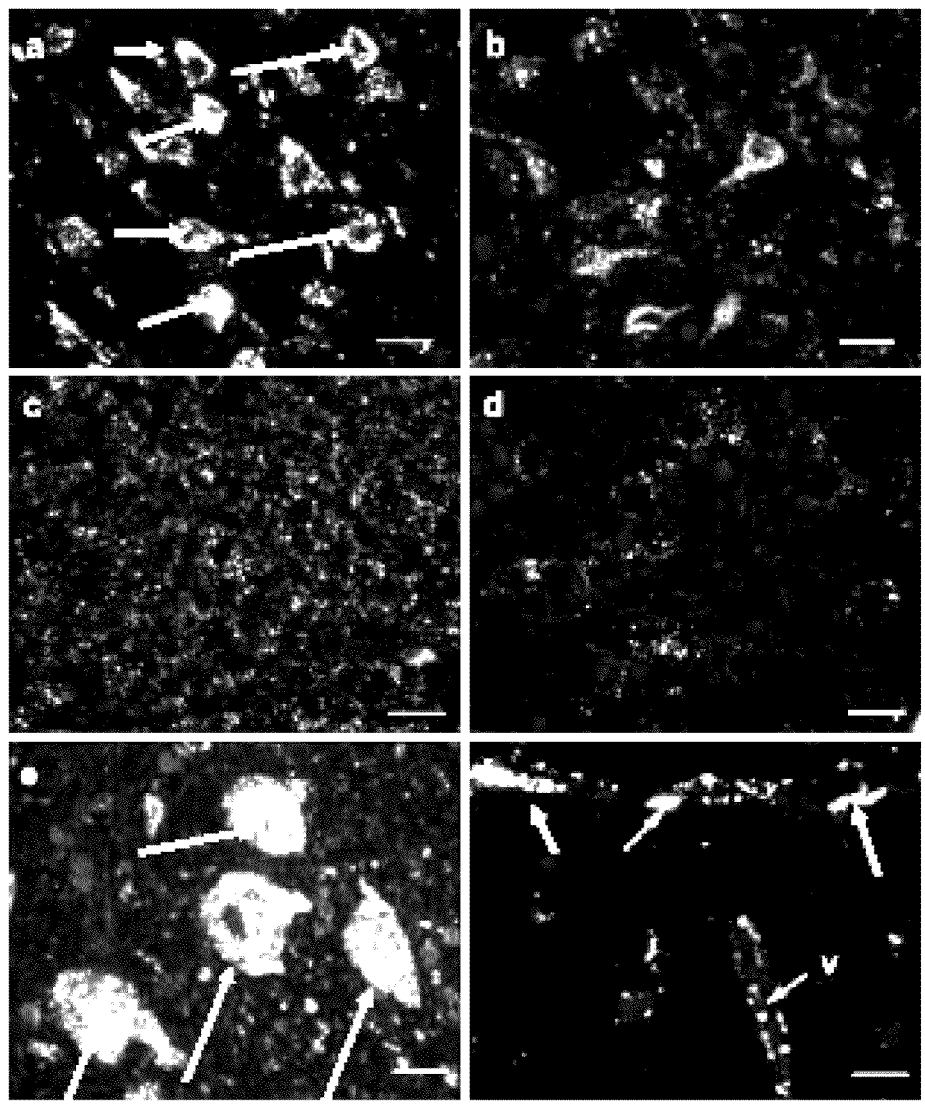

FIG. 40 illustrates the results of immunohistochemistry (IHC) studies evaluating the CNS tissues of cynomolgus monkeys administered weekly doses of iduronate-2-sulfatase (I2S). As determined by (IHC), there was widespread cellular deposition of I2S throughout the CNS. In the gray matter I2S was detected in the neurons of the cerebrum, cerebellum, brain stem, and spinal cord of all groups in a dose-dependent manner. In the surface gray matter of the higher dose groups, large numbers of cerebral neurons were positive for I2S staining in the surface cortex (FIG. 40A). I2S was also detected in neurons in the thalamus (FIG. 40B), hippocampus (FIG. 40C), caudate nucleus (FIG. 40D) and spinal cord (FIG. 40E). Meningial and perivascular cells were also I2S staining positive (FIG. 40F). The identified scale bars correspond to 25 μm.

Figure 41:
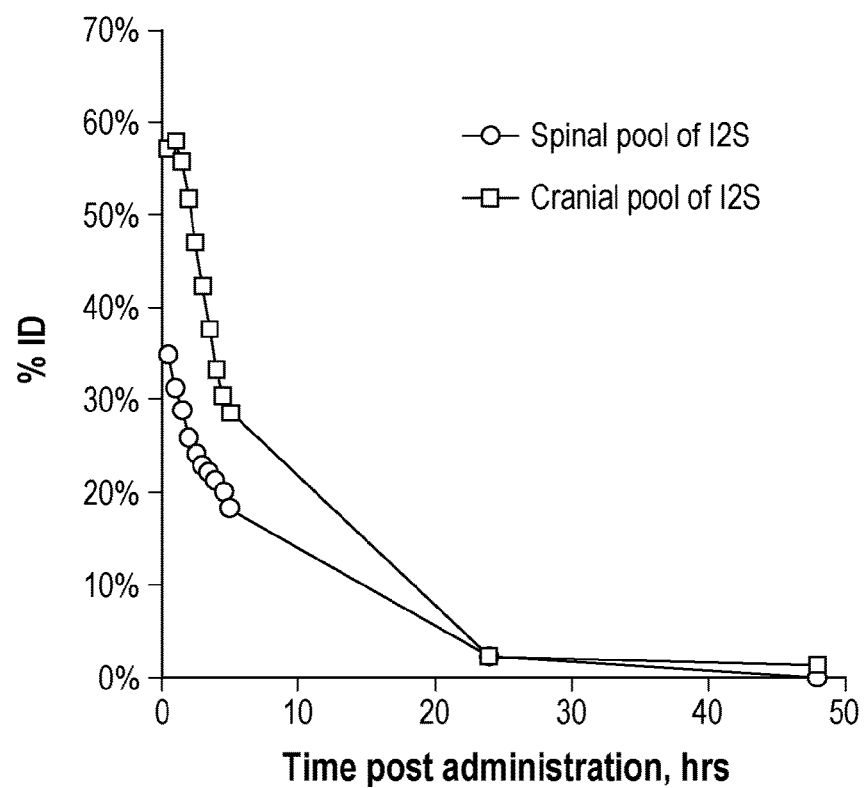

FIG. 41 graphically compares the clearance of iduronate-2-sulfatase (I2S) in the cranial and spinal pools by plotting the amount of I2S in such pools relative to the time following administration.

Figure 42:
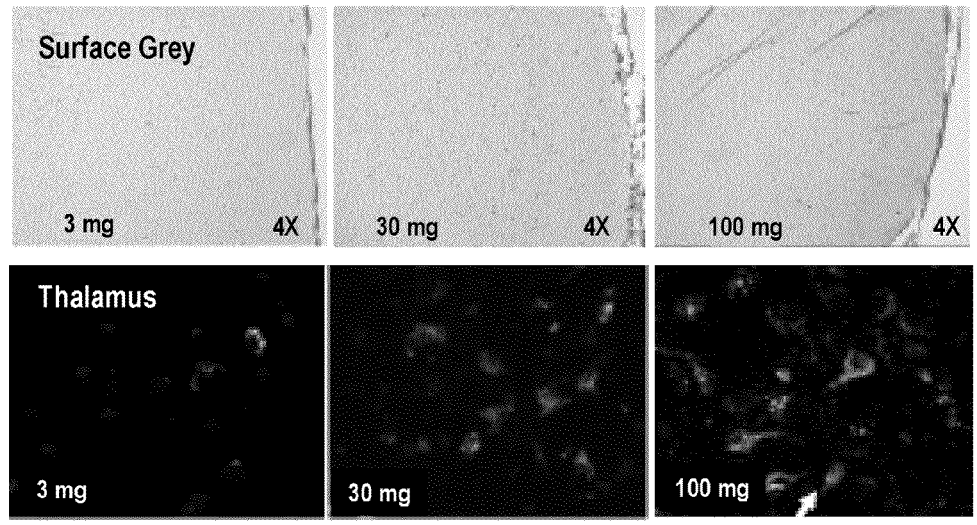

FIG. 42 illustrates the dose dependant gray matter deposition of intrathecally-administered iduronate-2-sulfatase (I2S) to non-human primates over six months. The illustrated staining intensity corresponds with accumulation of iduronate-2-sulfatase in the thalamus. In the present FIG. 42, the nuclei are counterstained by DAPI and appear as blue and protein (I2S) appears as green.

Figure 43:
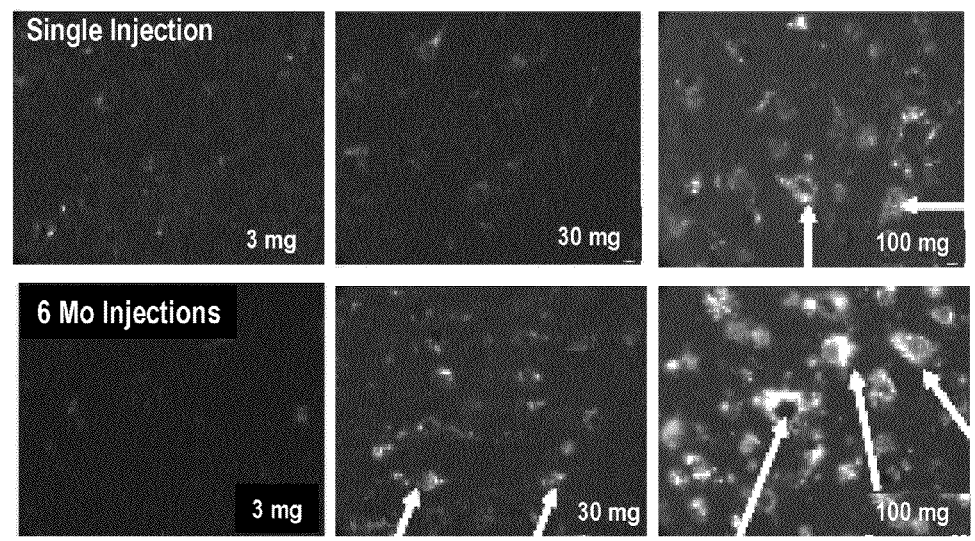

FIG. 43 illustrates the dose dependant accumulation of intrathecally-administered iduronate-2-sulfatase (I2S) to non-human primates following a single injection and following multiple injections over a six month period. The illustrated staining intensity corresponds with accumulation of I2S protein in the cerebral cortex.

Figure 44A:
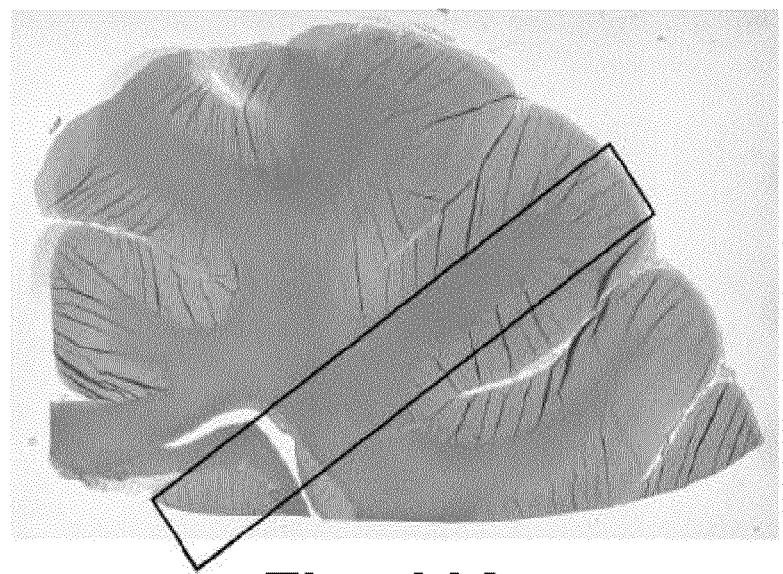
Figure 44B:
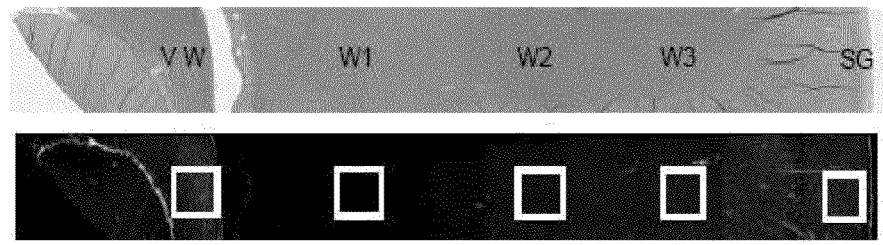

FIG. 44 demonstrates the cellular localization of iduronate-2-sulfatase (I2S) throughout the cerebrum of the non-human primate. FIG. 44A illustrates the cross-sectional view of brain tissue extracted from the cerebrum of the non-human primate, while FIG. 44B illustrates that particular areas of the region corresponding to three areas of white matter tissue (designated W1, W2 and W3), the white matter near the ventricle (VW) and the surface gray matter (SG) tissues of the section identified in FIG. 44A.

Figure 45A:
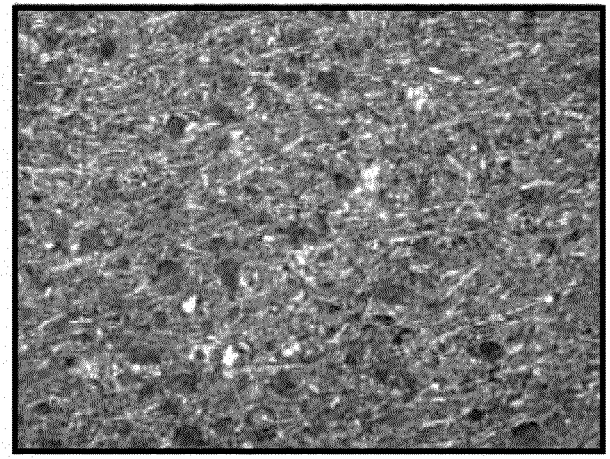
Figure 45B:
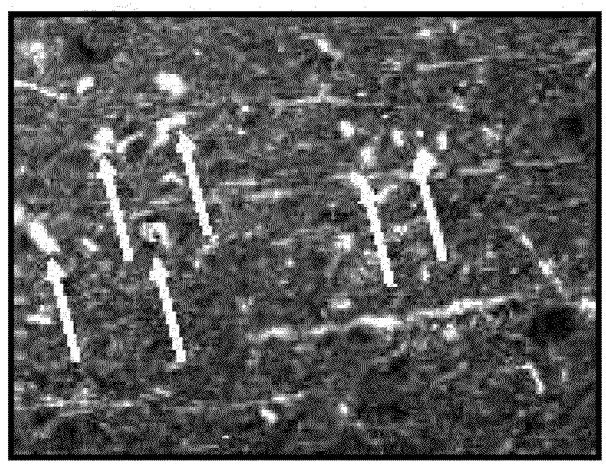
Figure 45C:
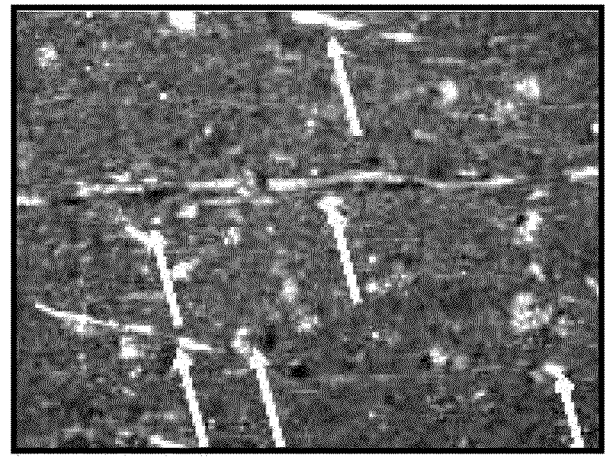
Figure 45D:
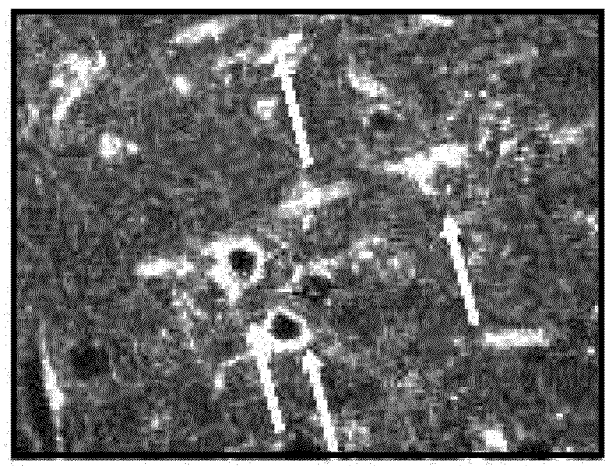

FIG. 45A-D illustrates neuronal and oligodendrocyte uptake and axonal association of intrathecally-administered iduronate-2-sulfatase (I2S) to non-human primates following monthly injections over a six month period. In particular, FIG. 45A, FIG. 45B, FIG. 45C and FIG. 45D are illustrative of a filament staining of the cerebrum tissues of the non-human primate intrathecally administered iduronate-2-sulfatase (I2S) and respectively correspond to the three areas of the white matter (W1, W2 and W3) and the surface gray matter (SG) regions identified in FIG. 44B. FIG. 45A illustrates oligodendrocyte uptake of intrathecally-administered I2S in the white matter (W1) tissues. FIG. 45B and FIG. 45C illustrate oligodendrocyte uptake and axonal association of the intrathecally-administered I2S in the W2 and W3 white matter tissues respectively. FIG. 45D illustrates neuronal uptake of the intrathecally-administered I2S in the surface gray matter (SG) tissues.

Figure 46:
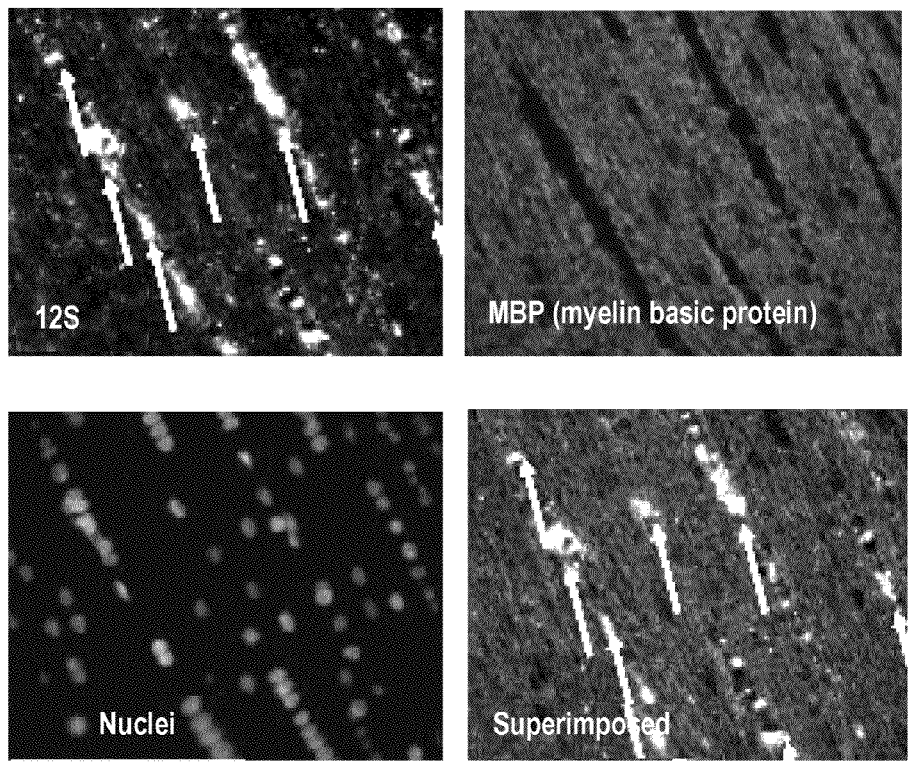

FIG. 46 illustrates the cellular identification of iduronate-2-sulfatase in the white matter near the ventricle (VW) of a non-human primate. As depicted in the superimposed image, the iduronate-2-sulfatase is not associated with myelin (red). In the present FIG. 46, the nuclei are counterstained by DAPI (bottom left) Protein (I2S) appears in the top left box.

Figure 47:
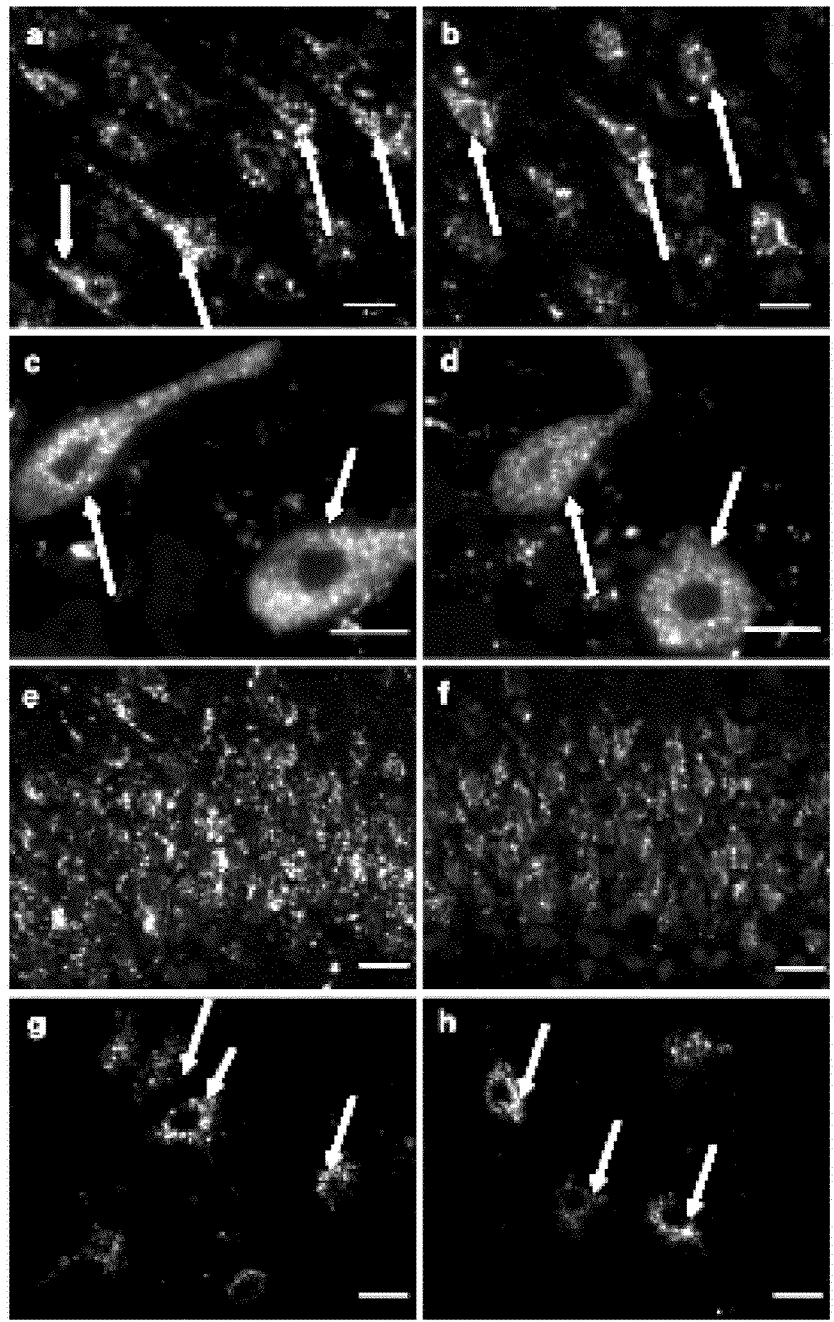

FIG. 47 illustrates staining in the tissues of healthy Beagle dogs that were intracerebroventricularly (ICV) or intrathecally (IT) administered a single injection of iduronate-2-sulfatase (I2S). As depicted in FIGS. 47A-47H, I2S was widely distributed throughout the gray matter of both the IT and ICV groups as determined by immunohistochemistry (IHC). FIGS. 47A and 47B illustrate that in the cerebral cortex, neurons were positive for I2S in all six neuronal layers, from the surface molecular layer to the deep internal layer in both IT and ICV groups. FIGS. 47C and 47D illustrate that in the cerebellar cortex of the IT and ICV groups I2S was detected in neurons, including Purkinje cells. Similarly, FIGS. 47E and 47F illustrate that in both IT and ICV groups a large population of neurons in the hippocampus were positive for I2S. Finally, images g and h demonstrate that I2S-positive neurons were also found in the thalamus and caudate nucleus in the both the IT and ICV groups. In the present FIG. 47, I2S staining is indicated with arrows.

Figure 48:
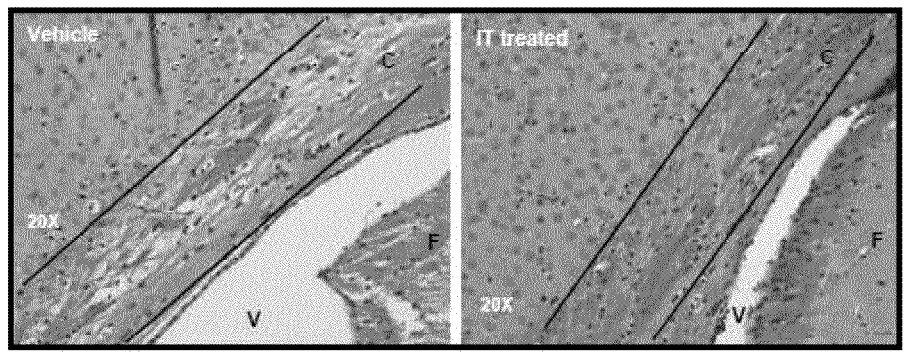

FIG. 48 comparatively illustrates corpus callosum tissues of iduronate-2-sulfatase knock-out (IKO) mice that were either untreated or were administered I2S intrathecally (abbreviation V=vacuole). As depicted, the treated IKO mice exhibited a reduction of cellular vacuolation characteristic of certain lysosomal storage disorders in the corpus callosum and formix tissues of the I2S-treated IKO mouse.

Figure 49A:
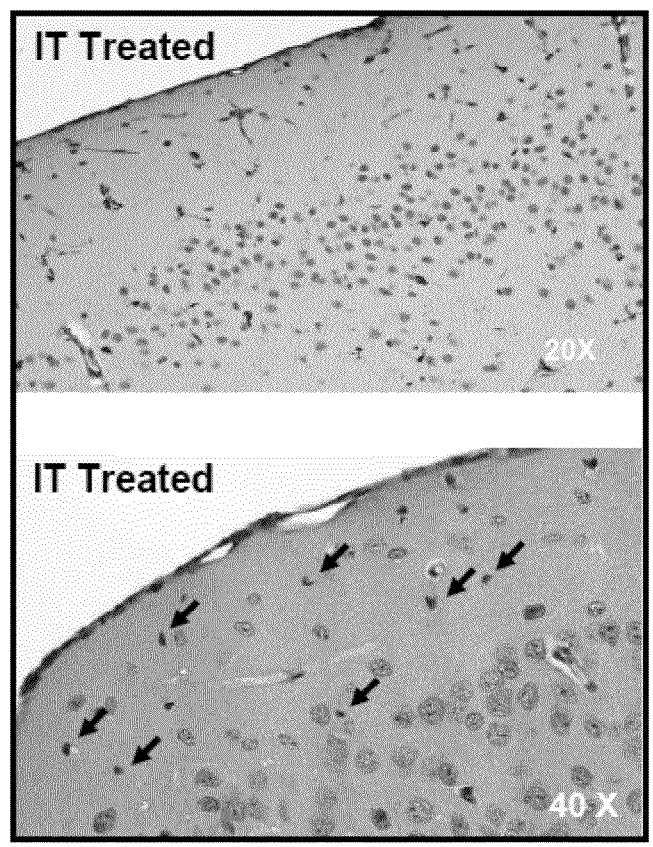
Figure 49B:
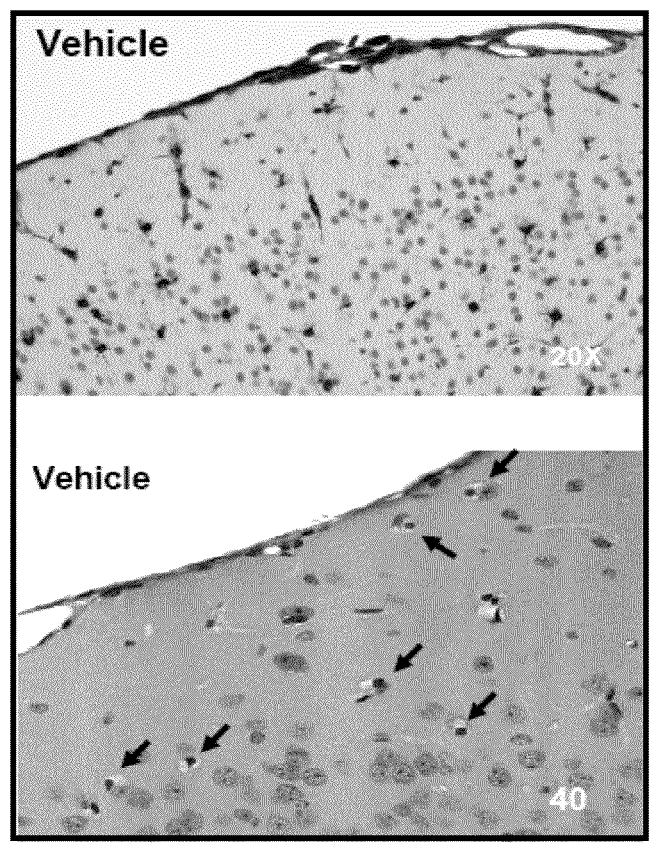

FIG. 49A illustrates a marked reduction in the presence of lysosomal associated membrane protein 1 (LAMP1), a lysosomal disease pathological biomarker, in the surface cerebral cortex tissues of the treated IKO mouse (FIG. 49A) relative to the untreated IKO control mouse (FIG. 49B) under both 20× and 40× magnification.

Figure 50:
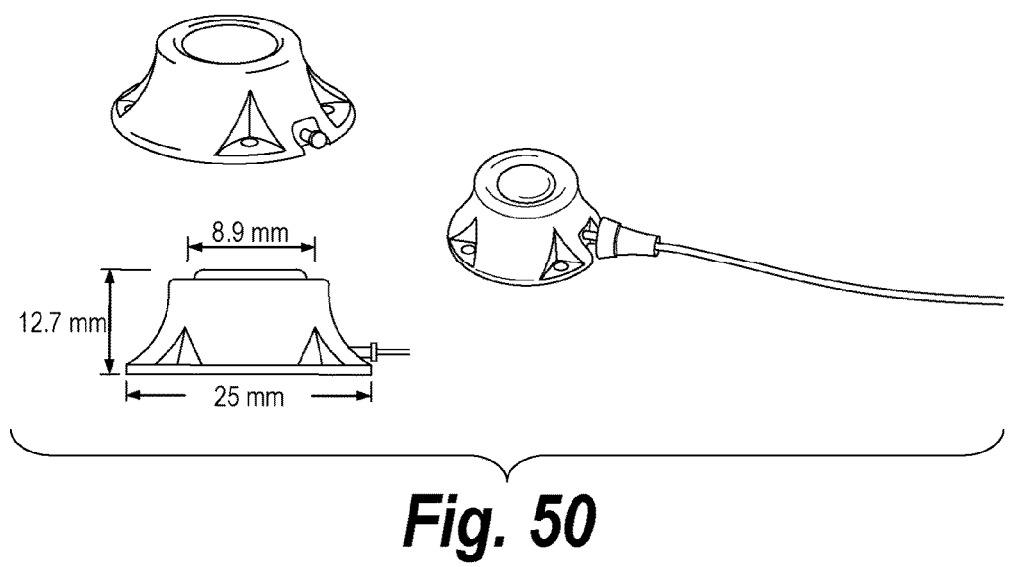

FIG. 50 depicts an exemplary intrathecal drug delivery device (IDDD).

Figure 51:
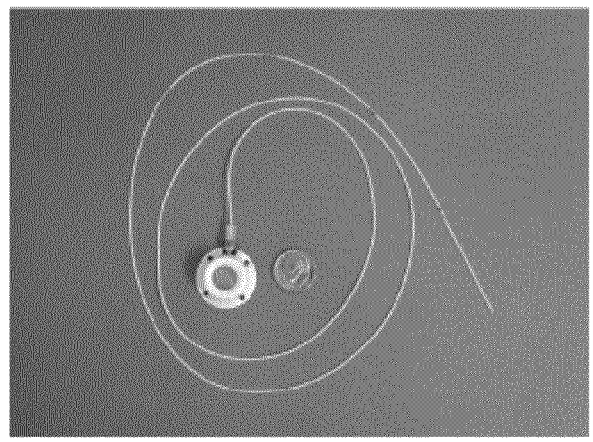

FIG. 51 depicts an exemplary PORT-A-CATH® low profile intrathecal implantable access system.

Figure 52:
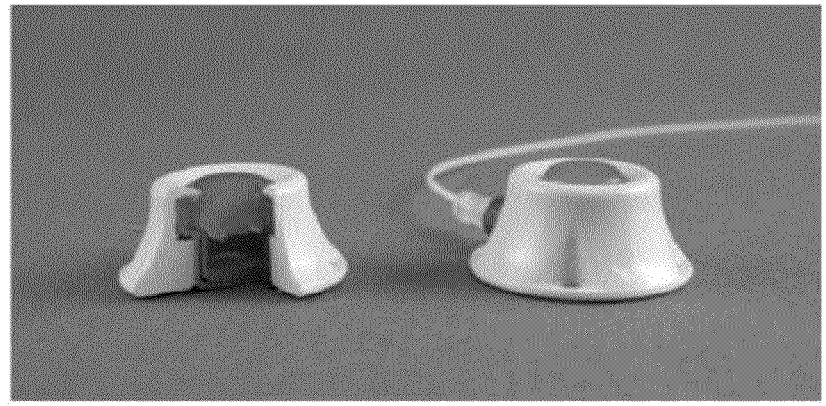

FIG. 52 depicts an exemplary intrathecal drug delivery device (IDDD).

Figure 53:
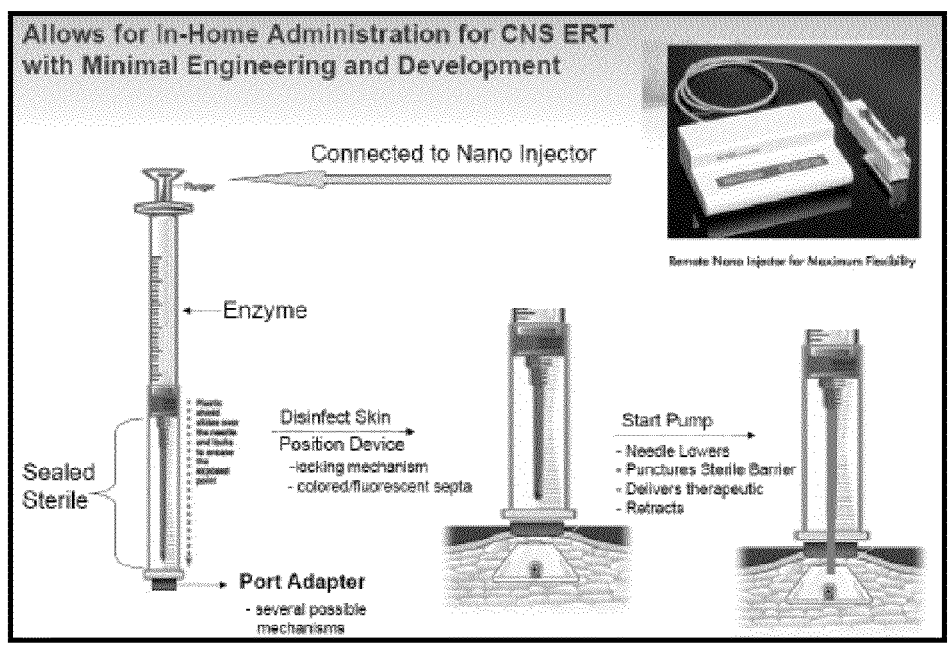

FIG. 53 depicts an exemplary intrathecal drug delivery device (IDDD), which allows for in-home administration for CNS enzyme replacement therapy (ERT).

Figure 54:
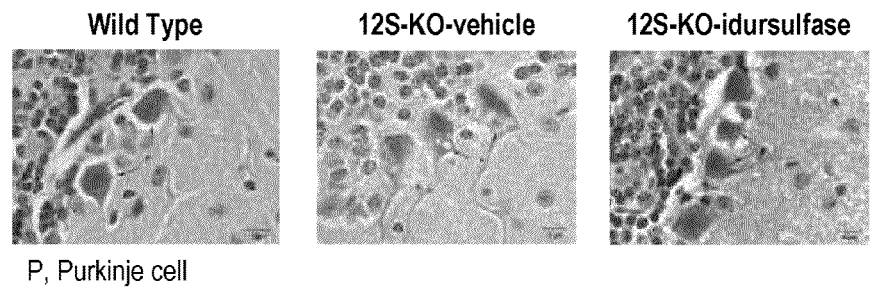

FIG. 54 illustrates exemplary effect of vacuolization after a single intra-cerebral injection of idursulfase in neurons (Purkinje cells).

Figure 55:
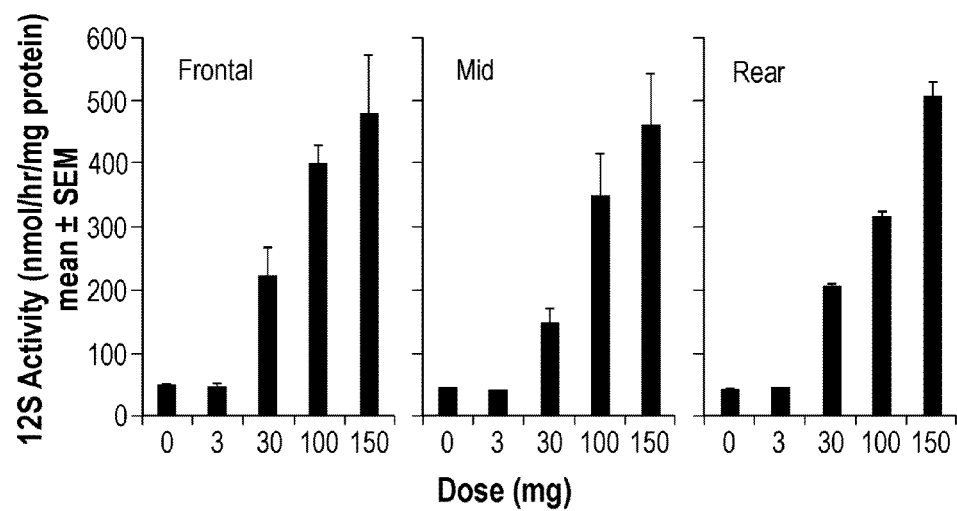

FIG. 55 illustrates exemplary I2S activity in the Brain by dose and region.

Figure 56:
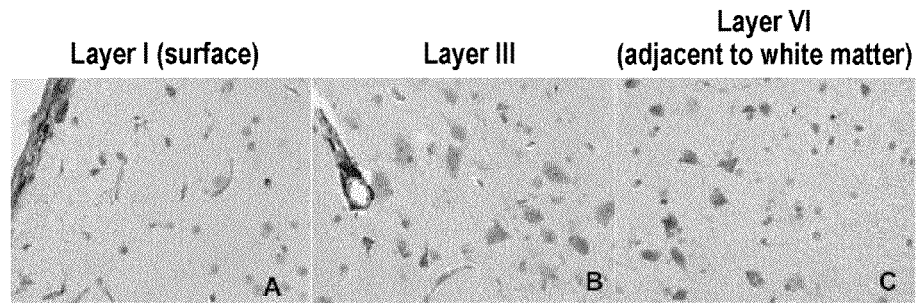

FIG. 56 illustrates exemplary data of immunohistochemical localization of idursulfase at different depths of the cerebral cortex.

Figure 57:
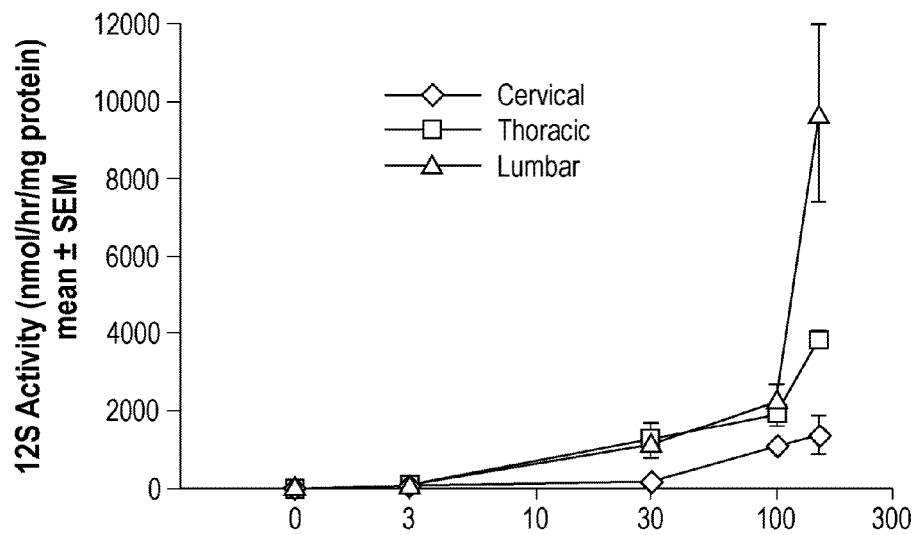

FIG. 57 illustrates exemplary I2S activity in the spinal cord of monkey following intrathecal dosing with idursulfase.

Figure 58:
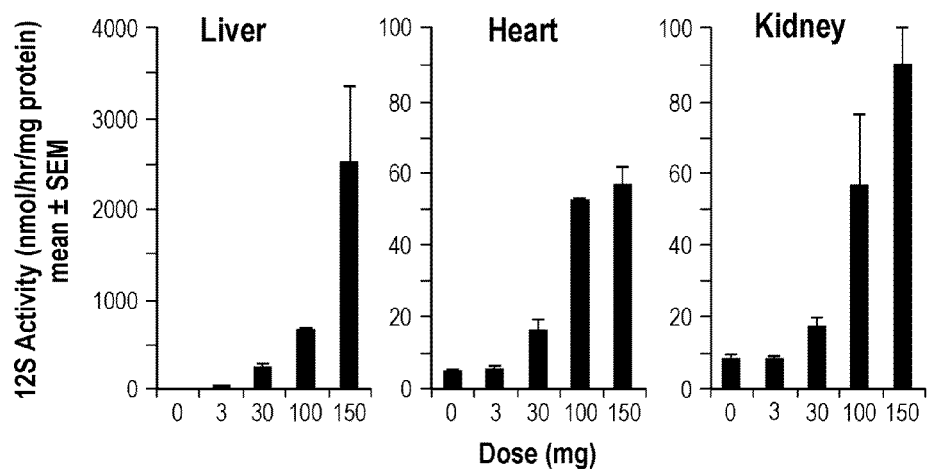

FIG. 58 illustrates exemplary I2S activity in monkey liver, heart and kidney after intrathecal dosing with idursulfase.

Figure 59:
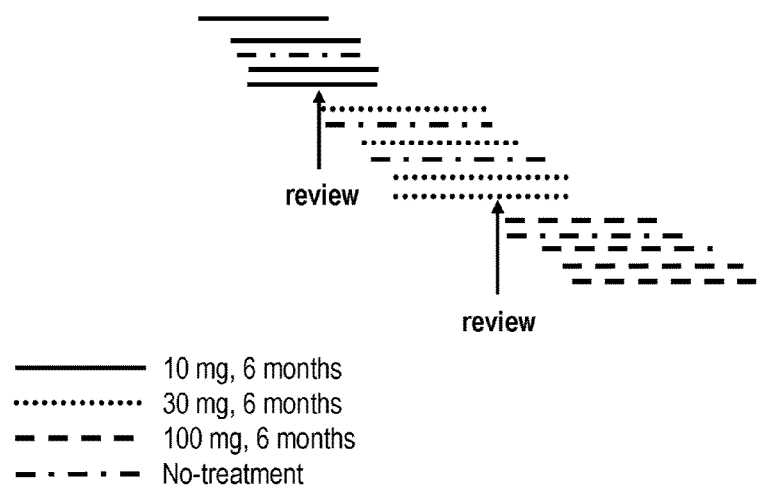

FIG. 59 depicts an exemplary schematic for an escalation Hunter-IT trial program.

Figure 60:
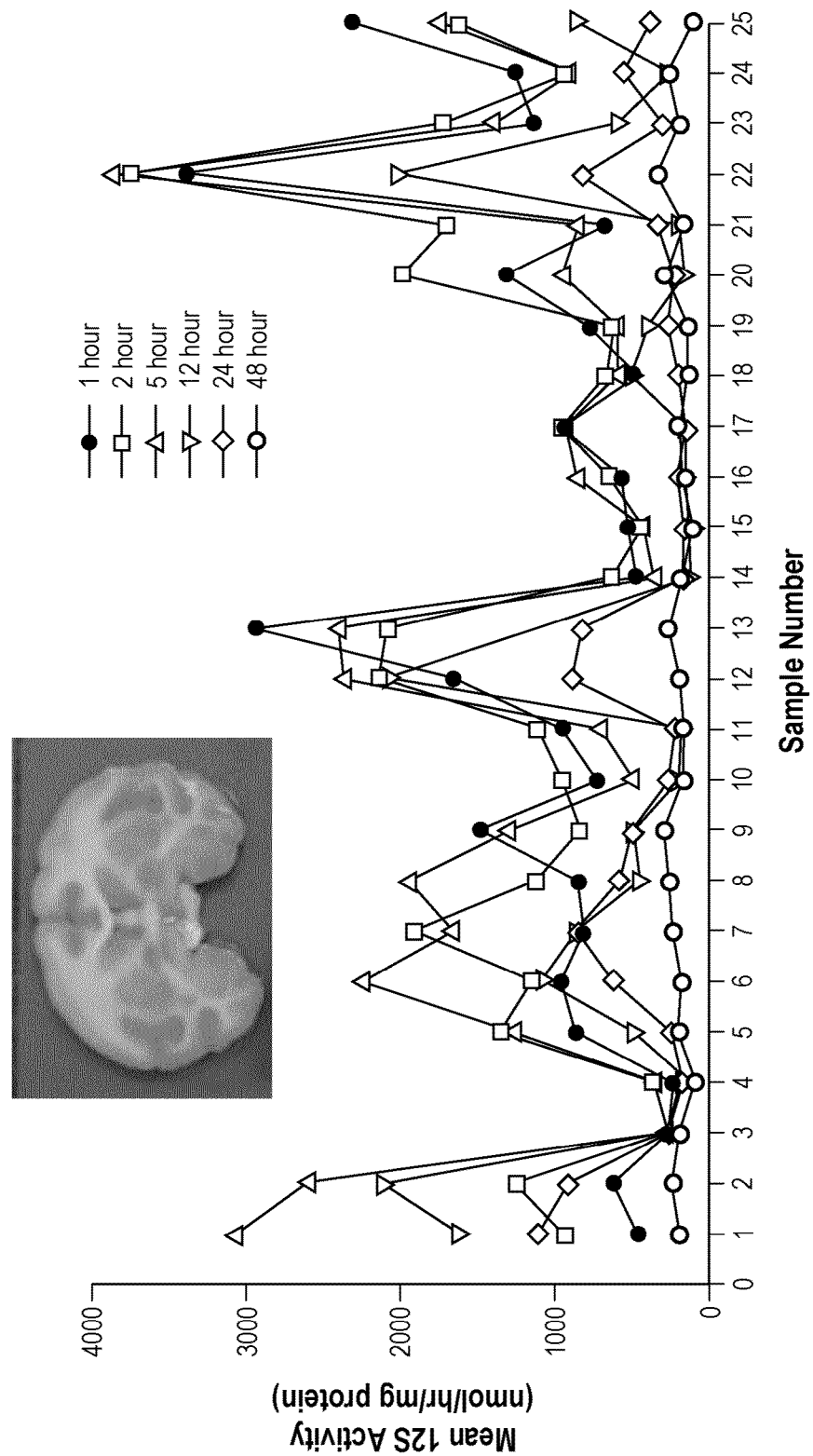

FIG. 60 illustrates exemplary measurements of I2S concentrations in various sections of brain tissue after 30 mg dose. Different plots correspond to different times of measurement.

Figure 61:
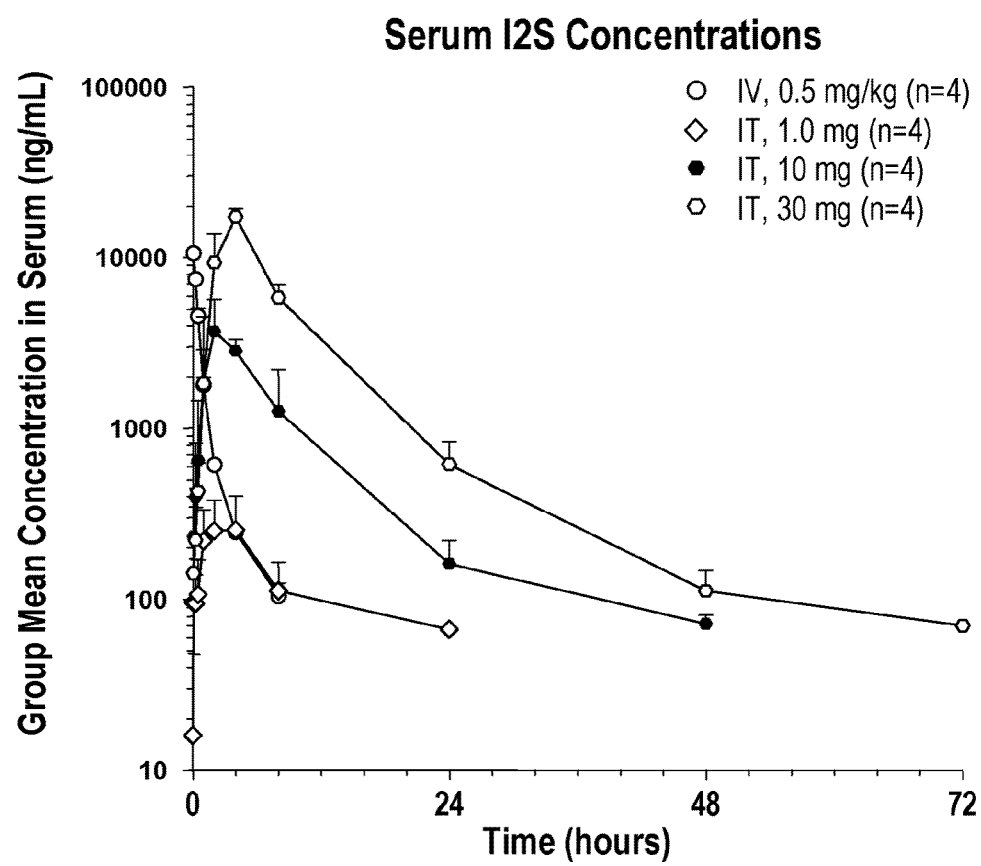

FIG. 61 illustrates exemplary measurements of I2S concentration after administration over time via various routes of administration for various product concentrations.

Figure 62:
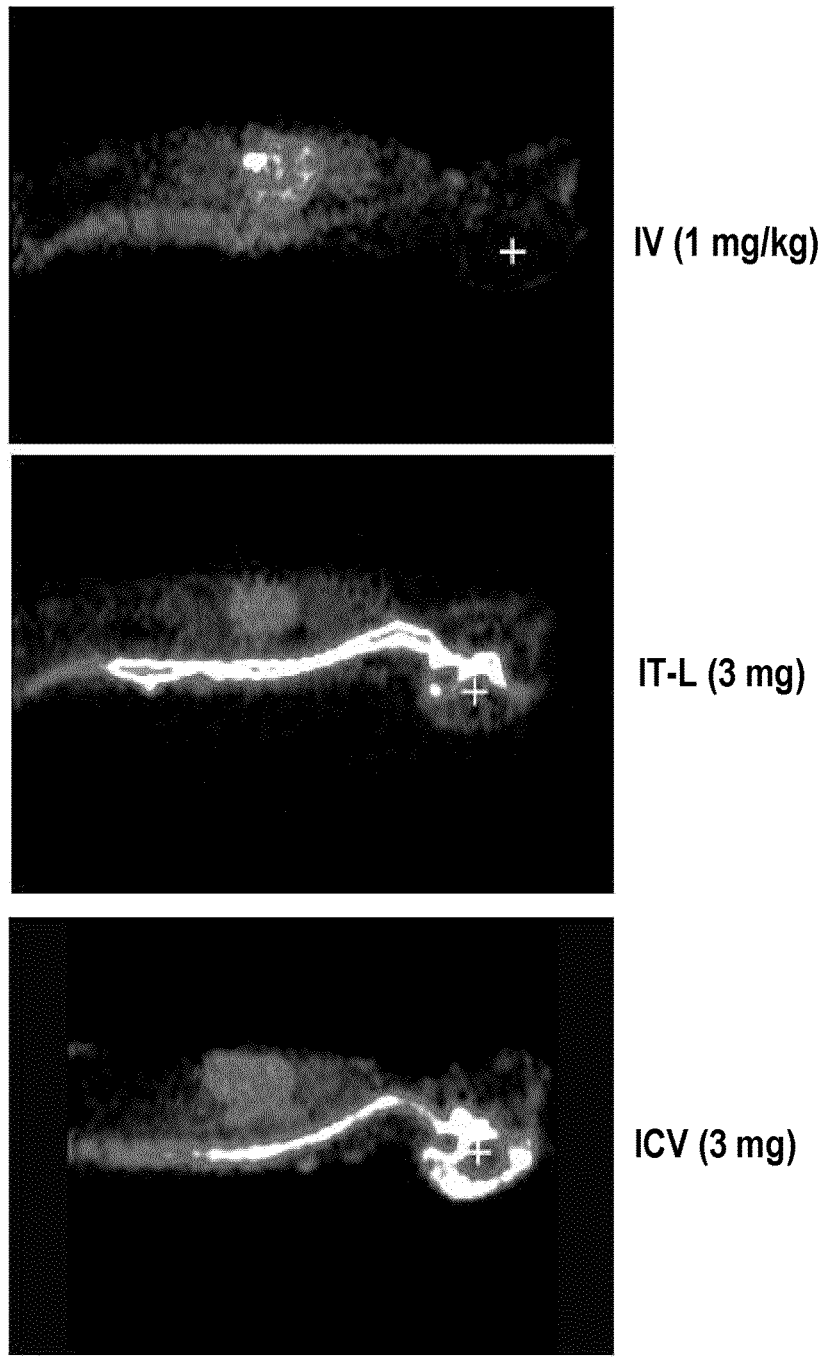

FIG. 62 is an exemplary illustration of PET imaging of $^{124}$I-labeled idursulfase-IT in cynomolgus monkeys at t=5 hours following IV, IT-L, or ICV dosing.

Figure 63:
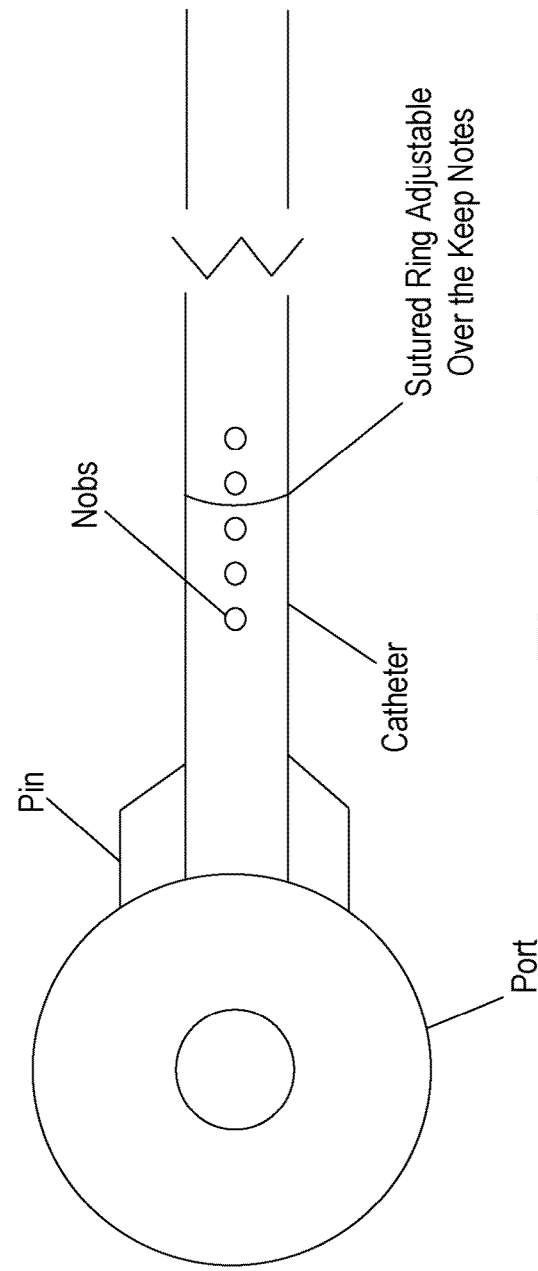

FIG. 63 illustrates and exemplary diagram of an intrathecal drug delivery device IDDD.

Figure 64A:
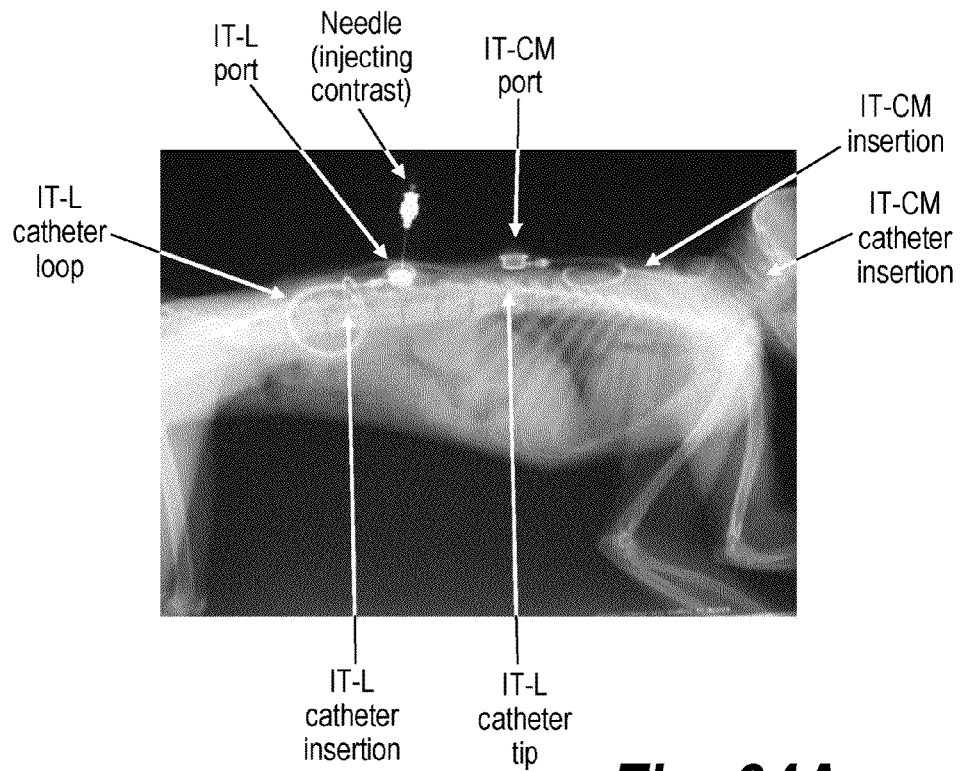
Figure 64B:
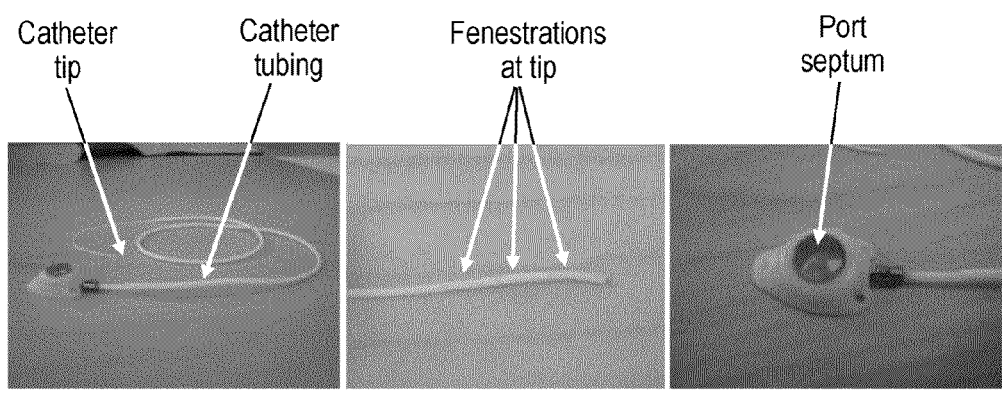
Figure 64C:
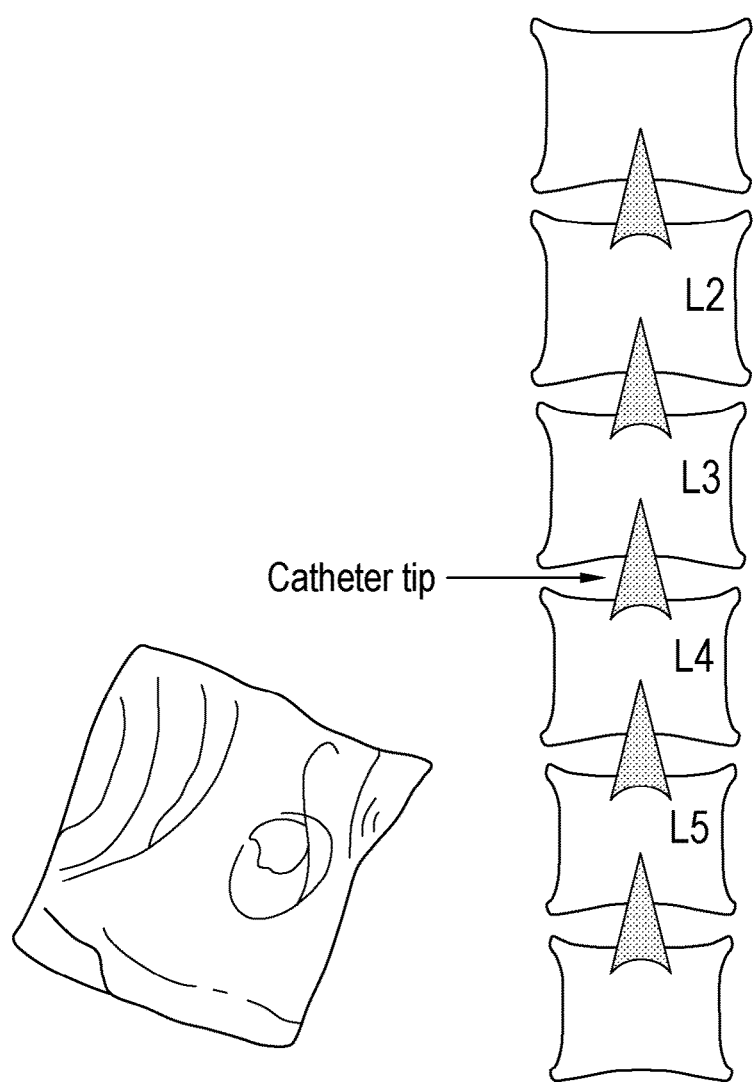

FIGS. 64A and 64B depict various features of an IDDD both within a subject's body (FIG. 64A) and displayed on a flat surface (FIG. 64B). FIG. 64C displays where the catheter tip may be inserted between the laminae of the lumbar vertebrae.

DEFINITIONS

In order for the present invention to be more readily understood, certain terms are first defined below. Additional definitions for the following terms and other terms are set forth throughout the specification.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" is meant the prevention, reduction or palliation of a state, or improvement of the state of a subject. Amelioration includes, but does not require complete recovery or complete prevention of a disease condition. In some embodiments, amelioration includes increasing levels of relevant protein or its activity that is deficient in relevant disease tissues.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Bulking agent: As used herein, the term "bulking agent" refers to a compound which adds mass to the lyophilized mixture and contributes to the physical structure of the lyophilized cake (e.g., facilitates the production of an essentially uniform lyophilized cake which maintains an open pore structure). Exemplary bulking agents include mannitol, glycine, sodium chloride, hydroxyethyl starch, lactose, sucrose, trehalose, polyethylene glycol and dextran.

Cation-independent mannose-6-phosphate receptor (CI-MPR): As used herein, the term "cation-independent mannose-6-phosphate receptor (CI-MPR)" refers to a cellular receptor that binds mannose-6-phosphate (M6P) tags on acid hydrolase precursors in the Golgi apparatus that are destined for transport to the lysosome. In addition to mannose-6-phosphates, the CI-MPR also binds other proteins including IGF-II. The CI-MPR is also known as "M6P/IGF-II receptor," "CI-MPR/IGF-II receptor," "IGF-II receptor" or "IGF2 Receptor." These terms and abbreviations thereof are used interchangeably herein.

Concurrent immunosuppressant therapy: As used herein, the term "concurrent immunosuppressant therapy" includes any immunosuppressant therapy used as pre-treatment, preconditioning or in parallel to a treatment method.

Diluent: As used herein, the term "diluent" refers to a pharmaceutically acceptable (e.g., safe and non-toxic for administration to a human) diluting substance useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

Dosage form: As used herein, the terms "dosage form" and "unit dosage form" refer to a physically discrete unit of a therapeutic protein for the patient to be treated. Each unit contains a predetermined quantity of active material calculated to produce the desired therapeutic effect. It will be understood, however, that the total dosage of the composition will be decided by the attending physician within the scope of sound medical judgment.

Enzyme replacement therapy (ERT): As used herein, the term "enzyme replacement therapy (ERT)" refers to any therapeutic strategy that corrects an enzyme deficiency by providing the missing enzyme. In some embodiments, the missing enzyme is provided by intrathecal administration. In some embodiments, the missing enzyme is provided by infusing into bloodsteam. Once administered, enzyme is taken up by cells and transported to the lysosome, where the enzyme acts to eliminate material that has accumulated in the lysosomes due to the enzyme deficiency. Typically, for lysosomal enzyme replacement therapy to be effective, the therapeutic enzyme is delivered to lysosomes in the appropriate cells in target tissues where the storage defect is manifest.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of lysosomal storage disease as the individual being treated, who is about the same age as the individual being treated (to ensure that the stages of the disease in the treated individual and the control individual(s) are comparable).

Individual, subject, patient: As used herein, the terms "subject," "individual" or "patient" refer to a human or a non-human mammalian subject. The individual (also referred to as "patient" or "subject") being treated is an individual (fetus, infant, child, adolescent, or adult human) suffering from a diseasE.

Intrathecal administration: As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine.

Linker: As used herein, the term "linker" refers to, in a fusion protein, an amino acid sequence other than that appearing at a particular position in the natural protein and is generally designed to be flexible or to interpose a structure, such as an a-helix, between two protein moieties. A linker is also referred to as a spacer.

Lyoprotectant: As used herein, the term "lyoprotectant" refers to a molecule that prevents or reduces chemical and/or physical instability of a protein or other substance upon lyophilization and subsequent storage. Exemplary lyoprotectants include sugars such as sucrose or trehalose; an amino acid such as monosodium glutamate or histidine; a methylamine such as betaine; a lyotropic salt such as magnesium sulfate: a polyol such as trihydric or higher sugar alcohols, e.g. glycerin, erythritol, glycerol, arabitol, xylitol, sorbitol, and mannitol; propylene glycol; polyethylene glycol; Pluronics; and combinations thereof. In some embodiments, a lyoprotectant is a non-reducing sugar, such as trehalose or sucrose.

Lysosomal enzyme: As used herein, the term "lysosomal enzyme" refers to any enzyme that is capable of reducing accumulated materials in mammalian lysosomes or that can rescue or ameliorate one or more lysosomal storage disease symptoms. Lysosomal enzymes suitable for the invention include both wild-type or modified lysosomal enzymes and can be produced using recombinant and synthetic methods or purified from nature sources. Exemplary lysosomal enzymes are listed in Table 1.

Lysosomal enzyme deficiency: As used herein, "lysosomal enzyme deficiency" refers to a group of genetic disorders that result from deficiency in at least one of the enzymes that are required to break macromolecules (e.g., enzyme substartes) down to peptides, amino acids, monosaccharides, nucleic acids and fatty acids in lysosomes. As a result, individuals suffering from lysosomal enzyme deficiencies have accumulated materials in various tissues (e.g., CNS, liver, spleen, gut, blood vessel walls and other organs).

Lysosomal Storage Disease: As used herein, the term "lysosomal storage disease" refers to any disease resulting from the deficiency of one or more lysosomal enzymes necessary for metabolizing natural macromolecules. These diseases typically result in the accumulation of un-degraded molecules in the lysosomes, resulting in increased numbers of storage granules (also termed storage vesicles). These diseases and various examples are described in more detail below.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Replacement enzyme: As used herein, the term "replacement enzyme" refers to any enzyme that can act to replace at least in part the deficient or missing enzyme in a disease to be treated. In some embodiments, the term "replacement enzyme" refers to any enzyme that can act to replace at least in part the deficient or missing lysosomal enzyme in a lysosomal storage disease to be treated. In some emebodiments, a replacement enzyme is capable of reducing accumulated materials in mammalian lysosomes or that can rescue or ameliorate one or more lysosomal storage disease symptoms. Replacement enzymes suitable for the invention include both wild-type or modified lysosomal enzymes and can be produced using recombinant and synthetic methods or purified from nature sources. A replacement enzyme can be a recombinant, synthetic, gene-activated or natural enzyme.

Soluble: As used herein, the term "soluble" refers to the ability of a therapeutic agent to form a homogenous solution. In some embodiments, the solubility of the therapeutic agent in the solution into which it is administered and by which it is transported to the target site of action (e.g., the cells and tissues of the brain) is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts). In some embodiments, the pharmaceutical compositions are formulated such that calcium salts are excluded from such compositions. In some embodiments, therapeutic agents in accordance with the present invention are soluble in its corresponding pharmaceutical composition. It will be appreciated that, while isotonic solutions are generally preferred for parenterally administered drugs, the use of isotonic solutions may limit adequate solubility for some therapeutic agents and, in particular some proteins and/or enzymes. Slightly hypertonic solutions (e.g., up to 175 mM sodium chloride in 5 mM sodium phosphate at pH 7.0) and sugar-containing solutions (e.g., up to 2% sucrose in 5 mM sodium phosphate at pH 7.0) have been demonstrated to be well tolerated in monkeys. For example, the most common approved CNS bolus formulation composition is saline (150 mM NaCl in water).

Stability: As used herein, the term "stable" refers to the ability of the therapeutic agent (e.g., a recombinant enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In general, pharmaceutical compositions described herein have been formulated such that they are capable of stabilizing, or alternatively slowing or preventing the degradation, of one or more therapeutic agents formulated therewith (e.g., recombinant proteins). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measure by formation of high molecular weight (HMW) aggregates, loss of enzyme activity, generation of peptide fragments and shift of charge profiles.

Subject: As used herein, the term "subject" means any mammal, including humans. In certain embodiments of the present invention the subject is an adult, an adolescent or an infant. Also contemplated by the present invention are the administration of the pharmaceutical compositions and/or performance of the methods of treatment in-utero.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.,* 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.,* 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Synthetic CSF: As used herein, the term "synthetic CSF" refers to a solution that has pH, electrolyte composition, glucose content and osmalarity consistent with the cerebrospinal fluid. Synthetic CSF is also referred to as artifical CSF. In some embodiments, synthetic CSF is an Elliott's B solution.

Suitable for CNS delivery: As used herein, the phrase "suitable for CNS delivery" or "suitable for intrathecal delivery" as it relates to the pharmaceutical compositions of the present invention generally refers to the stability, tolerability, and solubility properties of such compositions, as well as the ability of such compositions to deliver an effective amount of the therapeutic agent contained therein to the targeted site of delivery (e.g., the CSF or the brain).

Target tissues: As used herein, the term "target tissues" refers to any tissue that is affected by the lysosomal storage disease to be treated or any tissue in which the deficient lysosomal enzyme is normally expressed. In some embodiments, target tissues include those tissues in which there is a detectable or abnormally high amount of enzyme substrate, for example stored in the cellular lysosomes of the tissue, in patients suffering from or susceptible to the lysosomal storage disease. In some embodiments, target tissues include those tissues that display disease-associated pathology, symptom, or feature. In some embodiments, target tissues include those tissues in which the deficient lysosomal enzyme is normally expressed at an elevated level. As used herein, a target tissue may be a brain target tissue, a spinal cord target tissue an/or a peripheral target tissue. Exemplary target tissues are described in detail below.

Therapeutic moiety: As used herein, the term "therapeutic moiety" refers to a portion of a molecule that renders the therapeutic effect of the molecule. In some embodiments, a therapeutic moiety is a polypeptide having therapeutic activity.

Therapeutically effective amount: As used herein, the term "therapeutically effective amount" refers to an amount of a therapeutic protein (e.g., replacement enzyme) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Tolerable: As used herein, the terms "tolerable" and "tolerability" refer to the ability of the pharmaceutical compositions of the present invention to not elicit an adverse reaction in the subject to whom such composition is administered, or alternatively not to elicit a serious adverse reaction in the subject to whom such composition is administered. In some embodiments, the pharmaceutical compositions of the present invention are well tolerated by the subject to whom such compositions is administered.

Treatment: As used herein, the term "treatment" (also "treat" or "treating") refers to any administration of a therapeutic protein (e.g., lysosomal enzyme) that partially or completely alleviates, ameliorates, relieves, inhibits, delays onset of, reduces severity of and/or reduces incidence of one or more symptoms or features of a particular disease, disorder, and/or condition (e.g., Hunters syndrome, Sanfilippo B syndrome). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

DETAILED DESCRIPTION OF THE INVENTION

The present invention provides, among other things, improved methods and compositions for effective direct delivery of a therapeutic agent to the central nervous system (CNS). As discussed above, the present invention is based on unexpected discovery that a replacement enzyme (e.g., an I2S protein) for a lysososmal storage disease (e.g., Hunters Syndrome) can be directly introduced into the cerebrospinal fluid (CSF) of a subject in need of treatment at a high concentration without inducing substantial adverse effects in the subject. More surprisingly, the present inventors found that the replacement enzyme may be delivered in a simple saline or buffer-based formulation, without using synthetic CSF. Even more unexpectedly, intrathecal delivery according to the present invention does not result in substantial adverse effects, such as severe immune response, in the subject. Therefore, in some embodiments, intrathecal delivery according to the present invention may be used in absence of concurrent immunosuppressant therapy (e.g., without induction of immune tolerance by pre-treatment or pre-conditioning).

In some embodiments, intrathecal delivery according to the present invention permits efficient diffusion across various brain tissues resulting in effective delivery of the replacement enzyme in various target brain tissues in surface, shallow and/or deep brain regions. In some embodiments, intrathecal delivery according to the present invention resulted in sufficient amount of replacement enzymes entering the peripheral circulation. As a result, in some cases, intrathecal delivery according to the present invention resulted in delivery of the replacement enzyme in peripheral tissues, such as liver, heart, spleen and kidney. This discovery is unexpected and can be particular useful for the treatment of lysosomal storage diseases that have both CNS and peripheral components, which would typically require both regular intrathecal administration and intravenous administration. It is contemplated that intrathecal delivery according to the present invention may allow reduced dosing and/or frequency of iv injection without compromising therapeutic effects in treating peripheral symptoms.

The present invention provides various unexpected and beneficial features that allow efficient and convenient delivery of replacement enzymes to various brain target tissues, resulting in effective treatment of lysosomal storage diseases that have CNS indications.

Various aspects of the invention are described in detail in the following sections. The use of sections is not meant to limit the invention. Each section can apply to any aspect of the invention. In this application, the use of "or" means "and/or" unless stated otherwise.

Replacement Enzymes

Iduronate-2-sulfatase (I2S) Protein

In some embodiments, inventive methods and compositions provided by the present invention are used to deliver an Iduronate-2-sulfatase (I2S) protein to the CNS for treatment of Hunters Syndrome. A suitable I2S protein can be any molecule or a portion of a molecule that can substitute for naturally-occurring Iduronate-2-sulfatase (I2S) protein activity or rescue one or more phenotypes or symptoms associated with I2S-deficiency. In some embodiments, a replacement enzyme suitable for the invention is a polypeptide having an N-terminus and a C-terminus and an amino acid sequence substantially similar or identical to mature human I2S protein.

Typically, the human I2S protein is produced as a precursor form. The precursor form of human I2S contains a signal peptide (amino acid residues 1-25 of the full length precursor), a pro-peptide (amino acid residues 26-33 of the full length precursor), and a chain (residues 34-550 of the full length precursor) that may be further processed into the 42 kDa chain (residues 34-455 of the full length precursor) and the 14 kDa chain (residues 446-550 of the full length precursor). Typically, the precursor form is also referred to as full-length precursor or full-length I2S protein, which contains 550 amino acids. The amino acid sequences of the mature form (SEQ ID NO:1) having the signal peptide removed and full-length precursor (SEQ ID NO:2) of a typical wild-type or naturally-occurring human I2S protein are shown in Table 1.

TABLE 1

Human Iduronate-2-sulfatase

Mature Form SETQANSTTDALNVLLIIVDDLRPSLGCYGDKLVRSPNIDQLASHSLLFQNAFA
QQAVCAPSRVSFLTGRRPDTTRLYDFNSYWRVHAGNFSTIPQYFKENGYVTMSV
GKVFHPGISSNHTDDSPYSWSFPPYHPSSEKYENTKTCRGPDGELHANLLCPVD
VLDVPEGTLPDKQSTEQAIQLLEKMKTSASPFFLAVGYHKPHIPFRYPKEFQKL
YPLENITLAPDPEVPDGLPPVAYNPWMDIRQREDVQALNISVPYGPIPVDFQRK
IRQSYFASVSYLDTQVGRLLSALDDLQLANSTIIAFTSDHGWALGEHGEWAKYS
NFDVATHVPLIFYVPGRTASLPEAGEKLFPYLDPFDSASQLMEPGRQSMDLVEL
VSLFPTLAGLAGLQVPPRCPVPSFHVELCREGKNLLKHFRFRDLEEDPYLPGNP
RELIAYSQYPRPSDIPQWNSDKPSLKDIKIMGYSIRTIDYRYTVWVGFNPDEFL
ANFSDIHAGELYFVDSDPLQDHNMYNDSQGGDLFQLLMP (SEQ ID NO: 1)

Full-Length MPPPRTGRGLLWLGLVLSSVCVALGSETQANSTTDALNVLLIIVDDLRPSLGCY
Precursor GDKLVRSPNIDQLASHSLLFQNAFAQQAVCAPSRVSFLTGRRPDTTRLYDFNSY
WRVHAGNFSTIPQYFKENGYVTMSVGKVFHPGISSNHTDDSPYSWSFPPYHPSS
EKYENTKTCRGPDGELHANLLCPVDVLDVPEGTLPDKQSTEQAIQLLEKMKTSA
SPFFLAVGYHKPHIPFRYPKEFQKLYPLENITLAPDPEVPDGLPPVAYNPWMDI
RQREDVQALNISVPYGPIPVDFQRKIRQSYFASVSYLDTQVGRLLSALDDLQLA
NSTIIAFTSDHGWALGEHGEWAKYSNFDVATHVPLIFYVPGRTASLPEAGEKLF
PYLDPFDSASQLMEPGRQSMDLVELVSLFPTLAGLAGLQVPPRCPVPSFHVELC
REGKNLLKHFRFRDLEEDPYLPGNPRELIAYSQYPRPSDIPQWNSDKPSLKDIK TABLE 1-continued Human Iduronate-2-sulfatase

IMGYSIRTIDYRYTVWVGFNPDEFLANFSDIHAGELYFVDSDPLQDHNMYNDSQ
GGDLFQLLMP(SEQ ID NO: 2)

Thus, in some embodiments, a replacement enzyme suitable for the present invention is mature human I2S protein (SEQ ID NO:1). In some embodiments, a suitable replacement enzyme may be a homologue or an analogue of mature human I2S protein. For example, a homologue or an analogue of mature human I2S protein may be a modified mature human I2S protein containing one or more amino acid substitutions, deletions, and/or insertions as compared to a wild-type or naturally-occurring I2S protein (e.g., SEQ ID NO:1), while retaining substantial I2S protein activity. Thus, in some embodiments, a replacement enzyme suitable for the present invention is substantially homologous to mature human I2S protein (SEQ ID NO:1). In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a replacement enzyme suitable for the present invention is substantially identical to mature human I2S protein (SEQ ID NO:1). In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1. In some embodiments, a replacement enzyme suitable for the present invention contains a fragment or a portion of mature human I2S protein.

Alternatively, a replacement enzyme suitable for the present invention is full-length I2S protein. In some embodiments, a suitable replacement enzyme may be a homologue or an analogue of full-length human I2S protein. For example, a homologue or an analogue of full-length human I2S protein may be a modified full-length human I2S protein containing one or more amino acid substitutions, deletions, and/or insertions as compared to a wild-type or naturally-occurring full-length I2S protein (e.g., SEQ ID NO:2), while retaining substantial I2S protein activity. Thus, in some embodiments, a replacement enzyme suitable for the present invention is substantially homologous to full-length human I2S protein (SEQ ID NO:2). In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2. In some embodiments, a replacement enzyme suitable for the present invention is substantially identical to SEQ ID NO:2. In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2. In some embodiments, a replacement enzyme suitable for the present invention contains a fragment or a portion of full-length human I2S protein. As used herein, a full-length I2S protein typically contains signal peptide sequence.

Other Lysosomal Storage Diseases and Replacement Enzymes

It is contemplated that inventive methods and compositions according to the present invention can be used to treat other lysosomal storage diseases, in particular those lysosomal storage diseases having CNS etiology and/or symptoms, including, but are not limited to, aspartylglucosaminuria, cholesterol ester storage disease, Wolman disease, cystinosis, Danon disease, Fabry disease, Farber lipogranulomatosis, Farber disease, fucosidosis, galactosialidosis types I/II, Gaucher disease types I/II/III, globoid cell leukodystrophy, Krabbe disease, glycogen storage disease II, Pompe disease, GM1-gangliosidosis types I/II/III, GM2-gangliosidosis type I, Tay Sachs disease, GM2-gangliosidosis type II, Sandhoff disease, GM2-gangliosidosis, α-mannosidosis types I/II, .beta.-mannosidosis, metachromatic leukodystrophy, mucolipidosis type I, sialidosis types I/II, mucolipidosis types II/III, I-cell disease, mucolipidosis type IIIC pseudo-Hurler polydystrophy, mucopolysaccharidosis type I, mucopolysaccharidosis type II, mucopolysaccharidosis type IIIA, Sanfilippo syndrome, mucopolysaccharidosis type IIIB, mucopolysaccharidosis type IIIC, mucopolysaccharidosis type IIID, mucopolysaccharidosis type IVA, Morquio syndrome, mucopolysaccharidosis type IVB, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, CLN2 Batten diseae, Niemann-Pick disease types A/B, Niemann-Pick disease type C1, Niemann-Pick disease type C2, pycnodysostosis, Schindler disease types I/II, Gaucher disease and sialic acid storage disease.

A detailed review of the genetic etiology, clinical manifestations, and molecular biology of the lysosomal storage diseases are detailed in Scriver et al., eds., The Metabolic and Molecular Basis of Inherited Disease, 7.sup.th Ed., Vol. II, McGraw Hill, (1995). Thus, the enzymes deficient in the above diseases are known to those of skill in the art, some of these are exemplified in Table 2 below:

TABLE 2

| Disease Name | Enzyme Deficiency | Substance Stored |
| --- | --- | --- |
| Pompe Disease | Acid-α1, 4-Glucosidase | Glycogen α1-4 linked Oligosaccharides |
| GM1 Gangliodsidosis | β-Galactosidase | GM$_1$ Gangliosides |
| Tay-Sachs Disease | β-Hexosaminidase A | GM$_2$ Ganglioside |
| GM2 Gangliosidosis: AB Variant | GM$_2$ Activator Protein | GM$_2$ Ganglioside |
| Sandhoff Disease | β-Hexosaminidase A & B | GM$_2$ Ganglioside |
| Fabry Disease | α-Galactosidase A | Globosides |
| Gaucher Disease | Glucocerebrosidase | Glucosylceramide |
| Metachromatic Leukodystrophy | Arylsulfatase A | Sulphatides |
| Krabbe Disease | Galactosylceramidase | Galactocerebroside |
| Niemann Pick, Types A & B | Acid Sphingomyelinase | Sphingomyelin |
| Niemann-Pick, Type C | Cholesterol Esterification Defect | Sphingomyelin |
| Niemann-Pick, Type D | Unknown | Sphingomyelin |
| Farber Disease | Acid Ceramidase | Ceramide |
| Wolman Disease | Acid Lipase | Cholesteryl Esters |
| Hurler Syndrome (MPS IH) | α-L-Iduronidase | Heparan & Dermatan Sulfates |
| Scheie Syndrome (MPS IS) | α-L-Iduronidase | Heparan & Dermatan, Sulfates |
| Hurler-Scheie (MPS IH/S) | α-L-Iduronidase | Heparan & Dermatan Sulfates |

TABLE 2-continued

| Disease Name | Enzyme Deficiency | Substance Stored |
| --- | --- | --- |
| Hunter Syndrome (MPS II) | Iduronate Sulfatase | Heparan & Dermatan Sulfates |
| Sanfilippo A (MPS IIIA) | Heparan N-Sulfatase | Heparan Sulfate |
| Sanfilippo B (MPS IIIB) | α-N-Acetylglucosaminidase | Heparan Sulfate |
| Sanfilippo C (MPS IIIC) | Acetyl-CoA-Glucosaminide Acetyltransferase | Heparan Sulfate |
| Sanfilippo D (MPS IIID) | N-Acetylglucosamine-6-Sulfatase | Heparan Sulfate |
| Morquio B (MPS IVB) | β-Galactosidase | Keratan Sulfate |
| Maroteaux-Lamy (MPS VI) | Arylsulfatase B | Dermatan Sulfate |
| Sly Syndrome (MPS VII) | β-Glucuronidase | |
| α-Mannosidosis | α-Mannosidase | Mannose/Oligosaccharides |
| β-Mannosidosis | β-Mannosidase | Mannose/Oligosaccharides |
| Fucosidosis | α-L-Fucosidase | Fucosyl Oligosaccharides |
| Aspartylglucosaminuria | N-Aspartyl-β-Glucosaminidase | Aspartylglucosamine Asparagines |
| Sialidosis (Mucolipidosis I) | α-Neuraminidase | Sialyloligosaccharides |
| Galactosialidosis (Goldberg Syndrome) | Lysosomal Protective Protein Deficiency | Sialyloligosaccharides |
| Schindler Disease | α-N-Acetyl-Galactosaminidase | |
| Mucolipidosis II (I-Cell Disease) | N-Acetylglucosamine-1-Phosphotransferase | Heparan Sulfate |
| Mucolipidosis III (Pseudo-Hurler Polydystrophy) | Same as ML II | |
| Cystinosis | Cystine Transport Protein | Free Cystine |
| Salla Disease | Sialic Acid Transport Protein | Free Sialic Acid and Glucuronic Acid |
| Infantile Sialic Acid Storage Disease | Sialic Acid Transport Protein | Free Sialic Acid and Glucuronic Acid |
| Infantile Neuronal Ceroid Lipofuscinosis | Palmitoyl-Protein Thioesterase | Lipofuscins |
| Mucolipidosis IV | Unknown | Gangliosides & Hyaluronic Acid |
| Prosaposin | Saposins A, B, C or D | |

Inventive methods according to the present invention may be used to deliver various other replacement enzymes. As used herein, replacement enzymes suitable for the present invention may include any enzyme that can act to replace at least partial activity of the deficient or missing lysosomal enzyme in a lysosomal storage disease to be treated. In some embodiments, a replacement enzyme is capable of reducing accumulated substance in lysosomes or that can rescue or ameliorate one or more lysosomal storage disease symptoms.

In some embodiments, a suitable replacement enzyme may be any lysosomal enzyme known to be associated with the lysosomal storage disease to be treated. In some embodiments, a suitable replacement enzyme is an enzyme selected from the enzyme listed in Table 2 above.

In some embodiments, a replacement enzyme suitable for the invention may have a wild-type or naturally occurring sequence. In some embodiments, a replacement enzyme suitable for the invention may have a modified sequence having substantial homology or identify to the wild-type or naturally-occurring sequence (e.g., having at least 50%, 55%, 60%, 65%, 70%, 75%, 80%, 85%, 90%, 95%, 98% sequence identity to the wild-type or naturally-occurring sequence).

A replacement enzyme suitable for the present invention may be produced by any available means. For example, replacement enzymes may be recombinantly produced by utilizing a host cell system engineered to express a replacement enzyme-encoding nucleic acid. Alternatively or additionally, replacement enzymes may be produced by activating endogenous genes. Alternatively or additionally, replacement enzymes may be partially or fully prepared by chemical synthesis. Alternatively or additionally, replacements enzymes may also be purified from natural sources.

Where enzymes are recombinantly produced, any expression system can be used. To give but a few examples, known expression systems include, for example, egg, baculovirus, plant, yeast, or mammalian cells.

In some embodiments, enzymes suitable for the present invention are produced in mammalian cells. Non-limiting examples of mammalian cells that may be used in accordance with the present invention include BALB/c mouse myeloma line (NSO/1, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); human fibrosarcoma cell line (e.g., HT1080); baby hamster kidney cells (BHK, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

In some embodiments, inventive methods according to the present invention are used to deliver replacement enzymes produced from human cells. In some embodiments, inventive methods according to the present invention are used to deliver replacement enzymes produced from CHO cells.

In some embodiments, replacement enzymes delivered using a method of the invention contain a moiety that binds to a receptor on the surface of brain cells to facilitate cellular uptake and/or lysosomal targeting. For example, such a receptor may be the cation-independent mannose-6-phosphate receptor (CI-MPR) which binds the mannose-6-phosphate (M6P) residues. In addition, the CI-MPR also binds other proteins including IGF-II. In some embodiments, a replacement enzyme suitable for the present invention contains M6P residues on the surface of the protein. In some embodiments, a replacement enzyme suitable for the present invention may contain bis-phosphorylated oligosaccharides which have higher binding affinity to the CI-MPR. In some embodiments, a suitable enzyme contains up to about an average of about at least 20% bis-phosphorylated oligosaccharides per enzyme. In other embodiments, a suitable enzyme may contain about 10%, 15%, 18%, 20%, 25%, 30%, 35%, 40%, 45%, 50%, 55%, 60% bis-phosphorylated oligosaccharides per enzyme. While such bis-phosphorylated oligosaccharides may be naturally present on the enzyme, it should be noted that the enzymes may be modified to possess such oligosaccharides. For example, suitable replacement enzymes may be modified by certain enzymes which are capable of catalyzing the transfer of N-acetylglucosamine-L-phosphate from UDP-GlcNAc to the 6' position of α-1,2-- linked mannoses on lysosomal enzymes. Methods and compositions for producing and using such enzymes are described by, for example, Canfield et al. in U.S. Pat. No. 6,537,785, and U.S. Pat. No. 6,534,300, each incorporated herein by reference.

with the formulations intended to deliver some therapeutic agents, and in particular proteins or enzymes. For example, the calcium salts present in Elliott's B Solution are capable of mediating protein precipitation and thereby reducing the stability of the formulation.

TABLE 3

| Solution | $Na^+$ mEq/L | $K^+$ mEq/L | $Ca^{++}$ mEq/L | $Mg^{++}$ mEq/L | $HCO_3^-$ mEq/L | $Cl^-$ mEq/L | pH | Phosphorous mg/L | Glucose mg/L |
|---|---|---|---|---|---|---|---|---|---|
| CSF | 117-137 | 2.3 | 2.2 | 2.2 | 22.9 | 113-127 | 7.31 | 1.2-2.1 | 45-80 |
| Elliott's B Sol'n | 149 | 2.6 | 2.7 | 2.4 | 22.6 | 132 | 6.0-7.5 | 2.3 | 80 |

In some embodiments, replacement enzymes for use in the present invention may be conjugated or fused to a lysosomal targeting moiety that is capable of binding to a receptor on the surface of brain cells. A suitable lysosomal targeting moiety can be IGF-I, IGF-II, RAP, p97, and variants, homologues or fragments thereof (e.g., including those peptide having a sequence at least 70%, 75%, 80%, 85%, 90%, or 95% identical to a wild-type mature human IGF-I, IGF-II, RAP, p97 peptide sequence).

In some embodiments, replacement enzymes suitable for the present invention have not been modified to enhance delivery or transport of such agents across the BBB and into the CNS.

In some embodiments, a therapeutic protein includes a targeting moiety (e.g., a lysosome targeting sequence) and/or a membrane-penetrating peptide. In some embodiments, a targeting sequence and/or a membrane-penetrating peptide is an intrinsic part of the therapeutic moiety (e.g., via a chemical linkage, via a fusion protein). In some embodiments, a targeting sequence contains a mannose-6-phosphate moiety. In some embodiments, a targeting sequence contains an IGF-I moiety. In some embodiments, a targeting sequence contains an IGF-II moiety.

Formulations

In some embodiments, desired enzymes are delivered in stable formulations for intrathecal delivery. Certain embodiments of the invention are based, at least in part, on the discovery that various formulations disclosed herein facilitate the effective delivery and distribution of one or more therapeutic agents (e.g., an I2S enzyme) to targeted tissues, cells and/or organelles of the CNS. Among other things, formulations described herein are capable of solubilizing high concentrations of therapeutic agents (e.g., an I2S enzyme) and are suitable for the delivery of such therapeutic agents to the CNS of subjects for the treatment of diseases having a CNS component and/or etiology (e.g., Hunters Syndrome). The compositions described herein are further characterized by improved stability and improved tolerability when administered to the CNS of a subject (e.g., intrathecally) in need thereof.

Before the present invention, traditional unbuffered isotonic saline and Elliott's B solution, which is artificial CSF, were typically used for intrathecal delivery. A comparison depicting the compositions of CSF relative to Elliott's B solution is included in Table 3 below. As shown in Table 3, the concentration of Elliot's B Solution closely parallels that of the CSF. Elliott's B Solution, however contains a very low buffer concentration and accordingly may not provide the adequate buffering capacity needed to stabilize therapeutic agents (e.g., proteins), especially over extended periods of time (e.g., during storage conditions). Furthermore, Elliott's B Solution contains certain salts which may be incompatible Thus, in some embodiments, formulations suitable for CNS delivery according to the present invention are not synthetic or artificial CSF.

In some embodiments, formulations for CNS delivery have been formulated such that they are capable of stabilizing, or alternatively slowing or preventing the degradation, of a therapeutic agent formulated therewith (e.g., an I2S enzyme). As used herein, the term "stable" refers to the ability of the therapeutic agent (e.g., an I2S enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., preferably for at least 1, 3, 6, 12, 18, 24, 30, 36 months or more). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measure by formation of high molecular weight (HMW) aggregates, loss of enzyme activity, generation of peptide fragments and shift of charge profiles.

Stability of the therapeutic agent is of particular importance. Stability of the therapeutic agent may be further assessed relative to the biological activity or physiochemical integrity of the therapeutic agent over extended periods of time. For example, stability at a given time point may be compared against stability at an earlier time point (e.g., upon formulation day 0) or against unformulated therapeutic agent and the results of this comparison expressed as a percentage. Preferably, the pharmaceutical compositions of the present invention maintain at least 100%, at least 99%, at least 98%, at least 97% at least 95%, at least 90%, at least 85%, at least 80%, at least 75%, at least 70%, at least 65%, at least 60%, at least 55% or at least 50% of the therapeutic agent's biological activity or physiochemical integrity over an extended period of time (e.g., as measured over at least about 6-12 months, at room temperature or under accelerated storage conditions).

In some embodiments, therapeutic agents (e.g., desired enzymes) are soluble in formulations of the present invention. The term "soluble" as it relates to the therapeutic agents of the present invention refer to the ability of such therapeutic agents to form a homogenous solution. Preferably the solubility of the therapeutic agent in the solution into which it is administered and by which it is transported to the target site of action (e.g., the cells and tissues of the brain) is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts.) In some embodiments, the pharmaceutical compositions are formulated such that calcium salts are excluded from such compositions.

Suitable formulations, in either aqueous, pre-lyophilized, lyophilized or reconstituted form, may contain a therapeutic agent of interest at various concentrations. In some embodiments, formulations may contain a protein or therapeutic agent of interest at a concentration in the range of about 0.1 mg/ml to 100 mg/ml (e.g., about 0.1 mg/ml to 80 mg/ml, about 0.1 mg/ml to 60 mg/ml, about 0.1 mg/ml to 50 mg/ml, about 0.1 mg/ml to 40 mg/ml, about 0.1 mg/ml to 30 mg/ml, about 0.1 mg/ml to 25 mg/ml, about 0.1 mg/ml to 20 mg/ml, about 0.1 mg/ml to 60 mg/ml, about 0.1 mg/ml to 50 mg/ml, about 0.1 mg/ml to 40 mg/ml, about 0.1 mg/ml to 30 mg/ml, about 0.1 mg/ml to 25 mg/ml, about 0.1 mg/ml to 20 mg/ml, about 0.1 mg/ml to 15 mg/ml, about 0.1 mg/ml to 10 mg/ml, about 0.1 mg/ml to 5 mg/ml, about 1 mg/ml to 10 mg/ml, about 1 mg/ml to 20 mg/ml, about 1 mg/ml to 40 mg/ml, about 5 mg/ml to 100 mg/ml, about 5 mg/ml to 50 mg/ml, or about 5 mg/ml to 25 mg/ml). In some embodiments, formulations according to the invention may contain a therapeutic agent at a concentration of approximately 1 mg/ml, 5 mg/ml, 10 mg/ml, 15 mg/ml, 20 mg/ml, 25 mg/ml, 30 mg/ml, 40 mg/ml, 50 mg/ml, 60 mg/ml, 70 mg/ml, 80 mg/ml, 90 mg/ml, or 100 mg/ml.

The formulations of the present invention are characterized by their tolerability either as aqueous solutions or as reconstituted lyophilized solutions. As used herein, the terms "tolerable" and "tolerability" refer to the ability of the pharmaceutical compositions of the present invention to not elicit an adverse reaction in the subject to whom such composition is administered, or alternatively not to elicit a serious adverse reaction in the subject to whom such composition is administered. In some embodiments, the pharmaceutical compositions of the present invention are well tolerated by the subject to whom such compositions is administered.

Many therapeutic agents, and in particular the proteins and enzymes of the present invention, require controlled pH and specific excipients to maintain their solubility and stability in the pharmaceutical compositions of the present invention. Table 4 below identifies typical exemplary aspects of protein formulations considered to maintain the solubility and stability of the protein therapeutic agents of the present invention.

TABLE 4

| Parameter | Typical Range/Type | Rationale |
| --- | --- | --- |
| pH | 5 to 7.5 | For stability<br>Sometimes also for solubility |
| Buffer type | acetate, succinate, citrate, histidine, phosphate or Tris | To maintain optimal pH<br>May also affect stability |
| Buffer concentration | 5-50 mM | To maintain pH<br>May also stabilize or add ionic strength |
| Tonicifier | NaCl, sugars, mannitol | To render iso-osmotic or isotonic solutions |
| Surfactant | Polysorbate 20, polysorbate 80 | To stabilize against interfaces and shear |
| Other | Amino acids (e.g. arginine) at tens to hundreds of mM | For enhanced solubility or stability |

Buffers

The pH of the formulation is an additional factor which is capable of altering the solubility of a therapeutic agent (e.g., an enzyme or protein) in an aqueous formulation or for a pre-lyophilization formulation. Accordingly the formulations of the present invention preferably comprise one or more buffers. In some embodiments the aqueous formulations comprise an amount of buffer sufficient to maintain the optimal pH of said composition between about 4.0-8.0 (e.g., about 4.0, 4.5, 5.0, 5.5, 6.0, 6.2, 6.4, 6.5, 6.6, 6.8, 7.0, 7.5, or 8.0). In some embodiments, the pH of the formulation is between about 5.0-7.5, between about 5.5-7.0, between about 6.0-7.0, between about 5.5-6.0, between about 5.5-6.5, between about 5.0-6.0, between about 5.0-6.5 and between about 6.0-7.5. Suitable buffers include, for example acetate, citrate, histidine, phosphate, succinate, tris(hydroxymethyl) aminomethane ("Tris") and other organic acids. The buffer concentration and pH range of the pharmaceutical compositions of the present invention are factors in controlling or adjusting the tolerability of the formulation. In some embodiments, a buffering agent is present at a concentration ranging between about 1 mM to about 150 mM, or between about 10 mM to about 50 mM, or between about 15 mM to about 50 mM, or between about 20 mM to about 50 mM, or between about 25 mM to about 50 mM. In some embodiments, a suitable buffering agent is present at a concentration of approximately 1 mM, 5 mM, 10 mM, 15 mM, 20 mM, 25 mM, 30 mM, 35 mM, 40 mM, 45 mM 50 mM, 75 mM, 100 mM, 125 mM or 150 mM.

Tonicity

In some embodiments, formulations, in either aqueous, pre-lyophilized, lyophilized or reconstituted form, contain an isotonicity agent to keep the formulations isotonic. Typically, by "isotonic" is meant that the formulation of interest has essentially the same osmotic pressure as human blood. Isotonic formulations will generally have an osmotic pressure from about 240 mOsm/kg to about 350 mOsm/kg. Isotonicity can be measured using, for example, a vapor pressure or freezing point type osmometers. Exemplary isotonicity agents include, but are not limited to, glycine, sorbitol, mannitol, sodium chloride and arginine. In some embodiments, suitable isotonic agents may be present in aqueous and/or pre-lyophilized formulations at a concentration from about 0.01-5% (e.g., 0.05, 0.1, 0.15, 0.2, 0.3, 0.4, 0.5, 0.75, 1.0, 1.25, 1.5, 2.0, 2.5, 3.0, 4.0 or 5.0%) by weight. In some embodiments, formulations for lyophilization contain an isotonicity agent to keep the pre-lyophilization formulations or the reconstituted formulations isotonic.

While generally isotonic solutions are preferred for parenterally administered drugs, the use of isotonic solutions may change solubility for some therapeutic agents and in particular some proteins and/or enzymes. Slightly hypertonic solutions (e.g., up to 175 mM sodium chloride in 5 mM sodium phosphate at pH 7.0) and sugar-containing solutions (e.g., up to 2% sucrose in 5 mM sodium phosphate at pH 7.0) have been demonstrated to be well tolerated. The most common approved CNS bolus formulation composition is saline (about 150 mM NaCl in water).

Stabilizing Agents

In some embodiments, formulations may contain a stabilizing agent, or lyoprotectant, to protect the protein. Typically, a suitable stabilizing agent is a sugar, a non-reducing sugar and/or an amino acid. Exemplary sugars include, but are not limited to, dextran, lactose, mannitol, mannose, sorbitol, raffinose, sucrose and trehalose. Exemplary amino acids include, but are not limited to, arginine, glycine and methionine. Additional stabilizing agents may include sodium chloride, hydroxyethyl starch and polyvinylpyrolidone. The amount of stabilizing agent in the lyophilized formulation is generally such that the formulation will be isotonic. However, hypertonic reconstituted formulations may also be suitable. In addition, the amount of stabilizing agent must not be too low such that an unacceptable amount of degradation/aggregation of the therapeutic agent occurs. Exemplary stabilizing agent concentrations in the formulation may range from about 1 mM to about 400 mM (e.g., from about 30 mM to about 300 mM, and from about 50 mM to about 100 mM), or alternatively, from 0.1% to 15% (e.g., from 1% to 10%, from 5% to 15%, from 5% to 10%) by weight. In some embodiments, the ratio of the mass amount of the stabilizing agent and the therapeutic agent is about 1:1. In other embodiments, the ratio of the mass amount of the stabilizing agent and the therapeutic agent can be about 0.1:1, 0.2:1, 0.25:1, 0.4:1, 0.5:1, 1:1, 2:1, 2.6:1, 3:1, 4:1, 5:1, 10:1, or 20:1. In some embodiments, suitable for lyophilization, the stabilizing agent is also a lyoprotectant.

In some embodiments, liquid formulations suitable for the present invention contain amorphous materials. In some embodiments, liquid formulations suitable for the present invention contain a substantial amount of amorphous materials (e.g., sucrose-based formulations). In some embodiments, liquid formulations suitable for the present invention contain partly crystalline/partly amorphous materials.

Bulking Agents

In some embodiments, suitable formulations for lyophilization may further include one or more bulking agents. A "bulking agent" is a compound which adds mass to the lyophilized mixture and contributes to the physical structure of the lyophilized cake. For example, a bulking agent may improve the appearance of lyophilized cake (e.g., essentially uniform lyophilized cake). Suitable bulking agents include, but are not limited to, sodium chloride, lactose, mannitol, glycine, sucrose, trehalose, hydroxyethyl starch. Exemplary concentrations of bulking agents are from about 1% to about 10% (e.g., 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, and 10.0%).

Surfactants

In some embodiments, it is desirable to add a surfactant to formulations. Exemplary surfactants include nonionic surfactants such as Polysorbates (e.g., Polysorbates 20 or 80); poloxamers (e.g., poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; and the MONAQUAT™ series (Mona Industries, Inc., Paterson, N.J.), polyethyl glycol, polypropyl glycol, and copolymers of ethylene and propylene glycol (e.g., Pluronics, PF68, etc). Typically, the amount of surfactant added is such that it reduces aggregation of the protein and minimizes the formation of particulates or effervescences. For example, a surfactant may be present in a formulation at a concentration from about 0.001-0.5% (e.g., about 0.005-0.05%, or 0.005-0.01%). In particular, a surfactant may be present in a formulation at a concentration of approximately 0.005%, 0.01%, 0.02%, 0.1%, 0.2%, 0.3%, 0.4%, or 0.5%, etc. Alternatively, or in addition, the surfactant may be added to the lyophilized formulation, pre-lyophilized formulation and/or the reconstituted formulation.

Other pharmaceutically acceptable carriers, excipients or stabilizers such as those described in Remington's Pharmaceutical Sciences 16th edition, Osol, A. Ed. (1980) may be included in the formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include, but are not limited to, additional buffering agents; preservatives; co-solvents; antioxidants including ascorbic acid and methionine; chelating agents such as EDTA; metal complexes (e.g., Zn-protein complexes); biodegradable polymers such as polyesters; and/or salt-forming counterions such as sodium.

Formulations, in either aqueous, pre-lyophilized, lyophilized or reconstituted form, in accordance with the present invention can be assessed based on product quality analysis, reconstitution time (if lyophilized), quality of reconstitution (if lyophilized), high molecular weight, moisture, and glass transition temperature. Typically, protein quality and product analysis include product degradation rate analysis using methods including, but not limited to, size exclusion HPLC (SE-HPLC), cation exchange-HPLC (CEX-HPLC), X-ray diffraction (XRD), modulated differential scanning calorimetry (mDSC), reversed phase HPLC(RP-HPLC), multi-angle light scattering (MALS), fluorescence, ultraviolet absorption, nephelometry, capillary electrophoresis (CE), SDS-PAGE, and combinations thereof. In some embodiments, evaluation of product in accordance with the present invention may include a step of evaluating appearance (either liquid or cake appearance).

Generally, formulations (lyophilized or aqueous) can be stored for extended periods of time at room temperature. Storage temperature may typically range from 0° C. to 45° C. (e.g., 4° C., 20° C., 25° C., 45° C. etc.). Formulations may be stored for a period of months to a period of years. Storage time generally will be 24 months, 12 months, 6 months, 4.5 months, 3 months, 2 months or 1 month. Formulations can be stored directly in the container used for administration, eliminating transfer steps.

Formulations can be stored directly in the lyophilization container (if lyophilized), which may also function as the reconstitution vessel, eliminating transfer steps. Alternatively, lyophilized product formulations may be measured into smaller increments for storage. Storage should generally avoid circumstances that lead to degradation of the proteins, including but not limited to exposure to sunlight, UV radiation, other forms of electromagnetic radiation, excessive heat or cold, rapid thermal shock, and mechanical shock.

Lyophilization

Inventive methods in accordance with the present invention can be utilized to lyophilize any materials, in particular, therapeutic agents. Typically, a pre-lyophilization formulation further contains an appropriate choice of excipients or other components such as stabilizers, buffering agents, bulking agents, and surfactants to prevent compound of interest from degradation (e.g., protein aggregation, deamidation, and/or oxidation) during freeze-drying and storage. The formulation for lyophilization can include one or more additional ingredients including lyoprotectants or stabilizing agents, buffers, bulking agents, isotonicity agents and surfactants.

After the substance of interest and any additional components are mixed together, the formulation is lyophilized. Lyophilization generally includes three main stages: freezing, primary drying and secondary drying. Freezing is necessary to convert water to ice or some amorphous formulation components to the crystalline form. Primary drying is the process step when ice is removed from the frozen product by direct sublimation at low pressure and temperature. Secondary drying is the process step when bounded water is removed from the product matrix utilizing the diffusion of residual water to the evaporation surface. Product temperature during secondary drying is normally higher than during primary drying. See, Tang X. et al. (2004) "Design of freeze-drying processes for pharmaceuticals: Practical advice," *Pharm. Res.,* 21:191-200; Nail S. L. et al. (2002) "Fundamentals of freeze-drying," in Development and manufacture of protein pharmaceuticals. Nail S. L. editor New York: Kluwer Academic/Plenum Publishers, pp 281-353; Wang et al. (2000) "Lyophilization and development of solid protein pharmaceuticals," *Int. J. Pharm.,* 203:1-60; Williams N. A. et al. (1984) "The lyophilization of pharmaceuticals; A literature review." *J. Parenteral Sci. Technol.,* 38:48-59. Generally, any lyophilization process can be used in connection with the present invention.

In some embodiments, an annealing step may be introduced during the initial freezing of the product. The annealing step may reduce the overall cycle time. Without wishing to be bound by any theories, it is contemplated that the annealing step can help promote excipient crystallization and formation of larger ice crystals due to re-crystallization of small crystals formed during supercooling, which, in turn, improves reconstitution. Typically, an annealing step includes an interval or oscillation in the temperature during freezing. For example, the freeze temperature may be −40° C., and the annealing step will increase the temperature to, for example, −10° C. and maintain this temperature for a set period of time. The annealing step time may range from 0.5 hours to 8 hours (e.g., 0.5, 1.0 1.5, 2.0, 2.5, 3, 4, 6, and 8 hours). The annealing temperature may be between the freezing temperature and 0° C.

Lyophilization may be performed in a container, such as a tube, a bag, a bottle, a tray, a vial (e.g., a glass vial), syringe or any other suitable containers. The containers may be disposable. Lyophilization may also be performed in a large scale or small scale. In some instances, it may be desirable to lyophilize the protein formulation in the container in which reconstitution of the protein is to be carried out in order to avoid a transfer step. The container in this instance may, for example, be a 3, 4, 5, 10, 20, 50 or 100 cc vial.

Many different freeze-dryers are available for this purpose such as Hull pilot scale dryer (SP Industries, USA), Genesis (SP Industries) laboratory freeze-dryers, or any freeze-dryers capable of controlling the given lyophilization process parameters. Freeze-drying is accomplished by freezing the formulation and subsequently subliming ice from the frozen content at a temperature suitable for primary drying. Initial freezing brings the formulation to a temperature below about −20° C. (e.g., −50° C., −45° C., −40° C., −35° C., −30° C., −25° C., etc.) in typically not more than about 4 hours (e.g., not more than about 3 hours, not more than about 2.5 hours, not more than about 2 hours). Under this condition, the product temperature is typically below the eutectic point or the collapse temperature of the formulation. Typically, the shelf temperature for the primary drying will range from about −30 to 25° C. (provided the product remains below the melting point during primary drying) at a suitable pressure, ranging typically from about 20 to 250 mTorr. The formulation, size and type of the container holding the sample (e.g., glass vial) and the volume of liquid will mainly dictate the time required for drying, which can range from a few hours to several days. A secondary drying stage is carried out at about 0-60° C., depending primarily on the type and size of container and the type of therapeutic protein employed. Again, volume of liquid will mainly dictate the time required for drying, which can range from a few hours to several days.

As a general proposition, lyophilization will result in a lyophilized formulation in which the moisture content thereof is less than about 5%, less than about 4%, less than about 3%, less than about 2%, less than about 1%, and less than about 0.5%.

Reconstitution

While the pharmaceutical compositions of the present invention are generally in an aqueous form upon administration to a subject, in some embodiments the pharmaceutical compositions of the present invention are lyophilized. Such compositions must be reconstituted by adding one or more diluents thereto prior to administration to a subject. At the desired stage, typically at an appropriate time prior to administration to the patient, the lyophilized formulation may be reconstituted with a diluent such that the protein concentration in the reconstituted formulation is desirable.

Various diluents may be used in accordance with the present invention. In some embodiments, a suitable diluent for reconstitution is water. The water used as the diluent can be treated in a variety of ways including reverse osmosis, distillation, deionization, filtrations (e.g., activated carbon, microfiltration, nanofiltration) and combinations of these treatment methods. In general, the water should be suitable for injection including, but not limited to, sterile water or bacteriostatic water for injection.

Additional exemplary diluents include a pH buffered solution (e.g., phosphate-buffered saline), sterile saline solution, Elliot's solution, Ringer's solution or dextrose solution. Suitable diluents may optionally contain a preservative. Exemplary preservatives include aromatic alcohols such as benzyl or phenol alcohol. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0%, from about 0.5-1.5%, or about 1.0-1.2%.

Diluents suitable for the invention may include a variety of additives, including, but not limited to, pH buffering agents, (e.g. Tris, histidine) salts (e.g., sodium chloride) and other additives (e.g., sucrose) including those described above (e.g. stabilizing agents, isotonicity agents).

According to the present invention, a lyophilized substance (e.g., protein) can be reconstituted to a concentration of at least 25 mg/ml (e.g., at least 50 mg/ml, at least 75 mg/ml, at least 100 mg/) and in any ranges therebetween. In some embodiments, a lyophilized substance (e.g., protein) may be reconstituted to a concentration ranging from about 1 mg/ml to 100 mg/ml (e.g., from about 1 mg/ml to 50 mg/ml, from 1 mg/ml to 100 mg/ml, from about 1 mg/ml to about 5 mg/ml, from about 1 mg/ml to about 10 mg/ml, from about 1 mg/ml to about 25 mg/ml, from about 1 mg/ml to about 75 mg/ml, from about 10 mg/ml to about 30 mg/ml, from about 10 mg/ml to about 50 mg/ml, from about 10 mg/ml to about 75 mg/ml, from about 10 mg/ml to about 100 mg/ml, from about 25 mg/ml to about 50 mg/ml, from about 25 mg/ml to about 75 mg/ml, from about 25 mg/ml to about 100 mg/ml, from about 50 mg/ml to about 75 mg/ml, from about 50 mg/ml to about 100 mg/ml). In some embodiments, the concentration of protein in the reconstituted formulation may be higher than the concentration in the pre-lyophilization formulation. High protein concentrations in the reconstituted formulation are considered to be particularly useful where subcutaneous or intramuscular delivery of the reconstituted formulation is intended. In some embodiments, the protein concentration in the reconstituted formulation may be about 2-50 times (e.g., about 2-20, about 2-10 times, or about 2-5 times) of the pre-lyophilized formulation. In some embodiments, the protein concentration in the reconstituted formulation may be at least about 2 times (e.g., at least about 3, 4, 5, 10, 20, 40 times) of the pre-lyophilized formulation.

Reconstitution according to the present invention may be performed in any container. Exemplary containers suitable for the invention include, but are not limited to, such as tubes, vials, syringes (e.g., single-chamber or dual-chamber), bags, bottles, and trays. Suitable containers may be made of any materials such as glass, plastics, metal. The containers may be disposable or reusable. Reconstitution may also be performed in a large scale or small scale.

In some instances, it may be desirable to lyophilize the protein formulation in the container in which reconstitution of the protein is to be carried out in order to avoid a transfer step. The container in this instance may, for example, be a 3, 4, 5, 10, 20, 50 or 100 cc vial. In some embodiments, a suitable container for lyophilization and reconstitution is a dual chamber syringe (e.g., Lyo-Ject,® (Vetter) syringes). For example, a dual chamber syringe may contain both the lyophilized substance and the diluent, each in a separate chamber, separated by a stopper (see Example 5). To reconstitute, a plunger can be attached to the stopper at the diluent side and pressed to move diluent into the product chamber so that the diluent can contact the lyophilized substance and reconstitution may take place as described herein (see Example 5).

The pharmaceutical compositions, formulations and related methods of the invention are useful for delivering a variety of therapeutic agents to the CNS of a subject (e.g., intrathecally, intraventricularly or intracisternally) and for the treatment of the associated diseases. The pharmaceutical compositions of the present invention are particularly useful for delivering proteins and enzymes (e.g., enzyme replacement therapy) to subjects suffering from lysosomal storage disorders. The lysosomal storage diseases represent a group of relatively rare inherited metabolic disorders that result from defects in lysosomal function. The lysosomal diseases are characterized by the accumulation of undigested macromolecules within the lysosomes, which results in an increase in the size and number of such lysosomes and ultimately in cellular dysfunction and clinical abnormalities.

CNS Delivery

It is contemplated that various stable formulations described herein are generally suitable for CNS delivery of therapeutic agents. Stable formulations according to the present invention can be used for CNS delivery via various techniques and routes including, but not limited to, intra-parenchymal, intracerebral, intraventricular cerebral (ICV), intrathecal (e.g., IT-Lumbar, IT-cisterna magna) administrations and any other techniques and routes for injection directly or indirectly to the CNS and/or CSF.

Intrathecal Delivery

In some embodiments, a replacement enzyme is delivered to the CNS in a formulation described herein. In some embodiments, a replacement enzyme is delivered to the CNS by administering into the cerebrospinal fluid (CSF) of a subject in need of treatment. In some embodiments, intrathecal administration is used to deliver a desired replacement enzyme (e.g., an I2S protein) into the CSF. As used herein, intrathecal administration (also referred to as intrathecal injection) refers to an injection into the spinal canal (intrathecal space surrounding the spinal cord). Various techniques may be used including, without limitation, lateral cerebroventricular injection through a burrhole or cisternal or lumbar puncture or the like. Exemplary methods are described in Lazorthes et al. Advances in Drug Delivery Systems and Applications in Neurosurgery, 143-192 and Omaya et al., Cancer Drug Delivery, 1: 169-179, the contents of which are incorporated herein by reference.

According to the present invention, an enzyme may be injected at any region surrounding the spinal canal. In some embodiments, an enzyme is injected into the lumbar area or the cisterna magna or intraventricularly into a cerebral ventricle space. As used herein, the term "lumbar region" or "lumbar area" refers to the area between the third and fourth lumbar (lower back) vertebrae and, more inclusively, the L2-S1 region of the spine. Typically, intrathecal injection via the lumbar region or lumbar area is also referred to as "lumbar IT delivery" or "lumbar IT administration." The term "cisterna magna" refers to the space around and below the cerebellum via the opening between the skull and the top of the spine. Typically, intrathecal injection via cisterna magna is also referred to as "cisterna magna delivery." The term "cerebral ventricle" refers to the cavities in the brain that are continuous with the central canal of the spinal cord. Typically, injections via the cerebral ventricle cavities are referred to as intravetricular Cerebral (ICV) delivery.

In some embodiments, "intrathecal administration" or "intrathecal delivery" according to the present invention refers to lumbar IT administration or delivery, for example, delivered between the third and fourth lumbar (lower back) vertebrae and, more inclusively, the L2-S1 region of the spine. It is contemplated that lumbar IT administration or delivery distinguishes over cisterna magna delivery in that lumbar IT administration or delivery according to our invention provides better and more effective delivery to the distal spinal canal, while cisterna magna delivery, among other things, typically does not deliver well to the distal spinal canal.

Device for Intrathecal Delivery

Various devices may be used for intrathecal delivery according to the present invention. In some embodiments, a device for intrathecal administration contains a fluid access port (e.g., injectable port); a hollow body (e.g., catheter) having a first flow orifice in fluid communication with the fluid access port and a second flow orifice configured for insertion into spinal cord; and a securing mechanism for securing the insertion of the hollow body in the spinal cord. As a non-limiting example shown in FIG. 62, a suitable securing mechanism contains one or more nobs mounted on the surface of the hollow body and a sutured ring adjustable over the one or more nobs to prevent the hollow body (e.g., catheter) from slipping out of the spinal cord. In various embodiments, the fluid access port comprises a reservoir. In some embodiments, the fluid access port comprises a mechanical pump (e.g., an infusion pump). In some embodiments, an implanted catheter is connected to either a reservoir (e.g., for bolus delivery), or an infusion pump. The fluid access port may be implanted or external In some embodiments, intrathecal administration may be performed by either lumbar puncture (i.e., slow bolus) or via a port-catheter delivery system (i.e., infusion or bolus). In some embodiments, the catheter is inserted between the laminae of the lumbar vertebrae and the tip is threaded up the thecal space to the desired level (generally L3-L4) (FIG. 63).

Relative to intravenous administration, a single dose volume suitable for intrathecal administration is typically small. Typically, intrathecal delivery according to the present invention maintains the balance of the composition of the CSF as well as the intracranial pressure of the subject. In some embodiments, intrathecal delivery is performed absent the corresponding removal of CSF from a subject. In some embodiments, a suitable single dose volume may be e.g., less than about 10 ml, 8 ml, 6 ml, 5 ml, 4 ml, 3 ml, 2 ml, 1.5 ml, 1 ml, or 0.5 ml. In some embodiments, a suitable single dose volume may be about 0.5-5 ml, 0.5-4 ml, 0.5-3 ml, 0.5-2 ml, 0.5-1 ml, 1-3 ml, 1-5 ml, 1.5-3 ml, 1-4 ml, or 0.5-1.5 ml. In some embodiments, intrathecal delivery according to the present invention involves a step of removing a desired amount of CSF first. In some embodiments, less than about 10 ml (e.g., less than about 9 ml, 8 ml, 7 ml, 6 ml, 5 ml, 4 ml, 3 ml, 2 ml, 1 ml) of CSF is first removed before IT administration. In those cases, a suitable single dose volume may be e.g., more than about 3 ml, 4 ml, 5 ml, 6 ml, 7 ml, 8 ml, 9 ml, 10 ml, 15 ml, or 20 ml.

Various other devices may be used to effect intrathecal administration of a therapeutic composition. For example, formulations containing desired enzymes may be given using an Ommaya reservoir which is in common use for intrathecally administering drugs for meningeal carcinomatosis (Lancet 2: 983-84, 1963). More specifically, in this method, a ventricular tube is inserted through a hole formed in the anterior horn and is connected to an Ommaya reservoir installed under the scalp, and the reservoir is subcutaneously punctured to intrathecally deliver the particular enzyme being replaced, which is injected into the reservoir. Other devices for intrathecal administration of therapeutic compositions or formulations to an individual are described in U.S. Pat. No. 6,217,552, incorporated herein by reference. Alternatively, the drug may be intrathecally given, for example, by a single injection, or continuous infusion. It should be understood that the dosage treatment may be in the form of a single dose administration or multiple doses.

For injection, formulations of the invention can be formulated in liquid solutions. In addition, the enzyme may be formulated in solid form and re-dissolved or suspended immediately prior to use. Lyophilized forms are also included. The injection can be, for example, in the form of a bolus injection or continuous infusion (e.g., using infusion pumps) of the enzyme.

In one embodiment of the invention, the enzyme is administered by lateral cerebro ventricular injection into the brain of a subject. The injection can be made, for example, through a burr hole made in the subject's skull. In another embodiment, the enzyme and/or other pharmaceutical formulation is administered through a surgically inserted shunt into the cerebral ventricle of a subject. For example, the injection can be made into the lateral ventricles, which are larger. In some embodiments, injection into the third and fourth smaller ventricles can also be made.

In yet another embodiment, the pharmaceutical compositions used in the present invention are administered by injection into the cisterna magna, or lumbar area of a subject.

In another embodiment of the method of the invention, the pharmaceutically acceptable formulation provides sustained delivery, e.g., "slow release" of the enzyme or other pharmaceutical composition used in the present invention, to a subject for at least one, two, three, four weeks or longer periods of time after the pharmaceutically acceptable formulation is administered to the subject.

As used herein, the term "sustained delivery" refers to continual delivery of a pharmaceutical formulation of the invention in vivo over a period of time following administration, preferably at least several days, a week or several weeks. Sustained delivery of the composition can be demonstrated by, for example, the continued therapeutic effect of the enzyme over time (e.g., sustained delivery of the enzyme can be demonstrated by continued reduced amount of storage granules in the subject). Alternatively, sustained delivery of the enzyme may be demonstrated by detecting the presence of the enzyme in vivo over time.

Delivery to Target Tissues

As discussed above, one of the surprising and important features of the present invention is that therapeutic agents, in particular, replacement enzymes administered using inventive methods and compositions of the present invention are able to effectively and extensively diffuse across the brain surface and penetrate various layers or regions of the brain, including deep brain regions. In addition, inventive methods and compositions of the present invention effectively deliver therapeutic agents (e.g., an I2S enzyme) to various tissues, neurons or cells of spinal cord, including the lumbar region, which is hard to target by existing CNS delivery methods such as ICV injection. Furthermore, inventive methods and compositions of the present invention deliver sufficient amount of therapeutic agents (e.g., an I2S enzyme) to the blood stream and various peripheral organs and tissues.

Thus, in some embodiments, a therapeutic protein (e.g., an I2S enzyme) is delivered to the central nervous system of a subject. In some embodiments, a therapeutic protein (e.g., an I2S enzyme) is delivered to one or more of target tissues of brain, spinal cord, and/or peripheral organs. As used herein, the term "target tissues" refers to any tissue that is affected by the lysosomal storage disease to be treated or any tissue in which the deficient lysosomal enzyme is normally expressed. In some embodiments, target tissues include those tissues in which there is a detectable or abnormally high amount of enzyme substrate, for example stored in the cellular lysosomes of the tissue, in patients suffering from or susceptible to the lysosomal storage disease. In some embodiments, target tissues include those tissues that display disease-associated pathology, symptom, or feature. In some embodiments, target tissues include those tissues in which the deficient lysosomal enzyme is normally expressed at an elevated level. As used herein, a target tissue may be a brain target tissue, a spinal cord target tissue and/or a peripheral target tissue. Exemplary target tissues are described in detail below.

Brain Target Tissues

In general, the brain can be divided into different regions, layers and tissues. For example, meningeal tissue is a system of membranes which envelops the central nervous system, including the brain. The meninges contain three layers, including dura matter, arachnoid matter, and pia matter. In general, the primary function of the meninges and of the cerebrospinal fluid is to protect the central nervous system. In some embodiments, a therapeutic protein in accordance with the present invention is delivered to one or more layers of the meninges.

The brain has three primary subdivisions, including the cerebrum, cerebellum, and brain stem. The cerebral hemispheres, which are situated above most other brain structures, are covered with a cortical layer. Underneath the cerebrum lies the brainstem, which resembles a stalk on which the cerebrum is attached. At the rear of the brain, beneath the cerebrum and behind the brainstem, is the cerebellum.

The diencephalon, which is located near the midline of the brain and above the mesencephalon, contains the thalamus, metathalamus, hypothalamus, epithalamus, prethalamus, and pretectum. The mesencephalon, also called the midbrain, contains the tectum, tegumentum, ventricular mesocoelia, and cerebral peduncels, the red nucleus, and the cranial nerve III nucleus. The mesencephalon is associated with vision, hearing, motor control, sleep/wake, alertness, and temperature regulation.

Regions of tissues of the central nervous system, including the brain, can be characterized based on the depth of the tissues. For example, CNS (e.g., brain) tissues can be characterized as surface or shallow tissues, mid-depth tissues, and/or deep tissues.

According to the present invention, a therapeutic protein (e.g., a replacement enzyme) may be delivered to any appropriate brain target tissue(s) associated with a particular disease to be treated in a subject. In some embodiments, a therapeutic protein (e.g., a replacement enzyme) in accordance with the present invention is delivered to surface or shallow brain target tissue. In some embodiments, a therapeutic protein in accordance with the present invention is delivered to mid-depth brain target tissue. In some embodiments, a therapeutic protein in accordance with the present invention is delivered to deep brain target tissue. In some embodiments, a therapeutic protein in accordance with the present invention is delivered to a combination of surface or shallow brain target tissue, mid-depth brain target tissue, and/or deep brain target tissue. In some embodiments, a therapeutic protein in accordance with the present invention is delivered to a deep brain tissue at least 4 mm, 5 mm, 6 mm, 7 mm, 8 mm, 9 mm, 10 mm or more below (or internal to) the external surface of the brain.

In some embodiments, therapeutic agents (e.g., enzymes) are delivered to one or more surface or shallow tissues of cerebrum. In some embodiments, the targeted surface or shallow tissues of the cerebrum are located within 4 mm from the surface of the cerebrum. In some embodiments, the targeted surface or shallow tissues of the cerebrum are selected from pia mater tissues, cerebral cortical ribbon tissues, hippocampus, Virchow Robin space, blood vessels within the VR space, the hippocampus, portions of the hypothalamus on the inferior surface of the brain, the optic nerves and tracts, the olfactory bulb and projections, and combinations thereof.

In some embodiments, therapeutic agents (e.g., enzymes) are delivered to one or more deep tissues of the cerebrum. In some embodiments, the targeted surface or shallow tissues of the cerebrum are located 4 mm (e.g., 5 mm, 6 mm, 7 mm, 8 mm, 9 mm, or 10 mm) below (or internal to) the surface of the cerebrum. In some embodiments, targeted deep tissues of the cerebrum include the cerebral cortical ribbon. In some embodiments, targeted deep tissues of the cerebrum include one or more of the diencephalon (e.g., the hypothalamus, thalamus, prethalamus, subthalamus, etc.), metencephalon, lentiform nuclei, the basal ganglia, caudate, putamen, amygdala, globus pallidus, and combinations thereof.

In some embodiments, therapeutic agents (e.g., enzymes) are delivered to one or more tissues of the cerebellum. In certain embodiments, the targeted one or more tissues of the cerebellum are selected from the group consisting of tissues of the molecular layer, tissues of the Purkinje cell layer, tissues of the Granular cell layer, cerebellar peduncles, and combination thereof. In some embodiments, therapeutic agents (e.g., enzymes) are delivered to one or more deep tissues of the cerebellum including, but not limited to, tissues of the Purkinje cell layer, tissues of the Granular cell layer, deep cerebellar white matter tissue (e.g., deep relative to the Granular cell layer), and deep cerebellar nuclei tissue.

In some embodiments, therapeutic agents (e.g., enzymes) are delivered to one or more tissues of the brainstem. In some embodiments, the targeted one or more tissues of the brainstem include brain stem white matter tissue and/or brain stem nuclei tissue.

In some embodiments, therapeutic agents (e.g., enzymes) are delivered to various brain tissues including, but not limited to, gray matter, white matter, periventricular areas, pia-arachnoid, meninges, neocortex, cerebellum, deep tissues in cerebral cortex, molecular layer, caudate/putamen region, midbrain, deep regions of the pons or medulla, and combinations thereof.

In some embodiments, therapeutic agents (e.g., enzymes) are delivered to various cells in the brain including, but not limited to, neurons, glial cells, perivascular cells and/or meningeal cells. In some embodiments, a therapeutic protein is delivered to oligodendrocytes of deep white matter.

Spinal Cord

In general, regions or tissues of the spinal cord can be characterized based on the depth of the tissues. For example, spinal cord tissues can be characterized as surface or shallow tissues, mid-depth tissues, and/or deep tissues.

In some embodiments, therapeutic agents (e.g., enzymes) are delivered to one or more surface or shallow tissues of the spinal cord. In some embodiments, a targeted surface or shallow tissue of the spinal cord is located within 4 mm from the surface of the spinal cord. In some embodiments, a targeted surface or shallow tissue of the spinal cord contains pia matter and/or the tracts of white matter.

In some embodiments, therapeutic agents (e.g., enzymes) are delivered to one or more deep tissues of the spinal cord. In some embodiments, a targeted deep tissue of the spinal cord is located internal to 4 mm from the surface of the spinal cord. In some embodiments, a targeted deep tissue of the spinal cord contains spinal cord grey matter and/or ependymal cells.

In some embodiments, therapeutic agents (e.g., enzymes) are delivered to neurons of the spinal cord.

Peripheral Target Tissues

As used herein, peripheral organs or tissues refer to any organs or tissues that are not part of the central nervous system (CNS). Peripheral target tissues may include, but are not limited to, blood system, liver, kidney, heart, endothelium, bone marrow and bone marrow derived cells, spleen, lung, lymph node, bone, cartilage, ovary and testis. In some embodiments, a therapeutic protein (e.g., a replacement enzyme) in accordance with the present invention is delivered to one or more of the peripheral target tissues.

Biodistribution and Bioavailability

In various embodiments, once delivered to the target tissue, a therapeutic agent (e.g., an I2S enzyme) is localized intracellularly. For example, a therapeutic agent (e.g., enzyme) may be localized to exons, axons, lysosomes, mitochondria or vacuoles of a target cell (e.g., neurons such as Purkinje cells). For example, in some embodiments intrathecally-administered enzymes demonstrate translocation dynamics such that the enzyme moves within the perivascular space (e.g., by pulsation-assisted convective mechanisms). In addition, active axonal transport mechanisms relating to the association of the administered protein or enzyme with neurofilaments may also contribute to or otherwise facilitate the distribution of intrathecally-administered proteins or enzymes into the deeper tissues of the central nervous system.

In some embodiments, a therapeutic agent (e.g., an I2S enzyme) delivered according to the present invention may achieve therapeutically or clinically effective levels or activities in various targets tissues described herein. As used herein, a therapeutically or clinically effective level or activity is a level or activity sufficient to confer a therapeutic effect in a target tissue. The therapeutic effect may be objective (i.e., measurable by some test or marker) or subjective (i.e., subject gives an indication of or feels an effect). For example, a therapeutically or clinically effective level or activity may be an enzymatic level or activity that is sufficient to ameliorate symptoms associated with the disease in the target tissue (e.g., GAG storage).

In some embodiments, a therapeutic agent (e.g., a replacement enzyme) delivered according to the present invention may achieve an enzymatic level or activity that is at least 5%, 10%, 20%, 30%, 40%, 50%, 60%, 70%, 80%, 90%, 95% of the normal level or activity of the corresponding lysosomal enzyme in the target tissue. In some embodiments, a therapeutic agent (e.g., a replacement enzyme) delivered according to the present invention may achieve an enzymatic level or activity that is increased by at least 1-fold, 2-fold, 3-fold, 4-fold, 5-fold, 6-fold, 7-fold, 8-fold, 9-fold or 10-fold as compared to a control (e.g., endogenous levels or activities without the treatment). In some embodiments, a therapeutic agent (e.g., a replacement enzyme) delivered according to the present invention may achieve an increased enzymatic level or activity at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg or 600 nmol/hr/mg in a target tissue.

In some embodiments, inventive methods according to the present invention are particularly useful for targeting the lumbar region. In some embodiments, a therapeutic agent (e.g., a replacement enzyme) delivered according to the present invention may achieve an increased enzymatic level or activity in the lumbar region of at least approximately 500 nmol/hr/mg, 600 nmol/hr/mg, 700 nmol/hr/mg, 800 nmol/hr/mg, 900 nmol/hr/mg, 1000 nmol/hr/mg, 1500 nmol/hr/mg, 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, or 10,000 nmol/hr/mg.

In general, therapeutic agents (e.g., replacement enzymes) delivered according to the present invention have sufficiently long half time in CSF and target tissues of the brain, spinal cord, and peripheral organs. In some embodiments, a therapeutic agent (e.g., a replacement enzyme) delivered according to the present invention may have a half-life of at least approximately 30 minutes, 45 minutes, 60 minutes, 90 minutes, 2 hours, 3 hours, 4 hours, 5 hours, 6 hours, 7 hours, 8 hours, 9 hours, 10 hours, 12 hours, 16 hours, 18 hours, 20 hours, 25 hours, 30 hours, 35 hours, 40 hours, up to 3 days, up to 7 days, up to 14 days, up to 21 days or up to a month. In some embodiments, In some embodiments, a therapeutic agent (e.g., a replacement enzyme) delivered according to the present invention may retain detectable level or activity in CSF or bloodstream after 12 hours, 24 hours, 30 hours, 36 hours, 42 hours, 48 hours, 54 hours, 60 hours, 66 hours, 72 hours, 78 hours, 84 hours, 90 hours, 96 hours, 102 hours, or a week following administration. Detectable level or activity may be determined using various methods known in the art.

In certain embodiments, a therapeutic agent (e.g., a replacement enzyme) delivered according to the present invention achieves a concentration of at least 30 µg/ml in the CNS tissues and cells of the subject following administration (e.g., one week, 3 days, 48 hours, 36 hours, 24 hours, 18 hours, 12 hours, 8 hours, 6 hours, 4 hours, 3 hours, 2 hours, 1 hour, 30 minutes, or less, following intrathecal administration of the pharmaceutical composition to the subject). In certain embodiments, a therapeutic agent (e.g., a replacement enzyme) delivered according to the present invention achieves a concentration of at least 20 µg/ml, at least 15 µg/ml, at least 10 µg/ml, at least 7.5 µg/ml, at least 5 µg/ml, at least 2.5 µg/ml, at least 1.0 µg/ml or at least 0.5 µg/ml in the targeted tissues or cells of the subject (e.g., brain tissues or neurons) following administration to such subject (e.g., one week, 3 days, 48 hours, 36 hours, 24 hours, 18 hours, 12 hours, 8 hours, 6 hours, 4 hours, 3 hours, 2 hours, 1 hour, 30 minutes, or less following intrathecal administration of such pharmaceutical compositions to the subject).

Treatment of Hunter Syndrome and other Lysosomal Storage Diseases

The lysosomal storage diseases represent a group of relatively rare inherited metabolic disorders that result from defects in lysosomal function. The lysosomal diseases are characterized by the accumulation of undigested macromolecules, including those enzyme substrates, within the lysosomes (see Table 1), which results in an increase in the size and number of such lysosomes and ultimately in cellular dysfunction and clinical abnormalities.

Inventive methods described herein can advantageously facilitate the delivery of one or more therapeutic agents (e.g., one or more replacement enzymes) to targeted organelles. For example, because lysosomal storage disorders such as Hunter syndrome are characterized by an accumulation of glycosaminoglycans (GAG) in the lysosomes of affected cells, the lysosomes represent a desired target organelle for the treatment of the lysosomal storage disorders.

Inventive methods and compositions of the present invention are particularly useful for treating those diseases having a CNS etiology or component. Lysosomal storage diseases having a CNS etiology or component, include for example and without limitation Sanfilippo syndrome Type A, Sanfilippo syndrome type B, Hunter syndrome, metachromatic leukodystrophy and globoid cell leukodystrophy. Prior to the present invention, traditional therapies are limited in that they are administered to subjects intravenously, and are generally only effective in treating the somatic symptoms of the underlying enzyme deficiency. The compositions and methods of the present invention may advantageously be administered directly into the CNS of a subject suffering from a disease having such a CNS etiology thereby achieving a therapeutic concentration within the affected cells and tissues of the CNS (e.g., the brain), thus overcoming the limitations associated with traditional systemic administration of such therapeutic agents.

In some embodiments, inventive methods and compositions of the invention are useful for treating both the neurologic and the somatic sequelae or symptoms of lysosomal storage disorders. For example, some embodiments of the invention relate to compositions and methods of delivering one or more therapeutic agents to the CNS of a subject (e.g., intrathecally, intraventricularly or intracisternally) for the treatment of the CNS or neurologic sequelae and manifestations of a lysosomal storage disease, while also treating the systemic or somatic manifestations of that lysosomal storage disease. For example, some compositions of the present invention may be administered to a subject intrathecally, thereby delivering one or more therapeutic agents to the CNS of the subject and treating the neurological sequelae, coupled with the intravenous administration of one or more therapeutic agents to deliver such therapeutic agents to both the cells and tissues of the systemic circulation (e.g., cells and tissues of heart, lungs, liver, kidney or lymph nodes) to thereby treat the somatic sequelae. For example, a subject having or otherwise affected by a lysosomal storage disease (e.g., Hunter syndrome) may be administered a pharmaceutical composition comprising one or more therapeutic agents (e.g., iduronate-2-sulfatase) intrathecally at least once per week, biweekly, monthly, bimonthly or more to treat the neurologic sequelae, while a different therapeutic agent is administered to the subject intravenously on a more frequent basis (e.g., once per day, every other day, three times a week or weekly) to treat the systemic or somatic manifestations of the disease.

Hunter syndrome, or Mucopolysaccharidosis II (MPS II), is an X-linked heritable metabolic disorder resulting from a deficiency of the enzyme iduronate-2-sulfatase (I2S). I2S is localized to lysosomes and plays an important role in the catabolism of glycosaminoglycans (GAGs) heparan- and dermatan-sulfate. In the absence of enzyme, these substrates accumulate within cells, ultimately causing engorgement, followed by cellular death and tissue destruction. Due to the widespread expression of enzyme, multiple cell types and organ systems are affected in MPS II patients.

A defining clinical feature of this disorder is central nervous system (CNS) degeneration, which results in cognitive impairment (e.g., decrease in IQ). Additionally, MRI scans of affected individuals have revealed white matter lesions, dilated perivascular spaces in the brain parenchyma, ganglia, corpus callosum, and brainstem; atrophy; and ventriculomegaly (Wang et al. Molecular Genetics and Metabolism, 2009). The disease typically manifests itself in the first years of life with organomegaly and skeletal abnormalities. Some affected individuals experience a progressive loss of cognitive function, with most affected individuals dying of disease-associated complications in their first or second decade.

Compositions and methods of the present invention may be used to effectively treat individuals suffering from or susceptible to Hunter Syndrome. The terms, "treat" or "treatment," as used herein, refers to amelioration of one or more symptoms associated with the disease, prevention or delay of the onset of one or more symptoms of the disease, and/or lessening of the severity or frequency of one or more symptoms of the disease.

In some embodiments, treatment refers to partially or complete alleviation, amelioration, relief, inhibition, delaying onset, reducing severity and/or incidence of neurological impairment in a Hunter Syndrome patient. As used herein, the term "neurological impairment" includes various symptoms associated with impairment of the central nervous system (e.g., the brain and spinal cord). Symptoms of neurological impairment may include, for example, e.g., cognitive impairment; white matter lesions; dilated perivascular spaces in the brain parenchyma, ganglia, corpus callosum, and/or brainstem; atrophy; and/or ventriculomegaly, among others.

In some embodiments, treatment refers to decreased lysosomal storage (e.g., of GAG) in various tissues. In some embodiments, treatment refers to decreased lysosomal storage in brain target tissues, spinal cord neurons, and/or peripheral target tissues. In certain embodiments, lysosomal storage is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, lysosomal storage is decreased by at least 1-fold, 2-fold, 3-fold, 4-fold, 5-fold, 6-fold, 7-fold, 8-fold, 9-fold or 10-fold as compared to a control. In some embodiments, lysosomal storage is measured by the presence of lysosomal storage granules (e.g., zebra-striped morphology). The presence of lysosomal storage granules can be measured by various means known in the art, such as by histological analysis.

In some embodiments, treatment refers to reduced vacuolization in neurons (e.g., neurons containing Purkinje cells). In certain embodiments, vacuolization in neurons is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, vacuolization is decreased by at least 1-fold, 2-fold, 3-fold, 4-fold, 5-fold, 6-fold, 7-fold, 8-fold, 9-fold or 10-fold as compared to a control. The presence of and reduction of vacuolization can be measured by various means known in the art, such as by histological analysis In some embodiments, treatment refers to increased I2S enzyme activity in various tissues. In some embodiments, treatment refers to increased I2S enzyme activity in brain target tissues, spinal cord neurons and/or peripheral target tissues. In some embodiments, I2S enzyme activity is increased by about 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900% 1000% or more as compared to a control. In some embodiments, I2S enzyme activity is increased by at least 1-fold, 2-fold, 3-fold, 4-fold, 5-fold, 6-fold, 7-fold, 8-fold, 9-fold or 10-fold as compared to a control. In some embodiments, increased I2S enzymatic activity is at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg, 600 nmol/hr/mg or more. In some embodiments, I2S enzymatic activity is increased in the lumbar region or in cells in the lumbar region. In some embodiments, increased I2S enzymatic activity in the lumbar region is at least approximately 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, 10,000 nmol/hr/mg, or more. In some embodiments, I2S enzymatic activity is increased in the distal spinal cord or in cells of the distal spinal cord.

In some embodiments, treatment refers to decreased progression of loss of cognitive ability. In certain embodiments, progression of loss of cognitive ability is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, treatment refers to decreased developmental delay. In certain embodiments, developmental delay is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control.

In some embodiments, treatment refers to increased survival (e.g. survival time). For example, treatment can result in an increased life expectancy of a patient. In some embodiments, treatment according to the present invention results in an increased life expectancy of a patient by more than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200% or more, as compared to the average life expectancy of one or more control individuals with similar disease without treatment. In some embodiments, treatment according to the present invention results in an increased life expectancy of a patient by more than about 6 month, about 7 months, about 8 months, about 9 months, about 10 months, about 11 months, about 12 months, about 2 years, about 3 years, about 4 years, about 5 years, about 6 years, about 7 years, about 8 years, about 9 years, about 10 years or more, as compared to the average life expectancy of one or more control individuals with similar disease without treatment. In some embodiments, treatment according to the present invention results in long term survival of a patient. As used herein, the term "long term survival" refers to a survival time or life expectancy longer than about 40 years, 45 years, 50 years, 55 years, 60 years, or longer.

The terms, "improve," "increase" or "reduce," as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with Hunter Syndrome, who is about the same age and/or gender as the individual being treated (to ensure that the stages of the disease in the treated individual and the control individual(s) are comparable).

The individual (also referred to as "patient" or "subject") being treated is an individual (fetus, infant, child, adolescent, or adult human) having Hunter Syndrome or having the potential to develop Hunter Syndrome. The individual can have residual endogenous I2S expression and/or activity, or no measurable activity. For example, the individual having Hunter Syndrome may have I2S expression levels that are less than about 30-50%, less than about 25-30%, less than about 20-25%, less than about 15-20%, less than about 10-15%, less than about 5-10%, less than about 0.1-5% of normal I2S expression levels.

In some embodiments, the individual is an individual who has been recently diagnosed with the disease. Typically, early treatment (treatment commencing as soon as possible after diagnosis) is important to minimize the effects of the disease and to maximize the benefits of treatment.

Immune Tolerance

Generally, intrathecal administration of a therapeutic agent (e.g., a replacement enzyme) according to the present invention does not result in severe adverse effects in the subject. As used herein, severe adverse effects induce, but are not limited to, substantial immune response, toxicity, or death. As used herein, the term "substantial immune response" refers to severe or serious immune responses, such as adaptive T-cell immune responses.

Thus, in many embodiments, inventive methods according to the present invention do not involve concurrent immunosuppressant therapy (i.e., any immunosuppressant therapy used as pre-treatment/pre-conditioning or in parallel to the method). In some embodiments, inventive methods according to the present invention do not involve an immune tolerance induction in the subject being treated. In some embodiments, inventive methods according to the present invention do not involve a pre-treatment or preconditioning of the subject using T-cell immunosuppressive agent.

In some embodiments, intrathecal administration of therapeutic agents can mount an immune response against these agents. Thus, in some embodimnets, it may be useful to render the subject receiving the replacement enzyme tolerant to the enzyme replacement therapy. Immune tolerance may be induced using various methods known in the art. For example, an initial 30-60 day regimen of a T-cell immunosuppressive agent such as cyclosporin A (CsA) and an anti-proliferative agent, such as, azathioprine (Aza), combined with weekly intrathecal infusions of low doses of a desired replacement enzyme may be used.

Any immunosuppressant agent known to the skilled artisan may be employed together with a combination therapy of the invention. Such immunosuppressant agents include but are not limited to cyclosporine, FK506, rapamycin, CTLA4-Ig, and anti-TNF agents such as etanercept (see e.g. Moder, 2000, Ann. Allergy Asthma Immunol. 84, 280-284; Nevins, 2000, Curr. Opin. Pediatr. 12, 146-150; Kurlberg et al., 2000, Scand. J. Immunol. 51, 224-230; Ideguchi et al., 2000, Neuroscience 95, 217-226; Potter et al., 1999, Ann. N.Y. Acad. Sci. 875, 159-174; Slavik et al., 1999, Immunol. Res. 19, 1-24; Gaziev et al., 1999, Bone Marrow Transplant. 25, 689-696; Henry, 1999, Clin. Transplant. 13, 209-220; Gummert et al., 1999, J. Am. Soc. Nephrol. 10, 1366-1380; Qi et al., 2000, Transplantation 69, 1275-1283). The anti-IL2 receptor (.alpha.-subunit) antibody daclizumab (e.g. Zenapax™), which has been demonstrated effective in transplant patients, can also be used as an immunosuppressant agent (see e.g. Wiseman et al., 1999, Drugs 58, 1029-1042; Beniaminovitz et al., 2000, N. Engl J. Med. 342, 613-619; Ponticelli et al., 1999, Drugs R. D. 1, 55-60; Berard et al., 1999, Pharmacotherapy 19, 1127-1137; Eckhoff et al., 2000, Transplantation 69, 1867-1872; Ekberg et al., 2000, Transpl. Int. 13, 151-159). Additional immunosuppressant agents include but are not limited to anti-CD2 (Branco et al., 1999, Transplantation 68, 1588-1596; Przepiorka et al., 1998, Blood 92, 4066-4071), anti-CD4 (Marinova-Mutafchieva et al., 2000, Arthritis Rheum. 43, 638-644; Fishwild et al., 1999, Clin. Immunol. 92, 138-152), and anti-CD40 ligand (Hong et al., 2000, Semin. Nephrol. 20, 108-125; Chirmule et al., 2000, J. Virol. 74, 3345-3352; Ito et al., 2000, J. Immunol. 164, 1230-1235).

Administration

Inventive methods of the present invention contemplate single as well as multiple administrations of a therapeutically effective amount of the therapeutic agents (e.g., replacement enzymes) described herein. Therapeutic agents (e.g., replacement enzymes) can be administered at regular intervals, depending on the nature, severity and extent of the subject's condition (e.g., a lysosomal storage disease). In some embodiments, a therapeutically effective amount of the therapeutic agents (e.g., replacement enzymes) of the present invention may be administered intrathecally periodically at regular intervals (e.g., once every year, once every six months, once every five months, once every three months, bimonthly (once every two months), monthly (once every month), biweekly (once every two weeks), weekly, daily or continuously).

In some embodiments, intrathecal administration may be used in conjunction with other routes of administration (e.g., intravenous, subcutaneously, intramuscularly, parenterally, transdermally, or transmucosally (e.g., orally or nasally)). In some embodiments, those other routes of administration (e.g., intravenous administration) may be performed no more frequent than biweekly, monthly, once every two months, once every three months, once every four months, once every five months, once every six months, annually administration. In some embodiments, the method further comprises administering the I2S replacement enzyme intravenously to the subject. In certain embodiments, the intravenous administration is no more frequent than weekly administration (e.g., no more frequent than biweekly, monthly, once every two months, once every three months, once every four months, once every five months, or once every six months). In certain embodiments, the intraveneous administration is more frequent than monthly administration, such as twice weekly, weekly, every other week, or twice monthly. In some embodiments, intraveneous and intrathecal administrations are performed on the same day. In some embodiments, the intraveneous and intrathecal administrations are not performed within a certain amount of time of each other, such as not within at least 2 days, within at least 3 days, within at least 4 days, within at least 5 days, within at least 6 days, within at least 7 days, or within at least one week. In some embodiments, intraveneous and intrathecal administrations are performed on an alternating schedule, such as alternating administrations weekly, every other week, twice monthly, or monthly. In some embodiments, an intrathecal administration replaces an intravenous administration in an administration schedule, such as in a schedule of intraveneous administration weekly, every other week, twice monthly, or monthly, every third or fourth or fifth administration in that schedule can be replaced with an intrathecal administration in place of an intraveneous administration. In some embodiments, an intravenous administration replaces an intrathecal administration in an administration schedule, such as in a schedule of intrathecal administration weekly, every other week, twice monthly, or monthly, every third or fourth or fifth administration in that schedule can be replaced with an intravenous administration in place of an intrathecal administration. In some embodiments, intraveneous and intrathecal administrations are performed sequentially, such as performing intraveneous administrations first (e.g., weekly, every other week, twice monthly, or monthly dosing for two weeks, a month, two months, three months, four months, five months, six months, a year or more) followed by intrathecal administrations (e.g., weekly, every other week, twice monthly, or monthly dosing for more than two weeks, a month, two months, three months, four months, five months, six months, a year or more). In some embodiments, intrathecal administrations are performed first (e.g., weekly, every other week, twice monthly, monthly, once every two months, once every three months dosing for two weeks, a month, two months, three months, four months, five months, six months, a year or more) followed by intraveneous administations (e.g., weekly, every other week, twice monthly, or monthly dosing for more than two weeks, a month, two months, three months, four months, five months, six months, a year or more).

In some embodiments, Hunter Syndrome is associated with peripheral symptoms and the method includes administering the replacement enzyme intrathecally but does not involve administering the replacement enzyme intravenously to the subject. In certain embodiments, the intrathecal administration of the I2S enzyme amelioriates or reduces one or more of the peripherial symptoms associated with the subject's I2S deficiency As used herein, the term "therapeutically effective amount" is largely determined base on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). For example, a therapeutically effective amount may be an amount sufficient to achieve a desired therapeutic and/or prophylactic effect, such as an amount sufficient to modulate lysosomal enzyme receptors or their activity to thereby treat such lysosomal storage disease or the symptoms thereof (e.g., a reduction in or elimination of the presence or incidence of "zebra bodies" or cellular vacuolization following the administration of the compositions of the present invention to a subject). Generally, the amount of a therapeutic agent (e.g., a recombinant lysosomal enzyme) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

In some embodiments, the therapeutically effective dose ranges from about 0.005 mg/kg brain weight to 500 mg/kg brain weight, e.g., from about 0.005 mg/kg brain weight to 400 mg/kg brain weight, from about 0.005 mg/kg brain weight to 300 mg/kg brain weight, from about 0.005 mg/kg brain weight to 200 mg/kg brain weight, from about 0.005 mg/kg brain weight to 100 mg/kg brain weight, from about 0.005 mg/kg brain weight to 90 mg/kg brain weight, from about 0.005 mg/kg brain weight to 80 mg/kg brain weight, from about 0.005 mg/kg brain weight to 70 mg/kg brain weight, from about 0.005 mg/kg brain weight to 60 mg/kg brain weight, from about 0.005 mg/kg brain weight to 50 mg/kg brain weight, from about 0.005 mg/kg brain weight to 40 mg/kg brain weight, from about 0.005 mg/kg brain weight to 30 mg/kg brain weight, from about 0.005 mg/kg brain weight to 25 mg/kg brain weight, from about 0.005 mg/kg brain weight to 20 mg/kg brain weight, from about 0.005 mg/kg brain weight to 15 mg/kg brain weight, from about 0.005 mg/kg brain weight to 10 mg/kg brain weight.

In some embodiments, the therapeutically effective dose is greater than about 0.1 mg/kg brain weight, greater than about 0.5 mg/kg brain weight, greater than about 1.0 mg/kg brain weight, greater than about 3 mg/kg brain weight, greater than about 5 mg/kg brain weight, greater than about 10 mg/kg brain weight, greater than about 15 mg/kg brain weight, greater than about 20 mg/kg brain weight, greater than about 30 mg/kg brain weight, greater than about 40 mg/kg brain weight, greater than about 50 mg/kg brain weight, greater than about 60 mg/kg brain weight, greater than about 70 mg/kg brain weight, greater than about 80 mg/kg brain weight, greater than about 90 mg/kg brain weight, greater than about 100 mg/kg brain weight, greater than about 150 mg/kg brain weight, greater than about 200 mg/kg brain weight, greater than about 250 mg/kg brain weight, greater than about 300 mg/kg brain weight, greater than about 350 mg/kg brain weight, greater than about 400 mg/kg brain weight, greater than about 450 mg/kg brain weight, greater than about 500 mg/kg brain weight.

In some embodiments, the therapeutically effective dose may also be defined by mg/kg body weight. As one skilled in the art would appreciate, the brain weights and body weights can be correlated. Dekaban A S. "Changes in brain weights during the span of human life: relation of brain weights to body heights and body weights," Ann Neurol 1978; 4:345-56. Thus, in some embodiments, the dosages can be converted as shown in Table 5.

TABLE 5

Correlation between Brain Weights, body weights and ages of males

| Age (year) | Brain weight (kg) | Body weight (kg) |
|---|---|---|
| 3 (31-43 months) | 1.27 | 15.55 |
| 4-5 | 1.30 | 19.46 |

In some embodiments, the therapeutically effective dose may also be defined by mg/15 cc of CSF. As one skilled in the art would appreciate, therapeutically effective doses based on brain weights and body weights can be converted to mg/15 cc of CSF. For example, the volume of CSF in adult humans is approximately 150 mL (Johanson C E, et al. "Multiplicity of cerebrospinal fluid functions: New challenges in health and disease," Cerebrospinal Fluid Res. 2008 May 14; 5:10). Therefore, single dose injections of 0.1 mg to 50 mg protein to adults would be approximately 0.01 mg/15 cc of CSF (0.1 mg) to 5.0 mg/15 cc of CSF (50 mg) doses in adults.

It is to be further understood that for any particular subject, specific dosage regimens should be adjusted over time according to the individual need and the professional judgment of the person administering or supervising the administration of the enzyme replacement therapy and that dosage ranges set forth herein are exemplary only and are not intended to limit the scope or practice of the claimed invention.

Kits

The present invention further provides kits or other articles of manufacture which contains the formulation of the present invention and provides instructions for its reconstitution (if lyophilized) and/or use. Kits or other articles of manufacture may include a container, an IDDD, a catheter and any other articles, devices or equipment useful in interthecal administration and associated surgery. Suitable containers include, for example, bottles, vials, syringes (e.g., pre-filled syringes), ampules, cartridges, reservoirs, or lyo-jects. The container may be formed from a variety of materials such as glass or plastic. In some embodiments, a container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may holds formulations and a label on, or associated with, the container that may indicate directions for reconstitution and/or use. For example, the label may indicate that the formulation is reconstituted to protein concentrations as described above. The label may further indicate that the formulation is useful or intended for, for example, IT administration. In some embodiments, a container may contain a single dose of a stable formulation containing a therapeutic agent (e.g., a replacement enzyme). In various embodiments, a single dose of the stable formulation is present in a volume of less than about 15 ml, 10 ml, 5.0 ml, 4.0 ml, 3.5 ml, 3.0 ml, 2.5 ml, 2.0 ml, 1.5 ml, 1.0 ml, or 0.5 ml. Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration in the reconstituted formulation will generally be at least 1 mg/ml (e.g., at least 5 mg/ml, at least 10 mg/ml, at least 25 mg/ml, at least 50 mg/ml, at least 75 mg/ml, at least 100 mg/ml). Kits or other articles of manufacture may further include other materials desirable from a commercial and user standpoint, including other buffers, diluents, filters, needles, IDDDs, catheters, syringes, and package inserts with instructions for use.

The invention will be more fully understood by reference to the following examples. They should not, however, be construed as limiting the scope of the invention. All literature citations are incorporated by reference.

EXAMPLES

Example 1

Biodistribution

The major objective of this study was to determine whether recombinant human I2S could be delivered to the brain of adult MPS II mice by the intrathecal-lumbar route

TABLE 6

Six groups of 8-12 week old male mice were treated as follows:

| Group | N | Strain | Treatment | Volume | Dose | Dose/Brain weight | Route |
|---|---|---|---|---|---|---|---|
| A | 3 | IKO | I2S | 10 µL | 260 µg | 520 mg/kg | IT-lumbar |
| B | 3 | IKO | I2S | 10 µL | 260 µg | 520 mg/kg | IT-lumbar |
| C | 3 | IKO | Untreated | N/A | N/A | N/A | N/A |
| D | 1 | IKO | I2S | 10 µL | 260 µg | 520 mg/kg | IT-lumbar |
| E | 3 | IKO | Untreated | N/A | N/A | N/A | N/A |
| F | 3 | C57B1/6 | Untreated | N/A | N/A | N/A | N/A |

Injection schedule: Animals received up to 3 injections of idursulfase (10 L) via the intrathecal-lumbar route:
Groups A & D: Administered 3 doses of I2S on days 1, 8, and 15
Group B: Administered 2 doses of I2S on days 1 and 8
Groups C & E: Untreated control (IKO) mice
Group F: Untreated wild-type control mice Materials and Methods Animals:

Mice were housed in groups of up to 4 per cage in a colony room under a 12-hour light-dark cycle. Rodent diet (LabDiet-5001, St Louis, Mo.) and water (Lexington, Mass. municipal water purified by reverse osmosis) was available ad libitum for the duration of the experiment. Care of animals was conducted in accordance with the guidelines described in the Guide for the Care and Use of Laboratory Animals (National Academy Press, Washington D.C., 1996). The current IKO breeding colony was established from four carrier female mice heterozygous for the IKO mutation that were obtained from Dr. Joseph Muenzer (University of North Carolina). Carrier females were bred with male mice of the C57BL/6 background strain (C57BL/6NTac, Taconic, Hudson, N.Y.), producing heterozygous females and hemizygous male knockout mice, as well as wild-type male and female littermates. All offspring were genotypes by PCR analysis of tissue DNA. All mice used in this experiment were males identified as either hemizygous IKO (−/0) or wild-type (WT) littermate (+/0) mice between 8 and 12 weeks of age.

Idursulfase:

Twenty-two mL I2S [Recombinant human idursufase was dialyzed against four changes of 2 L phosphate buffered saline (PBS). The I2S was then concentrated by Vivaspin column and resuspended in a final volume of 1 mL PBS, followed by filter sterilization using a 0.2 µm filter. The final concentration was 51 mg/mL.

Intrathecal-Lumbar Injections:

Adult mice were anesthetized using 1.25% 2,2,2 tribromoethanol (Avertin) at 200-300 µL/10 grams body weight (250-350 mg/kg) by intraperitoneal injection. Dorsal hair was removed between the base of the tail and the shoulder blades and the shaved area was swabbed with povidine/betadine scrub followed by isopropyl alcohol. A small midline skin incision (1-2 cm) was made over the lumbosacral spine and the intersection of the dorsal midline and the cranial aspect of the wings of the ilea (singular ileum) identified. The muscle in the iliac fossa (gluteus medius) is a heart shaped muscle and the two sides of the top of the "heart" approximate the location of the wings of the ilea. A 32 gauge needle attached to a gas tight 10-20 μL glass Hamilton syringe was inserted until resistance was felt from the underlying bone. Injection of 10 μL of test article at an approximate rate of 2 μL/20 seconds (10 μL/2 minutes) was performed. The skin incision was closed using wound clips as appropriate and the animal was allowed to recover in a recovery chamber before being returned to the appropriate cage.

Histology Procedures:

Animals were sacrificed at one hour after the final injection.

Brain and liver tissues were collected and fixed in 10% neutral buffered formalin, then processed and embedded in paraffin. Five μm sections were prepared for hematoxylin/eosin (H&E) and immunohistochemistry (IHC) staining Hematoxylin and Eosin Staining:

Brain and liver sections were stained with H&E. The staining results showed nuclei as purple and cytoplasm as pink to red. H&E stained slides were used for histopathological morphology evaluation.

Immunohistochemistry:

For I2S biodistribution evaluation, deparaffinized and rehydrated brain and liver sections were incubated overnight with mouse monoclonal antibody 2C4-2B2 (Maine Biotechnology Services, Portland, Me.) against recombinant human I2S to detect injected I2S (or an irrelevant mouse IgG as a negative control antibody; Vector Laboratories, Burlingame, Calif.). Following an overnight incubation at 2-8° C., a secondary goat anti-mouse IgG conjugated with horseradish peroxidase was added. After additional 30 minutes of incubation at 37° C., Tyramide-Alexa Fluor 488 labeling solution (Invitrogen Corp., Carlsbad, Calif.) was added for an additional 10 minutes. Sections were coverslipped using an antifading mounting medium (VectaShield; Vector Laboratories) containing 1.5 μg/ml 4'-6-diamidino-2-phenylindole (DAPI) as a nuclear counterstain and observed with a multiple channel Nikon fluorescent microscope. The staining results showed I2S positive cells as green, with nuclei as blue, and background areas as black.

For efficacy analysis, brain and liver sections were stained with a rat anti-LAMP-1 (lysosomal associated membrane protein as a lysosomal marker) IgG (Santa Cruz Biotechnology, Santa Cruz, Calif.) as the primary antibody. A rat IgG as an irrelevant antibody was used as negative control. The ABC (avidin biotin complex kits from Vector Labs, Burlingame, Calif.) method was used to amplify the targeted marker.

Briefly, deparaffinized sections were rehydrated and incubated with the primary antibody. Following overnight incubation at 2-8° C., a secondary biotinylated rabbit anti-rat IgG (Vector Labs, Burlingame, Calif.) was added and incubated 30 minutes at 37° C., then samples were washed and treated with avidin-biotin-peroxidase complex (Vector Laboratories) for 30 minutes. For color development, 3,3'-diaminobenzidine tetrahydrochloride (DAB) was used as the chromagen. Sections were then counterstained with hematoxylin and coverslipped. The staining results showed LAMP-1 positive cells as brown and nuclei as blue.

The representative photos were taken and the area of LAMP-1 positive cells was analyzed with Image-Pro Plus software (Media Cybernetics, Inc., Bethesda, Md.) and comparative statistics were performed using student's t-test.

Electron Microscope Method:

Brain tissues from 3 doses of I2S treated animals were fixed in 2.5% PFA/2.5% glutaraldehyde in 0.1M sodium cacodylate buffer pH 7.4 at 4 degrees for over night. Then the samples were washed in cacodylate buffer (0.1M, pH7.4) and post-fixed in osmium tetroxide, dehydrated in alcohols and propylene oxide and embedded in Epon resin. Ultrathin sections were cut at 100 nm, stained with lead citrate and examined in a Tecnai™ $G^2$ Spirit BioTWIN transmission electron microscope.

Results

Figure 1:
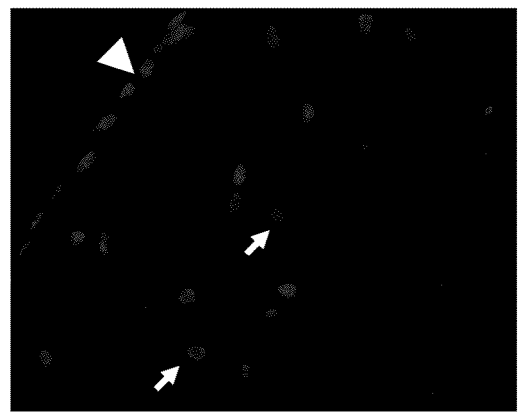
FIG. 1 is an exemplary illustration showing IT-delivered I2S detected in the neurons (arrows) of the cerebral cortex and the cerebellar cortex including I2S in a layer of meningeal cells covering the surface of the brain (arrow heads) following intrathecal injections of 3 doses of I2S. Staining of I2S IHC in 2 dose injected brains was weaker (photo not shown). No positive I2S staining was observed for any type of cells in the brain of vehicle control animals. 40×.
Figure 1:
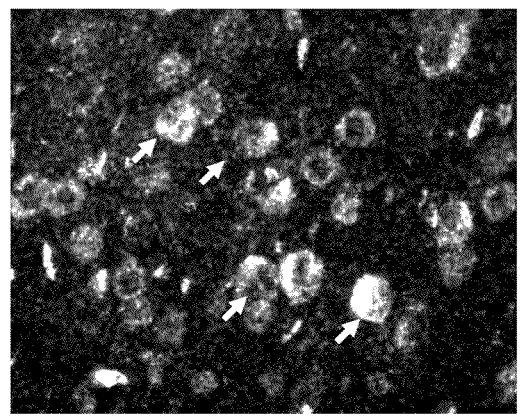
Figure 1:
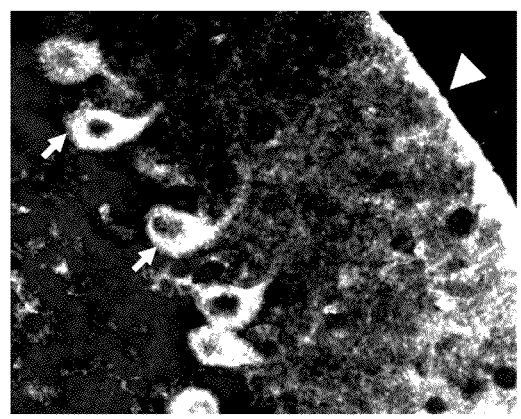

In the brain as determined by immunohistochemistry (IHC), no I2S was found in vehicle control animals. In contrast, meningeal cells, neurons of the cerebrum and cerebellum were positively stained for I2S in I2S injected animals. The staining signal was stronger in animals administered 3 doses (FIG. 1).

Figure 2:
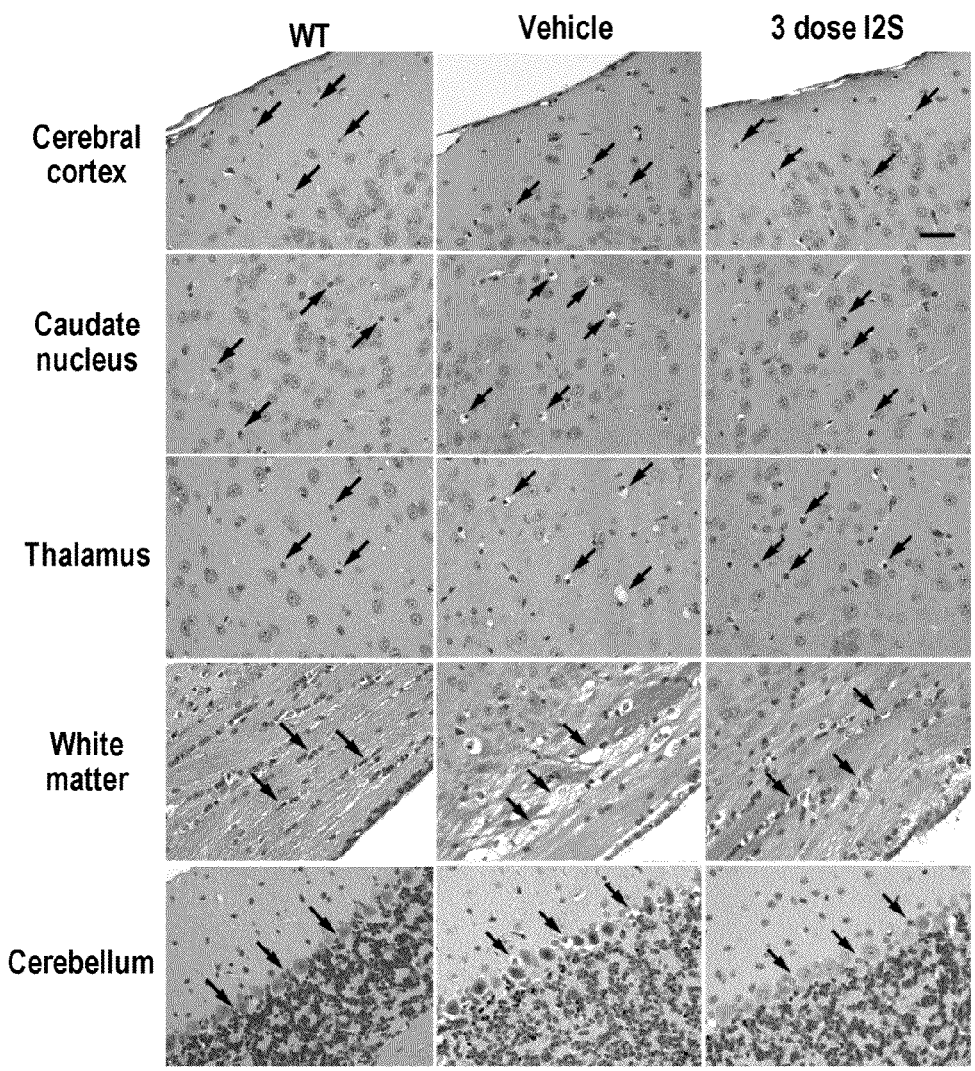
FIG. 2 is an exemplary illustration showing reversal of pathology in the brain of I2S knock-out (IKO) mice after intrathecal-lumbar I2S injection. H&E stained brain tissues showed numerous cellular storage vacuoles (arrows) in the vehicle control animals. Cellular vacuolation was reduced throughout the brain in both 2 dose (photo not shown) and 3 dose injected mice. Marked reduction was found in the 3 dose injected ones. 40×.
Figure 3:
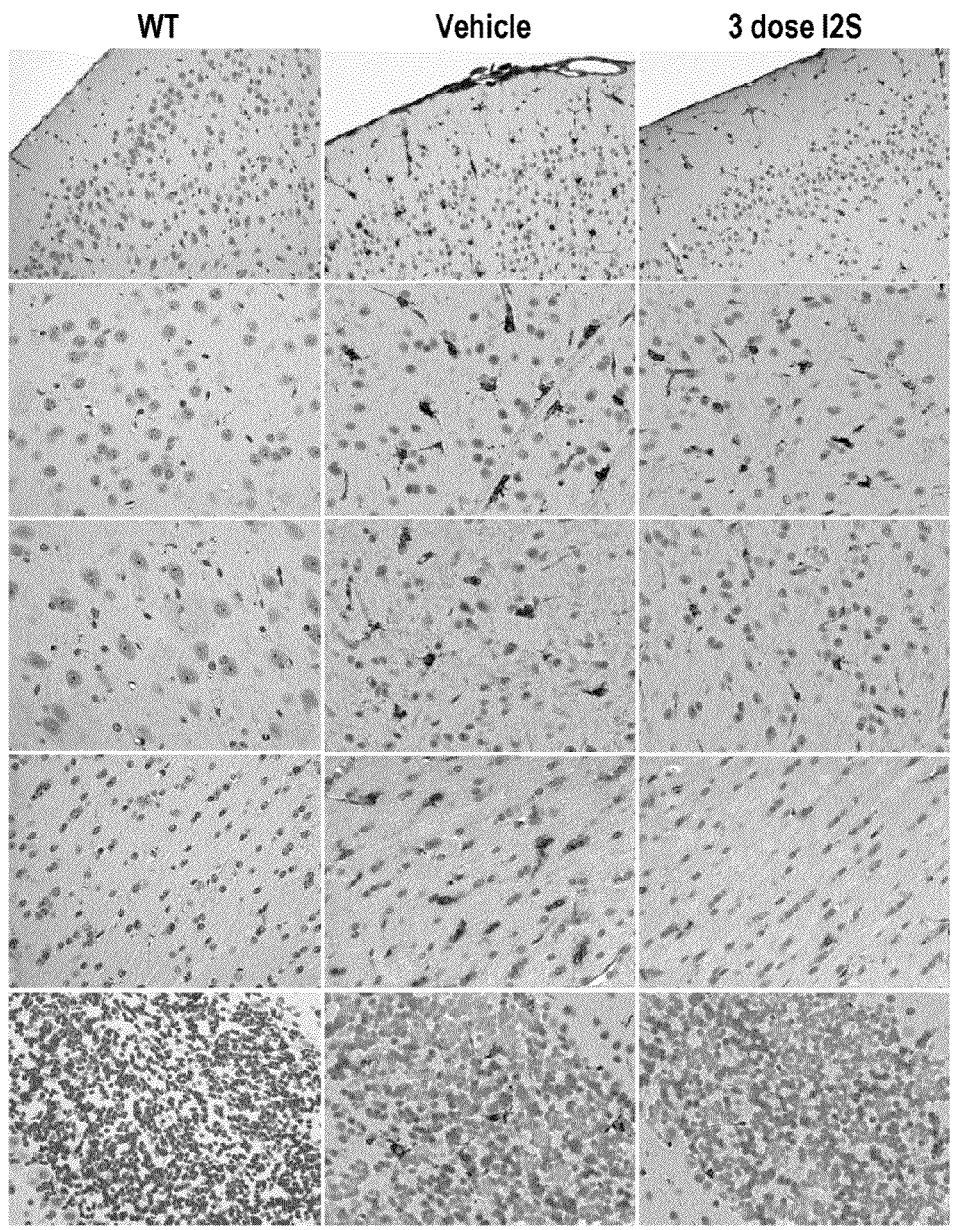
FIG. 3 is an exemplary illustration showing immunohistochemical staining of LAMP-1, where there is a marked reduction of lysosomal activity in the brains after 2 doses (photo not shown) and 3 doses of I2S treatment compared with vehicle controlled mice. The reduction was characterized by the decrease in the number of LAMP-1 positive cells and lighter staining intensity in the regions throughout the brain. 40×.
Figure 4:
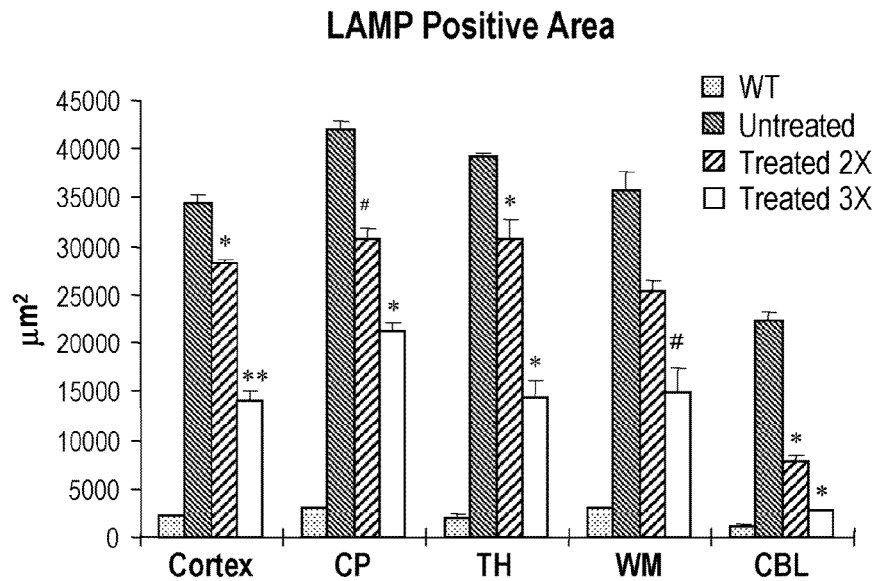
FIG. 4 is an exemplary illustration showing morphometry results from a comparison of the mean LAMP-1 positive area among wild-type (WT), vehicle untreated and I2S (2 and 3 doses) mice in the cerebral cortex (Cortex), caudate nucleus (CP), thalamus (TH), white matter (WM) and cerebellum (CBL) confirmed that there were significant reductions in the LAMP-1 positive staining in all areas of the brain evaluated. Data are represented as the mean±s.d. # P<0.05; * P<0.01; ** P<0.001.

In brain tissues of vehicle-treated IKO mice, cellular vacuolation, a histopathological hallmark of lysosomal storage diseases, was found throughout brains compared to wild type animals. In I2S treated IKO mice, there was widespread reduction of cellular vacuolation from the surface cerebral cortex, caudate nucleus, thalamus, cerebellum, to the white matter compared to untreated ones (FIG. 2). Abnormally high lysosomal activity was found by lysosomal-associated membrane protein-1 (LAMP-1) staining, an indicator of lysosomal activity and disease state, in microglial, meningeal and perivascular cells of vehicle-treated IKO mice when compared to wild type animals. The I2S intrathecal-treated mice had marked reductions in LAMP-1 immunostaining. This reduction was characterized by the decrease in the number of LAMP-1 positive cells and lighter staining The reduction was found throughout whole brain from the surface cerebral cortex, caudate nucleus, thalamus, cerebellum to white matter (FIG. 3) in both 2 and 3 dose of I2S treated animals. Morphometrical analysis of LAMP-1 immunostaining of various brain regions confirmed that there were significant reductions in the LAMP-1 positive staining in all areas of the brain evaluated (FIG. 4).

Electron microscopy examination of brain cells in vehicle-treated IKO mice revealed the enlarged vacuoles containing amorphous granular storage material and inclusions with lamellated and zebra body-like structures. These typical pathological features of lysosomal storage at the ultrastructural level were reduced in I2S intrathecal-lumbar injected mice (FIG. 5).

In the liver, there was no positive staining of I2S in the vehicle treated animals. In the I2S intrathecal injected mice, a large amount of injected I2S was clearly found in sinusoidal cells (FIG. 6), which indicated the injected I2S within the intrathecal space circulated with CSF and was then absorbed through the arachnoid granulations into the circulatory system.

In liver tissues of vehicle-treated IKO mice, severe cellular vacuolation and abnormally high lysosomal activity demonstrated by H&E staining and strong LAMP-1 immunostaining were found compared to WT mice. Marked reduction of cellular vacuolation and LAMP-1 immunostaining in livers was found after intrathecal treatment with I2S. H&E staining revealed intracytoplasmic vacuolization was almost completely disappear with a nearly normal liver cell structure (FIG. 7).

In IKO mice, recombinant human I2S was delivered to the brain by the intrathecal-lumbar route and injected I2S cause widespread histopathological improvement in a variety of regions in the brain.

Injected I2S was detected in meningeal cells and neurons in the brain.

Reduced cellular vacuolation throughout the brain at both light and electron microscopy levels.

Reduced LAMP-1 lysosomal marker throughout the brain.

Intrathecal injected I2S entered the peripheral circulation and improved liver morphology and histological marker.

Example 2

Toxicology

This example illustrates the clinical signs associated with idursulfase via monthly bolus intrathecal lumbar doses in cynomolgus monkeys. To achieve this, 14 male, cynomolgus monkeys were randomly assigned to five treatment groups as shown in the following table.

TABLE 7

EXPERIMENTAL DESIGN

| Group | Number of Animals | Nominal Dose (mg) | Dose Volume (ml) |
|---|---|---|---|
| 1 | 3 | 0 | 1 |
| 2 | 3 | 3 | 1 |
| 3 | 3 | 30 | 1 |
| 4 | 3 | 150 | 1 |
| 5 | 2 | 100 | 1 |

Animals in all groups were dosed three times at monthly intervals IT at the level of the lumbar spine. The 1 ml dose volume was flushed from the catheter system with 0.3 ml of PBS. One to two days prior to each dosing, approximately 2 ml of CSF was collected from an IT spinal tap at the level of the cisterna magna. Blood samples (2 ml) were also collected at this time. Blood (2 ml) and CSF (0.1 ml) were collected from Group 5 animals predose, 0.5, 1, 2, 4, 8, 24, and 48 hours post dose after the first dose. Clinical signs were recorded at least twice daily. A necropsy was performed approximately 24 hours after the third dose and selected tissues were harvested and saved.

On Day 1, all three Group 4 (150 mg) animals exhibited minimal tending to hind quarters within 3-12 minutes post dose, lasting 5-15 minutes; this sign was deemed related to the test article. There were no changes in body weight, food consumption and neurological/physical examination parameters that were considered related to the test article.

The analysis of the serum and CSF samples and the dosing solution analyses are presented. Variations in endogenous idursulfase activity were observed in different tissues from the cynomolgus monkey; brain and spinal cord had greater endogenous activity than other peripheral organs examined, including liver, heart, and kidney. Idursulfase administration was associated with dose-dependent increases in idursulfase activity in various brain regions, as well as in the brainstem and spinal cord. IT delivery did not result in an observable difference in distribution between the right and left cerebral hemispheres. There was a clear dose-dependent increase in idursulfase activity in the following organs: brain, liver, heart, and kidney. Immunostaining for idursulfase in the brain demonstrated a dose-dependent increase in staining intensity. In the 3 mg group, meningial cell and limited glial cell staining beneath the meninges was observed; neuronal staining was not evident in animals from the 3 mg treatment group. Idursulfase staining was positive and dose dependent in the spinal cord, with the highest staining intensity in the lumbar region, where IT administration of idursulfase occurred. Idursulfase staining intensity in liver, kidney, and heart was dose-dependent and consistent with increased idursulfase activity in these organs.

In conclusion, IT administration of idursulfase at doses up to 150 mg delivered at monthly intervals had no adverse effects. Thus, the no observed adverse effect level (NOAEL) was interpreted to be 150 mg, the highest dose tested in this study. Idursulfase administration was associated with dose-dependent increases in idursulfase activity in the CNS and resulted in systemic I2S levels and activity in the liver, kidney, and heart.

The test article, idursulfase, was supplied as dosing solutions in 154 mM NaCl, 0.005% Polysorbate 20, pH 5.3-6.1. The nominal concentrations of the supplied dosing solutions were 0, 3, 30 or 150 mg/ml. The test article was stored in a freezer at −82° to −79° C. Phosphate buffered saline (PBS), pH 7.2, was used as a flushing agent after the doses were administered and after serial CSF collections. The PBS was obtained from Gibco, Invitrogen Corporation.

Test Article Dosing Preparation

On the first day of dosing for each time interval, one vial of each concentration was removed from the −80° C. chest freezer and allowed to thaw on the countertop to room temperature. Once thawed, the vials for Groups 1, 2, and 3 were labeled, weighed and 1 ml was withdrawn through a 0.22 μm filter for each animal scheduled for dosing. After all of the doses were administered, the vials were reweighed and placed in the refrigerator.

The following day (day of dosing for Animal 003, Group 4, and Group 5) dosing solutions for Groups 1 and 4 were removed from the refrigerator and placed on the countertop to reach room temperature. Once room temperature was obtained, the vials for Groups 1 and 4 were weighed, Group 4 vial was labeled, and 1 ml was withdrawn through the filter for each animal scheduled for dosing in Groups 1 and 4. The dosing solution for Group 5 was then prepared by injecting the appropriate amount of Group 4 dosing solution and Group 1 (vehicle) into a sterile polypropylene vial. The amount added from Groups 1 and 4 were recorded. The solution was mixed by gently inverting the vial and 2-1 ml doses were withdrawn through the filter for the animals in Group 5. The vials for Groups 1 and 4 were reweighed upon completion of dosing and all the vials (Groups 1-5) were placed in a freezer.

Fourteen animals were randomly assigned to treatment groups as described in the following Table.

The IT route of administration was selected because this is an intended route for human administration. The doses of idursulfase that were selected for this study (3, 30, 100, and 150 mg/ml) were chosen to assess the biodistribution of varying doses levels of enzyme within the non-human primate central nervous system (CNS) after three consecutive monthly bolus IT lumbar injections.

Clinical Observations

The overall incidence of clinical signs was minimal. None of the animals in Group 1 (control), Group 2 (3 mg), Group 3 (30 mg), or Group 5 (100 mg) had clinical signs that were considered related to the test article at any time during the study.

On Day 1, all three Group 4 (150 mg) animals (012-014) exhibited minimal tending to hind quarters within 3-12 minutes post dose, lasting 5-15 minutes. This sign was considered related to the test article and was not observed in any of the lower dose groups. There were no other clinical signs immediately after the first dose or on the days immediately following test article administration. The only other sign observed for the Group 4 animals was a single episode of emesis for Animal 013 on Day 35.

Administration of the test article as a single, monthly intrathecal bolus was not associated with any adverse gross or microscopic change when taking into consideration the changes inherent with an implanted drug delivery device. All groups, including the control group, had microscopic changes in the meninges indicating inflammatory reactions to the drug delivery system. In the animals that received doses of the test article of 30 mg and greater, there was a tendency for the inflammatory reaction in the meninges to have a more pronounced eosinophilic component.

Because the differences between the control and test article treated animals were so slight, the no observed adverse effect level (NOAEL) was interpreted to be 150 mg, the highest dose tested in this study.

The overall inflammatory reaction in the meninges in all groups (including controls) was slightly more pronounced than generally encountered in an intrathecal study of this duration in monkeys. However, this was considered to possibly be related to some characteristic of the vehicle or to the act of dosing 24 hours prior to necropsy.

Brain idursulfase staining was positive in all treated animals except one animal in the 3 mg group, with the highest staining intensity found in the 150 mg group (FIGS. 16, 17, 18 and 19). In the 3 mg group, only meningial cells and a few glial cells beneath the meninges were positive; no injected idursulfase was detected in neurons. In the higher dose groups (30, 100 and 150 mg), large populations of cerebral neurons were strongly positive for idursulfase staining, along with meningial cells, glial cells and perivascular cells. Idursulfase immunostaining revealed a wide distribution of injected idursulfase in cerebral neurons from the neurons within layer I at the surface near the meninges, to the ones within the deeper layer VI adjacent to the white matter (FIGS. 20, 21 and 22). Marked staining of neurons was also observed for the 150 mg dose group (FIG. 23). In all animals (dose group from 30-150 mg), no marked difference in the neuronal idursulfase staining was found between frontal, middle, and rear sections of the brain.

Idursulfase staining was positive in the spinal cords of all animals, with the highest staining intensity in the lumbar region (FIGS. 24 and 25). Idursulfase immunostaining was also dose dependent. Neurons, meningial cells, glial cells, perivascular cells and epi/peri/endoneurium (connective cells) surrounding nerve fibers were strongly positive for idursulfase staining in the 150 mg group (FIGS. 26 and 27).

In the liver, positive staining for idursulfase was found in sinusoidal cells (Kupffer cells and endothelial cells) of all animals. Idursulfase, however, was not detected in hepatocytes for the 3 mg treatment group (FIG. 28), while positive idursulfase staining in the hepatocytes was found in the higher dose groups, with the greatest staining intensity in the 150 mg treatment group (FIGS. 29, 30 and 31).

There was no positive staining for idursulfase in animals from the 3 mg treatment group (FIG. 22). In contrast, interstitial cells were positively stained for idursulfase in the 30, 100 and 150 mg groups, with marked staining being observed in the 150 mg group—in terms of positive cell number and staining intensity (FIGS. 33, 34 and 35).

Kidney

Little or no injected idursulfase was detected in animals from the 3 mg dose group (FIG. 36). Positive idursulfase staining, however, was found in the glomerular cells and interstitial cells in the 30 and 100 mg groups (FIGS. 37 and 38). In the 150 mg group, idursulfase immunostaining additionally revealed idursulfase staining of proximal tubular cells, along with marked staining of glomerular and interstitial cells (FIG. 39).

Discussion

There were no test article-related clinical signs or effects on body weight, food consumption, physical examination findings and neurological examination findings. On Day 1, the Group 4 (150 mg) animals exhibited minimal tending to hind quarters within 3-12 minutes post dosing, lasting 5 to 15 minutes; this sign was judged to be related to the test article.

Idursulfase administration was associated with dose-dependent increases in idursulfase activity in various brain regions, as well as the brain stem and spinal cord. The highest level of staining intensity in the spinal cord was in the lumbar region, where IT administration of idursulfase occurred. IT administration of idursulfase also resulted in systemic exposure with dose-dependent staining intensity in the liver, kidney, and heart. Animals that received doses of the test article at 30 mg and greater had a tendency for the inflammatory reaction in the meninges to have a more pronounced eosinophilic component, but this difference was not considered biologically significant.

IT administration of idursulfase at doses up to 150 mg delivered at monthly intervals had no adverse effects. Thus, the no observed adverse effect level (NOAEL) was interpreted to be 150 mg, the highest dose tested in this Example. Idursulfase administration was associated with dose-dependent increases in idursulfase activity in the CNS and resulted in systemic levels in the liver, kidney, and heart.

Example 3

PK (Serum and CSF) of IT Delivered I2S

This example provides serum and cerebrospinal fluid (CSF) analysis associated with a 6-Month Toxicity Study of Idursulfase Administered Via Monthly Bolus Intrathecal Lumbar Injections and Weekly Bolus Intravenous Injections in Cynomolgus Monkeys" for test article (TA) concentration.

Experimental Design

The objective of this study was to evaluate repeat dose intrathecal (IT) administration of idursulfase (12 s) from a toxicology and safety pharmacology perspective over a six month period. The study design is shown in Table 8.

TABLE 8

STUDY DESIGN

| Group No. | Number of Animals | IV Dose (mg/kg) | No. of IV Doses | IT Dose (mg) | No. of IT Doses |
|---|---|---|---|---|---|
| 1 | 6 | DC (saline) | 23 | DC (PBS) | 6 |
| 2 | 12 | 0 (IV vehicle) | 23 | 0 (IT vehicle) | 6 |
| 3 | 12 | 0.5 | 23 | 3 | 6 |
| 4 | 6 | 0.5 | 23 | 30 | 6 |
| 5 | 12 | 0.5 | 23 | 100 | 6 |

DC = Device Control; Animals In group 1 not dosed with vehicles or test article

Test Article
Identification: idursulfase IV Dosing—(2.0 mglmL)
IT Dosing
  idursulfase (0 mglmL)
  idursulfase (3 mglmL)
  idursulfase (30 mg/ml)
  idursulfase (100 mg/ml)
Assay Methods:
  Analyses were conducted using an ELISA (Enzyme Linked Immunosorbent Assay) for determining idursulfase concentration. The limit of detection (LOD)=1.25 ng/mL prior to multiplying by dilution factor. Samples were screened at a 1:50 dilution, therefore the assay sensitivity is 62.5 ng/mL. Samples falling beyond the high end of the calibration curve were further diluted and retested at an appropriate dilution that resulted in a value within the range of the curve. Selected samples were additionally analyzed using an enzyme activity assay. The LOD for this assay is 0.18 mU/mL at a minimal sample dilution of 1:150.

Animals in groups 1 and 2 that were dosed with saline or vehicle, respectively, all had serum idursulfase levels ranging between 138 ng/mL and <62.5 ng/mL (or <LOD) throughout the period of IV and IT dosing. Of 200 CSF samples tested from Group 1 and 2 animals, 62 demonstrated levels of I2S above the assay LOD. Of these, 7 values were high (>1,000 ng/mL). One other CSF sample collected pre IT dose 3 tested above 1,000 ng/mL of I2S.

The samples were then tested for idursulfase activity. In each case the activity results indicated the presence of I2S and when the approximate concentration of I2S was calculated based on the activity levels, the results were within 20% of those obtained by the antigen ELISA. (See Table 9) Additional randomly chosen CSF samples with antigen ELISA results <LOD were also tested using the enzyme activity assay to rule out any non-specific activity.

The samples giving these out-of-trend results were retested and confirmed. In addition, these samples were tested for idursulfase enzyme activity. These activity results also confirmed high idursulfase levels within 20% of those obtained by the idursulfase mass assay (Table 9).

The specificity of the activity assay was validated within this sample cohort by randomly testing CSF samples with idursulfase mass units below LOD and confirmed that idursulfase levels in these samples were indeed LOD (data not shown).

Example 4

Formulation

This Example summarizes the pharmaceutical development studies performed to establish the formulations of Idursulfase-IT Drug Substance and Drug Product for Phase I/II clinical trials.

TABLE 9

INVESTIGATION RESULTS FROM CSF SAMPLES

| Animal Number | Group | Dose | Dose Number | Dose Mode | Time Point | ELISA Result (mg/mL) | Activity Result (mU/mL) | Calculated ng/mL Based on Activity | Calculated as % of Measured |
|---|---|---|---|---|---|---|---|---|---|
| 003 | 1 | Saline | 5 | IT | Predose | 1392 | 4.7 | 1173 | 119% |
| 003 | 1 | Saline | 6 | IT | Predose | 7322 | 29.9 | 7469 | 96% |
| 004 | 1 | Saline | 2 | IT | 2 hr post | 17045 | 62.1 | 15527 | 110% |
| 006 | 1 | Saline | 6 | IT | 4 hr post | 16435 | 70.7 | 17682 | 93% |
| 006 | 1 | Saline | 1 | IT | Predose | 1320 | 5.3 | 1319 | 100% |
| 0016 | 2 | Vehicle | 1 | IT | 2 hr post | 3070 | 11 | 2743 | 112% |
| 017A | 2 | Vehicle | mo. 3 | IV | 4 hr post | 2236 | 8.8 | 2194 | 102% |
| 046 | 5 | 100 mg/kg | 3 | IT | Predose | 2086 | 7 | 1750 | 119% |

In this study, serum and CSF samples were analyzed for idursulfase concentration. Serum samples were collected according to the following schedule:

IV Doses: predose and 2 hours post doses 1 through 10, predose and 4 hours post doses 11 through 23, and at necropsy.

IT Doses: predose and 2 hours post doses 1 and 2, predose and 4 hours post doses 3 through 6, and at necropsy.

CSF samples were collected according to the following schedule:

IV Doses: predose and 2 hours post dose 1, and 4 hours post doses 3 and 6.

IT Doses: predose and 2 hours post doses 1 and 2, predose and 4 hours post doses 3 through 6, and at necropsy.

Generally, serum idursulfase cleared faster than CSF idursulfase.

Serum idursulfase levels in groups 1 and 2 animals that were dosed with saline or vehicle, respectively, were less than or equal to 138 ng/mL at all time points tested. Some animals had levels below the assay limit of detection (LOD).

Fewer CSF samples from groups 1 and 2 were above the assay LOD, with 7 notable exceptions that resulted in high (>1,000 ng/mL) levels. One CSF sample collected from an animal pre IT dose 3, also tested above 1,000 ng/mL idursulfase.

Due to the limitation of the excipients suitable for the CNS delivery, the effort for the formulation development for intrathecal delivery of idursulfase was focused on reducing the phosphate and polysorbate 20 level while still maintaining the stability equivalent to the I2S formulation for systemic delivery.

Three key screening stress studies were conducted to examine the effect of phosphate and polysorbate level. These included freeze thaw, shaking stress, and thermal stresses. The results demonstrated the saline formulation is more stable against the freeze thaw stress at low protein concentration (2 mg/mL). At high protein concentration (100 mg/mL), the freeze thaw stress did not cause instability issue for both saline and phosphate containing formulations. The shaking stress study confirmed that 0.005% polysorbate 20 protected the protein against shaking related stress. The thermal stability studies demonstrated that the saline formulation was more stable compared to the formulations containing phosphate. In addition, the pH of the saline formulation can be maintained at 6.0 for 24 months at 2-8° C. The amount of residual phosphate associated with the protein, as well as the increased protein concentration was found to contribute to the pH stability in the final formulation.

Methods
Effect of Freeze/Thaw Stress on Stability of Idursulfase in Saline and Phosphate Formulations To examine the effect of freeze/thaw on idursulfase stability in different formulations, the viral SEC pool was exchanged/concentrated using a Centricon Plus four times into either 150 mM NaCl or 137 mM NaCl with 20 mM sodium phosphate (both at pH 6.0). The protein concentrations were targeted to 2 mg/ml and 100 mg/mL. All solutions were filtered through a 0.22 micron PVDF filter. The solutions were aliquotted at 1 mL each into 2 mL borosilicate glass vials. The vials were placed on the middle shelf of a lyophilizer chamber and surrounded by placebo vials. The samples were frozen at a programmed freeze/thawing cycle (held for 1 hour at 20° C. and frozen to −50° C. at 1° C./min.) Then, thawed in two steps at a rate of 0.03° C./min from −50° C. to −25° C., held for 24 hours at −25° C., and allowed to thaw to 2-8° C.). After two or three freeze/thawing cycles, the samples were analyzed by appearance and SEC-HPLC assays.

Effect of Shaking/Shear Stress on Idursulfase in Phosphate and Saline Solutions

Shaking studies were performed on the idursulfase at different protein concentrations. The protein concentrations were tested at 2 mg/mL, 8 mg/mL, and 90-100 mg/mL in the present of 137 mM NaCl in 20 mM phosphate (pH 6.0) and 154 mM NaCl (pH 6.0) alone. To see if polysorbate was needed, various amounts of PS-20 were spiked into the test condition. The solutions were aliquoted at 1.2 mL each in 2 mL glass vials and then shaken on an orbital shaker at 250 rpm under ambient conditions for 24 hours. At baseline and 24 hours, the appearance was examined, and 0.1 mL aliquots were sampled in frozen at below ≤−65° C. in 0.5 mL polypropylene tubes until analysis by SEC-HPLC.

To first confirm the effect of polysorbate 20 level, a simulated shipping study was conducted using a 3 hour truck shipment of material followed by a 1 hour air test at Assurance Level 1 using random test options (conducted by Lansmont (Lansing, Mich.)). The samples were analyzed for appearance of particles and soluble aggregates by SEC-HPLC.

To examine the effect of stirring stress on the stability, a saline formulation (50 mg/mL, 154 mM NaCl, and 0.005% PS-20) was filled at 1.3 mL in a 3 mL type I glass vial and stoppered with a 13 mm stopper, which contained a Teflon coated magnetic stir bar (8 mm in length and 2 mm in diameter). The vials were placed on a stir plate set at speed setting 6 (the choice of setting 6 was maximal speed without causing excessive foaming). Appearance was determined at 0, 2, 24, 48, and 72 hours. The baseline and the 72 hour stirred samples were tested SEC-HPLC methods.

Thermal Stability Studies for Lead Formulations

Six lead formulations were compared for thermal stability. These formulations were chosen based on two parameters. The first parameter was that the protein concentration needed to be within therapeutic ranges for CNS delivery. The second parameter was to control the effect of phosphate concentration on the stability. The viral filtered SEC pool was buffered exchanged and concentrated using the Centricon Plus-80. Target concentrations of 50 and 100 mg/mL protein concentrations were achieved. The six formulations were spiked with a 1% polysorbate 20 solution for a final concentration of 0.01% PS-20. The material was filtered through a 0.22 micron PVDF filter and 0.5 mL added into 2 mL glass borosilicate vials. These vials were placed on stressed stability (40° C.), accelerated stability (25° C.), and real time storage (2-8° C.) in an inverted position. The stability samples at each time point was tested by SEC-HPLC, OD320, SAX-HPLC, SDS-PAGE (Commassie), pH, and activity.

Understanding the pH Control in Saline Formulation

To understand how the pH in the saline formulation was maintained, the following studies were conducted.

Testing the Residue of Phosphate in Saline Formulations

The viral filtered SEC pool (2 mg/mL idursulfase, 137 mM NaCl, 20 mM sodium phosphate, pH 6.0) was concentrated and diafiltered into 150 mM NaCl by using the Millipore TFF system and a Millipore Pellicon Biomax 30, 50 cm$^2$ filter. The samples were to determine the amount of phosphate associated with protein after 7×, 10× and 15× cycles of diafiltration into 0.9% saline (prepared at TK3). In addition, the permeate after 10× diafiltration (non-protein containing flow through from filtration) and the saline used in the filtration step were also tested.

Determining the Effect of Protein Concentration on pH

To better understand the control of the pH without the presence of a buffer (phosphate), protein effect studies were conducted. To determine the contribution of the protein on pH, material was diluted in 154 mM NaCl (saline) to 30 mg/mL, 10 mg/mL, 2 mg/mL, 1 mg/mL, 0.1 mg/mL, 0.01 mg/mL and saline alone. The material was aliquotted into 2 mL polypropylene tubes at a fill volume of 1 mL per tube. The samples were frozen at ≤−65° C. for 1 hour, thawed at ambient for 30 minutes, and the cycle repeated three times. The initial pH was measured and compared after 3× freeze/thaw cycles. The pH was also measured after 24 hours ambient exposure (by opening the caps of the tubes) of the samples to determine the effect protein concentration may have on pH shift.

Due to the limitation of the excipients suitable for the CNS delivery, the effort for the formulation development for intrathecal delivery of idursulfase was focused on reducing the phosphate and polysorbate 20 level while still maintaining the stability equivalent to I2S formulated for systemic administration. Three key screening stress studies were conducted, including freeze thaw, shaking stress, and thermal stresses.

Effect of Freeze/Thaw on Idursulfase in Saline and Phosphate Formulations

As shown in Table 10, at low protein concentration of 2 mg/mL, the 20 mM phosphate containing formulation generated more aggregates after the freeze thaw stress. The saline formulation remained at the same level of aggregates as the baseline. At high protein concentration (100 mg/mL), the freeze thaw stress appeared to have no effect on the stability in either of formulations (Table 11). The data indicated that the saline alone formulation has better stability against freeze thaw stress.

TABLE 10

SOLUBLE AGGREGATION AT LOW PROTEIN CONCENTRATION

|  | 2 mg/mL in 20 mM Phosphate, pH 6.0* % HMW species | 2 mg/mL in Saline, pH 6.0 % HMW species |
|---|---|---|
| Baseline | 0.02% | 0.05% |
| Post freeze thawing | 1.7% | 0.04% |

TABLE 11

SEC PROFILE TO DETERMINE SOLUBLE AGGREGATION
AT HIGH PROTEIN CONCENTRATION

|  | 100 mg/mL in 20 mM Phosphate, pH 6.0* | 100 mg/mL in Saline, pH 6.0 |
|---|---|---|
| Baseline | 0.05% | 0.06% |
| Post freeze thawing | 0.04% | 0.07% |

*The amount of NaCl was adjusted to 137 mM where the formulation contained 20 mM phosphate to maintain comparable tonicity.

Effect of Shaking Stress on Idursulfase in Solution

The shaking studies were conducted at three protein concentration levels of 2, 8, and 100 mg/mL. The data demonstrated that without polysorbate 20, precipitates occurred at all the protein concentration and also high level of soluble aggregates was observed at 2 mg/mL (Table 12 to Table 14). However, in the presence of very low level of P20 such as 0.005%, the precipitates and soluble aggregates were mostly prevented. The data indicated that a low level of polysorbate is required to protect the protein against shaking stress.

Tables 12-14: Shaking Study in a Lab Model (Rotation at 250 RPM for 24 Hours at Ambient)

TABLE 12

~2 mg/ml in 137 mM NaCl and 20 mM Phosphate at pH 6

| P20 Concentration | Appearance | SEC (% monomer) |
|---|---|---|
| 0% | Protein-like particles observed | 95.2% |
| 0.0005% | Protein-like particles observed | 99.4% |
| 0.001% | Protein-like particles observed | 99.4% |
| 0.0025% | Dust-like particles observed | 99.7% |
| 0.005% | Dust-like particles observed | 99.7% |
| 0.01% | Dust-like particles observed | 99.8% |

TABLE 13

~8 mg/ml in 137 mM NaCl and 20 mM Phosphate at pH 6

| Sample | Appearance | SEC (% monomer) |
|---|---|---|
| Without PS-20 (shaken) | Protein-like particles observed | 99.3% |
| 0.005% | No particles observed | 99.7% |

TABLE 14

90-100 mg/ml in Saline formulation

| P-20 Concentration | Appearance | SEC (% monomer) |
|---|---|---|
| Without PS-20 | Large protein-like particles observed | 100.% |
| 0.005% | Some particles observed | 99.8 |
| 0.01% | No particles | 99.9 |

*The control sample (without shaking) had 99.8% monomer.

To further confirm whether the 0.005% is sufficient for the stability against shaking, a simulated shipping study, which was close to the real shipping condition, was conducted on the saline formulation at 100 mg/mL protein with different level of polysorbate 20. The results confirmed that 0.005% was sufficient (Table 15).

TABLE 15

EFFECT OF POLYSORBATE 20 ON APPEARANCE
AND SOLUBLE AGGREGATES OF 100 MG/ML IN
SALINE AFTER A SIMULATED SHIPPING STUDY

| Polysorbate 20 | Appearance | SEC (% monomer) |
|---|---|---|
| 0 (control) No shipping stress | No particles | 99.8% |
| 0 | <10 small particles observed | 99.9% |
| 0.005% | No particles | 99.8% |
| 0.01% | No particles | 99.8% |

The effect of stirring using a magnetic stir bar on the stability of the saline formulation containing 50 mg/mL idursulfase with 0.005% polysorbate 20 is summarized in Table-Table 16. As shown, the protein is not susceptible to the stress caused by stirring using a magnetic stir bar for 72 hrs. The results confirmed that 0.005% was sufficient against stirring stress as well.

TABLE 16

EFFECT OF POLYSORBATE 20 ON 53 MG/ML IDURSULFASE
STABILITY UPON AGGRESSIVE STIRRING

| Appearance | | | | | SEC-HPLC, monomer % | |
|---|---|---|---|---|---|---|
| Baseline | 2 hr | 24 hr | 48 hr | 72 hr | Baseline | 72 hr |
| no ppt | no ppt | no ppt | no ppt | no ppt | 99.96% | 99.94% |

Thermal Stability for the Lead Candidates

Six key formulations were examined over 24 months for stability testing. The results of these tests are discussed in this section.

Appearance

The appearance of all of the formulations remained slightly opalescent and essentially particle free under all of the temperatures and timepoints tested for the six formulations.

OD320

To examine the potential increases in turbidity, the OD320 values were determined and summarized in Table 17 Table. As shown, in the frozen storage, the OD320 values for all the formulations remained the same as the baseline after 24 months storage. At 2-8 C condition, the saline formulations remained the same as the baseline after 24 months but the phosphate containing formulations had an increased level in OD320 values. At the accelerated condition of 25 C, the saline formulations also had a slight increase in OD320 after 3-6 months but the phosphate containing formulations showed a more significant increase. These results suggest that the saline formulation is more stable against thermal stress.

TABLE 17

COMPARING OD320 FOR SALINE AND PHOSPHATE FORMULATIONS*

|  | 50 mg/ml, 154 mM NaCl, pH 6.0 | 100 mg/ml, 154 mM NaCl, pH 6.0 | 50 mg/ml, 150 mM NaCl, 5 mM NaPO$_4$, pH 6.5 | 100 mg/ml, 150 mM NaCl, 5 mM NaPO$_4$, pH 6.5 | 100 mg/ml, 137 NaCl, 20 mM NaPO$_4$, pH 6.0 | 100 mg/ml, 137 NaCl, 20 mM NaPO$_4$, pH 6.5 |
|---|---|---|---|---|---|---|
| ≤−65° C. | | | | | | |
| Baseline | 0.026 | 0.043 | 0.025 | 0.042 | 0.042 | 0.044 |
| 16 months | 0.027 | 0.043 | 0.029 | 0.045 | 0.045 | 0.046 |
| 24 months | 0.023 | 0.046 | 0.024 | 0.068 | 0.045 | 0.046 |
| 25° C. | | | | | | |
| 3 months | 0.043 | 0.076 | 0.065 | 0.116 | 0.124 | 0.137 |
| 6 months | 0.040 | 0.077 | 0.064 | 0.110 | 0.122 | 0.138 |
| 2-8° C. | | | | | | |
| 3 months | 0.028 | 0.047 | 0.034 | 0.053 | 0.071 | 0.072 |
| 6 months | 0.028 | 0.049 | 0.040 | 0.067 | 0.086 | 0.090 |
| 16 months | 0.027 | 0.051 | 0.049 | 0.089 | 0.102 | 0.111 |
| 24 months | 0.033 | n/a | 0.056 | 0.099 | 0.110 | 0.113 |

*All contain 0.01% Polysorbate 20

SEC-HPLC

The data summary of all the formulations tested by SEC-HPLC is listed in Table. At the frozen storage conditions, there was no change after 24 months compared to the baseline.

At the stressed condition of 40° C., after two weeks all the formulations had increased levels of soluble aggregates. In addition, the phosphate containing formulations also showed a "12 min" peak. However, after 1 month, the "12 min peak" peaks observed in the phosphate containing formulation seemed to disappear. In addition, the soluble aggregate level did not further increase for all the formulations compared to the 2 week time point (FIG. 8 and Table 18).

At the accelerated condition of 25° C., compared to the baseline, for all the formulations, the increased level of soluble aggregates was minimal after 6 months. However, all the phosphate containing formulations showed the "12 min" peak (FIG. 9 and Table 18 Table).

At the long term storage condition of 2-8° C., after 24 months the increase of the soluble aggregates for all the formulation was also minimal after 24 months storage. Consistent with all conditions, the phosphate containing formulations also had the "12 min peak", which increased slightly over time (FIG. 10 and Table 18 Table)

These results indicate that the saline formulations had the least changes compared to the phosphate containing formulations at all the storage condition.

TABLE 18

COMPARING AGGREGATION BY SEC-HPLC IN SALINE & PHOSPHATE FORMULATIONS*

|  | 50 mg/ml, 154 mM NaCl, pH 6.0 | 100 mg/ml, 154 mM NaCl, pH 6.0 | 50 mg/ml, 150 mM NaCl, 5 mM NaPO$_4$, pH 6.5 | 100 mg/ml, 150 mM NaCl, 5 mM NaPO$_4$, pH 6.5 | 100 mg/ml, 137 NaCl, 20 mM NaPO$_4$, pH 6.0 | 100 mg/ml, 137 NaCl, 20 mM NaPO$_4$, pH 6.5 |
|---|---|---|---|---|---|---|
| ≤−65° C. | | | | | | |
| Baseline | 99.9 | 99.9 | 99.9 | 99.8 | 99.9 | 99.9 |
| 6 months | 99.9 | 99.9 | 99.8 | 99.8 (0.03)[a] | 99.8 | 99.8 |
| 16 months | 99.9 | 99.8 | 99.9 | 99.8 | 99.8 | 99.9 |
| 24 months | 99.8 | 99.8 | 99.8 | 99.9 (0.21)[a] | 99.8 | 99.8 |
| 40° C. | | | | | | |
| 2 weeks | 97.9 | 97.8 | 97.9 (0.23)[a] | 97.8 (0.20)[a] | 97.4 (0.34)[a] | 97.5 (0.16)[a] |
| 1 month | 97.2 | 97.3 | 97.6 | 97.5 | 97.7 | 97.3 |
| 25° C. | | | | | | |
| 3 months | 99.4 | 99.3 | 99.5 (0.22)[a] | 99.4 (0.25)[a] | 99.4 (0.30)[a] | 99.6 (0.04)[a] |
| 6 months | 99.1 | 98.9 | 99.4 (0.25)[a] | 99.2 (0.27) | 99.2 (0.24)[a] | 99.6 (0.02)[a] |
| 2-8° C. | | | | | | |
| 3 months | 99.8 | 99.7 | 99.9 | 99.7 (0.11)[a] | 99.7 (0.11)[a] | 99.7 (0.02)[a] |

TABLE 18-continued

COMPARING AGGREGATION BY SEC-HPLC IN SALINE & PHOSPHATE FORMULATIONS*

|  | 50 mg/ml, 154 mM NaCl, pH 6.0 | 100 mg/ml, 154 mM NaCl, pH 6.0 | 50 mg/ml, 150 mM NaCl, 5 mM NaPO$_4$, pH 6.5 | 100 mg/ml, 150 mM NaCl, 5 mM NaPO$_4$, pH 6.5 | 100 mg/ml, 137 NaCl, 20 mM NaPO$_4$, pH 6.0 | 100 mg/ml, 137 NaCl, 20 mM NaPO$_4$, pH 6.5 |
|---|---|---|---|---|---|---|
| 6 months | 99.9 | 99.8 | 99.7 (0.06)$^a$ | 99.7 (0.06)$^a$ | 99.8 (0.09) | 99.8 |
| 16 months | 99.8 | 99.7 | 99.5 (0.46)$^a$ | 99.4 (0.50)$^a$ | 99.5 (0.42)$^a$ | 99.8 (0.04)$^a$ |
| 24 months | 99.7 | n/a | 99.4 (0.50)$^a$ | 99.4 (0.50)$^a$ | 99.3 (0.54)$^a$ | 99.6 (0.25)$^a$ |

*All formulations contain 0.01% polysorbate 20

$^a$The values represented are high molecular species which elute ~12 minutes in the current SEC HPLC method often referred to as the "12 minute peak." This peak is thought to be strongly associated with the presence of phosphate in the formulation.

SAX-HPLC

The data summary for SAX-HPLC is listed in Table 19. At the stressed/accelerated conditions, the saline formulations appeared had slightly more changes (FIGS. 11 and 12) but at the long term storage conditions, there was no changes for all the formulations after 24 months (Table 19 and FIG. 13). This indicates the saline formulations are stable for 24 months at 2-8 C.

TABLE 19

COMPARING CHANGES IN CHARGE BY SAX-HPLC METHOD FOR SALINE AND PHOSPHATE FORMULATIONS (ALL WITH 0.01% POLYSORBATE-20) OVER 24 MONTHS

|  | 50 mg/ml, 154 mM NaCl, pH 6.0 | 100 mg/ml, 154 mM NaCl, pH 6.0 | 50 mg/ml, 150 mM NaCl, 5 mM NaPO$_4$, pH 6.5 | 100 mg/ml, 150 mM NaCl, 5 mM NaPO$_4$, pH 6.5 | 100 mg/ml, 137 NaCl, 20 mM NaPO$_4$, pH 6.0 | 100 mg/ml, 137 NaCl, 20 mM NaPO$_4$, pH 6.5 |
|---|---|---|---|---|---|---|
| Baseline | A + B = 51; E + F = 18 | A + B = 51; E + F = 18 | A + B = 52; E + F = 18 | A + B = 50; E + F = 18 | A + B = 51; E + F = 17 | A + B = 52; E + F = 18 |
| 40° C. |  |  |  |  |  |  |
| 2 weeks | A + B = 51; E + F = 16 | A + B = 52; E + F = 16 | A + B = 51; E + F = 17 | A + B = 51; E + F = 17 | A + B = 51; E + F = 17 | A + B = 49; E + F = 17 |
| 1 month | A + B = 50; E + F = 17 | A + B = 50; E + F = 17 | A + B = 50; E + F = 17 | A + B = 50; E + F = 17 | A + B = 50; E + F = 17 | A + B = 50; E + F = 17 |
| 25° C. |  |  |  |  |  |  |
| 3 months | A + B = 48; E + F = 18 | A + B = 48; E + F = 18 | A + B = 48; E + F = 18 | A + B = 47; E + F = 18 | A + B = 47; E + F = 18 | A + B = 47; E + F = 18 |
| 6 months | A + B = 45; E + F = 18 | A + B = 45; E + F = 18 | A + B = 44; E + F = 18 | A + B = 45; E + F = 18 | A + B = 45; E + F = 18 | A + B = 44; E + F = 18 |
| 2-8° C. |  |  |  |  |  |  |
| 3 months | A + B = 47; E + F = 18 | A + B = 47; E + F = 18 | A + B = 47; E + F = 18 | A + B = 47; E + F = 18 | A + B = 46; E + F = 18 | A + B = 47; E + F = 18 |
| 6 months | A + B = 44; E + F = 18 | A + B = 44; E + F = 19 | A + B = 44; E + F = 18 | A + B = 44; E + F = 18 | A + B = 45; E + F = 19 | A + B = 44; E + F = 19 |
| 16 months | A + B = 51; E + F = 18 | A + B = 50; E + F = 18 | A + B = 51; E + F = 19 | A + B = 51; E + F = 18 | A + B = 49; E + F = 19 | A + B = 50; E + F = 18 |
| 24 months | A + B = 52; E + F = 18 | A + B = 52; E + F = 18 | A + B = 52; E + F = 18 | A + B = 52; E + F = 18 | A + B = 52; E + F = 17 | A + B = 51; E + F = 18 | pH

Table 20 demonstrates that the pH of all the formulations remained comparable to the baseline for 24 months at 2-8° C. For the saline formulations, although there was no buffer, the pH maintained constant at 6.0 for 24 months.

TABLE 20

COMPARING PH FOR SALINE AND PHOSPHATE FORMULATIONS (ALL WITH 0.01% POLYSORBATE-20) OVER 24 MONTHS AT 2-8° C.

|  | 50 mg/ml, 154 mM NaCl, pH 6.0 | 100 mg/ml, 154 mM NaCl, pH 6.0 | 50 mg/ml, 150 mM NaCl, 5 mM NaPO$_4$, pH 6.5 | 100 mg/ml, 150 mM NaCl, 5 mM NaPO$_4$, pH 6.5 | 100 mg/ml, 137 NaCl, 20 mM NaPO$_4$, pH 6.0 | 100 mg/ml, 137 NaCl, 20 mM NaPO$_4$, pH 6.5 |
|---|---|---|---|---|---|---|
| Baseline | 6.03 | 6.00 | 6.43 | 6.41 | 5.96 | 6.47 |
| 24 months | 6.06 | n/a | 6.42 | 6.44 | 6.01 | 6.53 |

Enzyme Activity

Compared to the reference standard, the specific activity for all the formulations after 24 months at 2-8° C. was equivalent within the assay variation, which suggest idursulfase remained stable in the saline formulation for 24 months (Table 21).

TABLE 21

ACTIVITY RESULTS BY ION EXCHANGE CHROMATOGRAPHY AFTER 24 MONTHS REAL TIME STABILITY (2-8° C.) IN SALINE AND PHOSPHATE FORMULATIONS

|  | 50 mg/ml, 154 mM NaCl, pH 6.0 | 100 mg/ml, 154 mM NaCl, pH 6.0 | 50 mg/ml, 150 mM NaCl, 5 mM NaPO$_4$, pH 6.5 | 100 mg/ml, 150 mM NaCl, 5 mM NaPO$_4$, pH 6.5 | 100 mg/ml, 137 NaCl, 20 mM NaPO$_4$, pH 6.0 | 100 mg/ml, 137 NaCl, 20 mM NaPO$_4$, pH 6.5 |
|---|---|---|---|---|---|---|
| Specific Activity (U/mg) | 43 | n/a | 42 | 51 | 49 | 45 |

*The Specific activity of the reference standard was 56 U/mg during testing 24 months samples.

Detection of Residual Phosphate Associated with the Protein

The final UF/DF step in preparing the saline formulation was used to diafilter the protein solution from 137 mM NaCl, 20 mM sodium phosphate into 150 mM NaCl. To examine how the diafiltration cycle number affects the residual phosphate concentration in the final product, a lab scale study was conducted using the Drug Substance (2 mg/mL idursulfase, 137 mM NaCl, 20 mM sodium phosphate, pH 6.0). The drug substance was first concentrated to 50 mg/mL idursulfase and then dialfiltered into 150 mM saline. Samples were taken at 7x, 10x, and 15x diafiltration step and tested by ICP for phosphate content. The test results are summarized in Table 22. As shown, the saline diafiltration solution does not contain any phosphate. After 7xDF, the protein contained about 0.22 mM phosphate, which was higher than theoretical calculated value. After 10xDF, the protein retentate contained about 0.16 mM phosphate while the flow through was only about 0.07 mM phosphate, which indicated that the phosphate was binding to the protein. After 15xDF, the phosphate level was dropped to about 0.07 mM.

The results from the study indicated that about 0.2 mM phosphate residue remained in the Drug Substance, which likely contributed to maintaining the pH of 6.0 for the saline formulation.

TABLE 22

SODIUM PHOSPHATE REMAINING WITH THE PROTEIN AFTER MULTIPLE DIAFILTRATION STEPS

| Sample ID | μg/ml (ppm) | mM |
|---|---|---|
| Starting material DP04-002-X | N/A | 20 |
| 150 mM NaCl solution (DF buffer) | *below LOQ | 0 |
| Protein Retentate after 7x DF | 21 | 0.22 |
| Protein Retentate after 10x DF | 15 | 0.16 |
| Permeate (flow through) after 10X DF | 7 | 0.07 |
| Protein Retentate after 15x DF | 7 | 0.07 |
| DP06-004-X | 21 | 0.22 |

*The starting saline buffer was tested and no detectable phosphate was detected.

Protein Concentration Effect on Maintaining Formulation pH

From the phosphate content analysis, apparently phosphate binds to the protein. Therefore, it is expected high protein may bind more phosphate, which could maintain the pH better. To examine that hypothesis, the protein in the saline solution was concentrated to different levels and pH of the solutions after different processing conditions was tested. The results are summarized in Table 23.

As shown, the initial pH of the solutions was maintained to about 6.0 independent of the protein concentration. However, after ambient exposure for 24 hr or three freeze thaw cycles, the pH of the solutions containing 0.1 mg/mL protein or less did not maintain a constant pH around 6.0. The pH of the solutions at the protein concentration of above 1 mg/mL was maintained around 6.0. This confirmed that the protein concentration is a controlling factor in maintaining the pH of the saline solutions.

TABLE 23

EFFECT OF PROTEIN CONCENTRATION ON PH OF UNBUFFERED SALINE FORMULATIONS

| Protein Concentration (mg/mL) | Initial pH | pH after 24 hr Ambient Exposure | pH After Three Freeze Thaw Cycles* |
|---|---|---|---|
| 60 | 6.1 | 6.1 | 6.1 |
| 30 | 6.1 | 6.1 | 6.1 |
| 10 | 6.1 | 6.0 | 6.1 |
| 2 | 6.0 | 5.9 | 5.9 |
| 1 | 6.0 | 5.8 | 6.0 |
| 0.1 | 5.9 | 5.6 | 5.8 |
| 0.01 | 6.0 | 5.6 | 5.8 |
| 0 (saline) | 6.1 | 5.7 | 5.6 |

*Samples were stored at ≤−65° C. for at least 1 hour and thawed at ambient temperature for 0.5 hour, and this cycle was repeated three times.

The results from this study demonstrated that idursulfase in the saline formulation (50 mg/mL idursulfase, 0.005% polysorbate, 150 mM NaCl, pH 6.0) is stable for at least 24 months when stored at 2-8 C. This formulation appeared to be more stable compared to the phosphate containing formulation. The selection of 0.005% polysorbate 20 was sufficient to protect the protein against the shaking stress. In addition, the study also indicated that the pH of the saline formulation can be stably maintained at 6.0 for 24 months at 2-8° C., in part due to the residual phosphate and high protein concentration in the final formulation.

Example 5

Biodistribution

Having successfully demonstrated that intrathecal administration is an efficacious way of delivering I2S to the tissues of the CNS, additional studies were conducted to determine whether IT-administered I2S is capable of distributing into the deep tissues of the brain and whether there is cellular localization of IT-administered I2S. A recombinant human iduronate-2-sulfatase (I2S) formulation was prepared and formulated in a vehicle of 154 mM NaCl, 0.005% polysorbate 20 at a pH of 6.0.

Non-human primates were administered either 3 mg, 30 mg, or 100 mg of I2S on a monthly basis by way of an implanted intrathecal port for six consecutive months. The design of the study is summarized in Table 24 below.

TABLE 24

| Group | n | IV Dose (mg/kg)[a] | IT Dose (mg)[a] | Last Day on Study (number of animals) 6 Months | Recovery |
|---|---|---|---|---|---|
| 1 | 6 | DC (NS) | DC (PBS) | 6 | — |
| 2 | 12 | 0 (vehicle) | 0 (IT vehicle) | 6 | 6 |
| 3 | 12 | 0.5 | 3 | 6 | 6 |
| 4 | 6 | 0.5 | 30 | 6 | — |
| 5 | 12 | 0.5 | 100 | 6 | 6 |

[a]Idursulfase unless otherwise specified.
DC (device control);
IT (intrathecal);
IV (intravenous);
NS (normal saline);
PBS (phosphate-buffered saline, pH 7.2).

Repeat monthly administration of I2S to the non-human primates for six months was well tolerated at the highest dose tested and not associated with any significant adverse toxicologic events. Twenty-four hours following the administration of the sixth and final dose of I2S, the subject non-human primates were sacrificed and CNS tissues of such non-human primates were examined.

As determined by immunohistochemistry (IHC), there was widespread cellular deposition of I2S throughout the cells and tissues of the CNS. I2S protein was detected in all tissues of the brain by IHC, with a deposition gradient from the cerebral cortex to the ventricular white matter. In the gray matter I2S was detected in the neurons of the cerebrum, cerebellum, brain stem, and spinal cord of all groups in a dose-dependent manner. In the surface gray matter of the higher dose groups, large numbers of cerebral neurons were positive for I2S staining in the surface cortex (FIG. 40A). I2S was also detected in neurons in the thalamus (FIG. 40B), hippocampus (FIG. 40C), caudate nucleus FIG. 40D) and spinal cord (FIG. 40E). Meningial and perivascular cells were also positive for I2S staining (FIG. 40F).

As depicted in FIGS. 41 and 42, distribution of IT-administered I2S into the tissues of the CNS and in particular deposition in the gray matter, thalamus and cerebral cortex of the subject non-human primates is evident. Furthermore, FIGS. 42 and 43 illustrate that the IT-administered I2S accumulates in the depicted CNS tissues of the subject non-human primates in a dose dependant manner. Co-localization staining also revealed that IT administration of I2S associates with both neurons and oligodendrocytes. The IT-administered I2S also distributes and localizes throughout the cerebrum of the subject non-human primates as evidenced by FIG. 44. In particular, FIG. 45 illustrates neuronal uptake and axonal association of the I2S following IT-administration to the non-human primates, as demonstrated by filament staining Also of particular interest, the present studies illustrate that I2S is selective for neuronal cells and such neuronal cells facilitate the distribution of intrathecally-administered I2S into the deep tissues of the brain and appears to be associated with axonal structures, indicating anterograde axonal transport of I2S.

Table 25 below present the pharmacokinetic data of various administration routes and doses for a separate animal study.

TABLE 25

| Dose unit | AUClast hr * ng/mL | Body weight kg | Brain weight kg | Dose mg/kg BW | Dose mg/kg Br wt |
|---|---|---|---|---|---|
| 0.5 mg/kg | 8331 | 2.7 | 0.1 | 0.5 | 5 |
| 1 mg, IT | 1933 | 3.1 | 0.1 | 0.32 | 10 |
| 10 mg, IT | 31316 | 2.7 | 0.1 | 3.66 | 100 |
| 30 mg, IT | 140345 | 2.9 | 0.1 | 10.34 | 300 |

$^{124}$I-labeled I2S was administered to test animals as shown in Table 26 below and PET scan results are shown in FIG. 62, FIG. 63.

TABLE 26

| Group | Animals/Group | Route | Test Article | Dose |
|---|---|---|---|---|
| 1 | 1 | ICV | [124I]-idursulfase | 3 mg |
| 2 | 4 | IT-L | [124I]-idursulfase | 3 mg |
| 3 | 4 | IV | [124I]-idursulfase | 0.1 mg/kg |
| 4 | 4 | IV | [124I]-idursulfase | 1 mg/kg |

The present studies also demonstrated the cellular identification of IT-administered I2S in white matter brain tissue near the ventricles of the subject non-human primates following IT-administration. While the I2S staining density in the white matter was generally lower than the gray matter, I2S was detected within oligodendrocytes (FIG. 46). In particular, FIG. 46 illustrates the cellular identification of I2S in white matter brain tissues and further demonstrates that I2S does not appear to associate with myelin.

In addition to demonstrating the distribution of IT-administered I2S deep into the tissues of the brain, the present studies also confirmed localization of I2S into the target organelles, and importantly localization of I2S into the lysosomes which are affected organelles in the lysosomal storage disorders, such as Hunter's syndrome. In particular, I2S was located within the lysosomes and also detected within axons. FIG. 46 illustrates the localization of IT-administered I2S within the lysosomes of oligodendrocytes of the subject non-human primate, thereby confirming that IT-administered I2S is capable of distributing into the deep tissues of the brain and is capable of cellular localization.

In order to discern whether the delivered I2S retained biological activity, levels of I2S in the brain were measured utilizing a specific activity assay. The activity in the brain of the 3 mg IT group 24 hours after the last dose was not apparently different from the basal levels in the device control and vehicle control animals. Enzyme activity in the brain of 30 mg and 100 mg IT dosed animals was above baseline at necropsy (24 hours post-dose).

Further animal tests to discern the biodistribution of I2S following IT delivery to the brain is shown in FIG. 60 and the sample numbers correspond to Table 27 below.

TABLE 27

| LOCATION OF SAMPLES | |
|---|---|
| Sample Number | Structure |
| 1 | Cerebral cortex-superficial (L) |
| 2 | Cerebral cortex-superficial (R) |
| 3 | Caudate nucleus (R) |
| 4 | Caudate nucleus (L) |
| 5 | Corpus callosum |
| 6 | Cerebral cortex (frontal)-superficial (L) |
| 7 | Cerebral cortex (frontal)-superficial (R) |
| 8 | White matter-superficial (L) |
| 9 | White matter-superficial (R) |
| 10 | White matter-deep (L) |
| 11 | White matter-deep (R) |
| 12 | Cerebal cortex (temporal)-superficial (L) |
| 13 | Cerebal cortex (temporal)-superficial (R) |
| 14 | Thalamus (L) |

TABLE 27-continued

| LOCATION OF SAMPLES | |
|---|---|
| Sample Number | Structure |
| 15 | Thalamus (R) |
| 16 | Hypothalamus (L) |
| 17 | Hypothalamus (R) |
| 18 | Hippocampus (L) |
| 19 | Hippocampus (R) |
| 20 | White matter-deep (L) |
| 21 | White matter-superficial (R) |
| 22 | Corpus callosum |
| 23 | White matter-deep (L) |
| 24 | White matter-deep (R) |
| 25 | Cerebellum (R) |

Example 6

IT vs. ICV Delivery

The I2S distribution patterns observed in the foregoing example was also recapitulated in healthy Beagle dogs given a single IT or ICV dose. Male Beagle dogs were randomized using computer-generated numbers into two groups (Group 1 (ICV), N=3; Group 2 (IT); N=4). All had catheters implanted in the subarachnoid space at the lumbar spine or in the left lateral cerebral ventricle (for dosing) and in the cisterna magna (for sampling). All catheters terminated in a subcutaneous titanium access port. An additional dog was used as an un-dosed surgical control.

A single bolus 1 ml injection of I2S (30 mg/ml in 20 mM sodium phosphate, pH 6.0; 137 mM sodium chloride; 0.02% polysorbate-20), was administered IT or ICV, followed by a 0.3 ml flush with phosphate buffered saline (PBS; pH 7.2). Clinical signs were monitored and sacrifice occurred 24 hours following the dose. Brain and spinal cord tissue samples were collected for quantitative I2S analyses as determined by ELISA, I2S enzyme activity and IHC, and compared between the study groups.

I2S was widely distributed throughout the gray matter of both IT and ICV groups as determined by IHC. In the cerebral cortex, neurons were positive for I2S in all six neuronal layers, from the surface molecular layer to the deep internal layer in both IT and ICV groups, as illustrated by FIG. 47 (A and B). In the cerebellar cortex of the IT and ICV groups, I2S was detected in neurons, including Purkinje cells, as illustrated by FIG. 47 (C and D). In both IT and ICV groups a large population of neurons in the hippocampus was positive for I2S, as demonstrated by FIG. 47 (E and F). I2S positive neurons were also found in the thalamus and caudate nucleus in both of the groups, as illustrated in FIG. 47 (G and H).

The present studies therefore confirm the ability of IT-administered enzymes to distribute into the deep cells and tissues of the brain and support the utility of IT-administered enzymes such as I2S for the treatment of the CNS manifestations associated with lysosomal storage diseases, such as Hunter's syndrome.

Example 7

Iduronate-2-Sulfatase Deficient Mouse Model

Having demonstrated that IT-administered I2S is capable of distributing into the deep tissues of the brain and cellular localization of I2S, further studies were conducted to determine the therapeutic efficacy of IT-administered I2S. A genetically-engineered iduronate-2-sulfatase knock-out (IKO) mouse model of Hunter syndrome was developed to study the ability of the IT-administered I2S to alter disease progression. The I2S knock-out mouse model was developed using a targeted disruption of the I2S locus which results in an accumulation of glycosaminoglycans (GAG) in tissues and organs. The IKO mouse model exhibits many of the physical characteristics of Hunter syndrome seen in humans, including the characteristic coarse features and skeletal defects. In addition, the IKO mouse model demonstrates elevated glycosaminoglycan (GAG) levels in urine and in tissues throughout the body, as well as widespread cellular vacuolization which was observed histopathologically.

In the present study, commercially-available I2S (Elaprase®) was concentrated and re-suspended in phosphate buffered saline (PBS). Six groups of male IKO mice, 8-12 weeks old, were treated with I2S (10 µl; 26 mg/ml). Groups A and B (N=3) were intrathecally administered three 260 µg doses (at days 1, 8, and 15) and two 260 µg doses (at days 1 and 8) of I2S, respectively. Group D was also treated with three intrathecally administered 260 µg doses at days 1, 8, and 15. Group C and E (N=3) were untreated control groups and group F (N=3) was an untreated wild-type control. Control mice were administered a vehicle without I2S. Mice were sacrificed after 1 hour following the last injection, followed by tissue preparation for immunohistochemistry (IHC) and histopathological analysis.

Following the third injection, there was widespread reduction of cellular vacuolation in the surface cerebral cortex, caudate nucleus, thalamus and the cerebellum in I2S-treated mice compared to vehicle-treated mice. Reductions in cellular vacuolation were also found in the white matter after IT treatment. Distribution of I2S to the brain tissues of the IKO mouse was evident following IT-administration.

Three weekly IT administrations of I2S in the IKO mice also demonstrated a marked reduction in CNS cellular vacuolization at both light and electronic microscopic levels. Following IT administration of I2S, a reduction of cellular vacuolation was evident relative to untreated IKO mice, suggesting that IT-administered I2S is capable of altering disease progression. As illustrated in FIG. 48, a reduction of cellular vacuolation was evident in the corpus callosum and formix of the IKO mice following IT-administration of I2S. FIG. 49 illustrates a marked reduction in the presence of lysosomal associated membrane protein 1 (LAMP1), a lysosomal disease pathological biomarker, in the surface cerebral cortex tissues of the treated IKO mouse.

Additionally, electron microscopy demonstrated a reduction in the presence of storage inclusions in neurons in the gray matter and vacuolation in oligodendrocytes in the white matter. In particular, the IKO mice IT-administered I2S also demonstrated a reduction in palisaded lamellar bodies ("zebra bodies") which are characteristic of certain lysosomal storage diseases. In particular, FIG. 5 represents an electron microscope scan illustrating a reduction of the characteristic zebra bodies in the neurons of the IKO mouse that was administered I2S, relative to the untreated IKO mouse. Similarly, FIG. 5 illustrates an electron microscope scan of oligodendrocytes in the corpus callosum.

In addition, the IT administrations of I2S to the IKO mice also demonstrated a marked reduction in the lysosomal disease pathological biomarker lysosomal associated membrane protein 1 (LAMP1) immunostaining, an indicator of lysosomal activity and disease state, in the surface cerebral cortex, caudate nucleus, thalamus, cerebellum and white matter. As illustrated in FIG. 49A, a marked reduction in LAMP1 immunostaining is evident in the treated IKO mouse surface cerebral cortex tissue relative to the untreated IKO control mouse surface cerebral cortex tissue illustrated in FIG. 49B, reflecting an improvement in disease pathology.

FIG. 20 quantitatively illustrates and compares the concentration of LAMP1 measured in $\mu m^2$ areas of brain tissue. Morphometrical analysis of LAMP-1 immunostaining of various brain regions confirmed that there were significant reductions in the LAMP-1 positive staining in all areas of the brain evaluated. As shown in FIG. 4, in each area of brain tissue evaluated (the cortex, caudate nucleus and putamen (CP), thalamus (TH), cerebellum (CBL) and white matter (WM)) the LAMP-positive area was reduced in the treated IKO mice relative to the untreated IKO control mice, and approached the LAMP-positive area of the wild-type mice. Particularly notable is that the LAMP-positive areas in each area of brain tissue analyzed were further reduced with continued treatment duration.

Reduction of abnormally high lysosomal activity correlated with dramatic morphological improvements in all areas of the brain. These results confirm that IT-administered I2S is capable of altering progression of lysosomal storage diseases, in a genetically-engineered IKO mouse model, further confirming the ability of IT-administered enzymes such as I2S to treat the CNS manifestations associated with lysosomal storage diseases, such as Hunter's syndrome.

Example 8

Treatment of Hunter's Disease Patients

Direct CNS administration through, e.g., IT delivery can be used to effectively treat Hunter's Disease patients. This example illustrates a multicenter dose escalation study designed to evaluate the safety of up to 3 dose levels every other week (EOW) for a total of 40 weeks of I2S administered via an intrathecal drug delivery device (IDDD) to patients with late infantile Hunter's Disease. Various exemplary intrathecal drug delivery devices suitable for human treatment are depicted in FIGS. 45-48.

Up to 20 patients will be enrolled:
Cohort 1: 5 patients (Lowest Dose)
Cohort 2: 5 patients (Intermediate Dose)
Cohort 3: 5 patients (Highest Dose)
5 patients will be randomized to no treatment.

Patients are selected for the study based on inclusion of the following criteria: (1) appearance of first symptoms prior to 30 months of age; (2) ambulatory at the time of screening (defined as the ability to stand up alone and walk forward 10 steps with one hand held); (3) presence of neurological signs at time of screening. Typically, patients having a history of hematopoietic stem cell transplantation are excluded.

Safety of ascending doses of I2S administered by IT injection for 40 weeks in children with late infantile Hunter's Disease is determined. In addition, the clinical activity of I2S on gross motor function, and single and repeated-dose pharmacokinetics in serum and concentrations in cerebrospinal fluid (CSF) are assessed.

A therapeutically effective amount of I2S is administered intrathecally at regular intervals, depending on the nature and extent of the disease's effects, and on an ongoing basis. Administration at an "interval," as used herein, indicates that the therapeutically effective amount is administered periodically (as distinguished from a one-time dose). The interval can be determined by standard clinical techniques. In some embodiments, I2S is administered intrathecally approximately every other week. The administration interval for a single individual need not be a fixed interval, but can be varied over time, depending on the needs of the individual. For example, in times of physical illness or stress, if anti-I2S antibodies become present or increase, or if disease symptoms worsen, the interval between doses can be decreased.

Example 9

Treatment of Hunter's Disease Patients

Direct CNS administration through, e.g., IT delivery can be used to effectively treat Hunter's Disease patients. This example illustrates a multicenter dose escalation study designed to evaluate the safety of up to 3 dose levels every-month for a total of 6 months of I2S administered via an intrathecal drug delivery device (IDDD) to patients with late infantile Hunter's Disease. Various exemplary intrathecal drug delivery devices suitable for human treatment are depicted in FIGS. 45-48 and a schematic of the trial is shown in FIG. 62.

Up to 16 patients will be enrolled:
Cohort 1: 4 patients (Lowest Dose-10 mg)
Cohort 2: 4 patients (Intermediate Dose-30 mg)
Cohort 3: 4 patients (Highest Dose-100 mg)
4 patients will be randomized to no treatment or use of device.

Hunter's Disease patients frequently develop cognitive and neurodevelopmental impairment including delay of early development milestones (e.g., walking, speech, toilet training), intellectual deficit, hyperactivity, aggression, hearing impairment, epilepsy and hydrocephalus. All of the indications can be part of the criteria for trials. Patients are selected for the study based on inclusion of the following criteria: (1) 3-18 years of age; (2) intelligence quotient of less than 77 or a decline of 15 to 30 IQ points in past 3 years; (3) no CSF shut or poorly controlled seizure disorder and (4) no co-morbidities presenting anesthesia and/or surgical risks.

Safety of ascending doses of I2S administered by IT injection for 6 months in children with late infantile Hunter's Disease is determined. In addition, the clinical activity of I2S on gross motor function, and single and repeated-dose pharmacokinetics in serum and concentrations in cerebrospinal fluid (CSF) are assessed.

Objectives of the study will be to evaluate the safety and tolerability of ascending doses of I2S, as well as the safety, tolerability and long term patency of the IDDD. Additionally, the concentration of I2S after single and repeated IT doses in both CSF and peripheral blood, as well as the effects of I2S on CF biomarkers and urinary GAG will be assessed. Further evaluation will include effects of I2S on clinical parameters such as physiological and neurocognitive assessments, neuro-function and brain structure volumes. Additionally, the effects of treatment on daily living and relationships between biomarkers and symptoms can be evaluated.

Treatment of Hunter's Disease patients by IT delivery of I2S results in reduction of accumulation of sulfatide in various tissues (e.g., the nervous system, heart, liver, kidneys, gallbladder, and other organs).

While certain compounds, compositions and methods described herein have been described with specificity in accordance with certain embodiments, the following examples serve only to illustrate the compounds of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

We claim:

1. A method of treating Hunter Syndrome comprising a step of
administering intrathecally to a human subject in need of treatment a formulation comprising an iduronate-2-sulfatase (I2S) protein at a concentration at or greater than 5 mg/ml at a dose amount of at least 10 mg.

2. The method of claim 1, wherein the formulation comprises NaCl at a concentration of approximately 154 mM, polysorbate 20 at a concentration of approximately 0.005%, and a pH of approximately 6.

3. The method of claim 1, wherein the step of administering intrathecally results in no substantial adverse effects in the subject.

4. The method of claim 1, wherein the intrathecal administration of the formulation results in delivery of the I2S protein to target brain tissues.

5. The method of claim 4, wherein the target brain tissues comprise white matter and/or gray matter.

6. The method of claim 4, wherein the I2S protein is delivered to neurons, glial cells, perivascular cells and/or meningeal cells.

7. The method of claim 4, wherein the I2S protein is further delivered to the neurons in the spinal cord.

8. The method of claim 1, wherein the intrathecal administration of the formulation results in lysosomal localization in target brain tissues, spinal cord neurons and/or peripheral target tissues.

9. The method of claim 1, wherein the intrathecal administration of the formulation results in reduction of GAG storage in the target brain tissues, spinal cord neurons and/or peripheral target tissues.

10. The method of claim 1, wherein the intrathecal administration of the formulation results in reduced vacuolization in neurons.

11. The method of claim 1, wherein the intrathecal administration of the formulation results in increased I2S enzymatic activity in the target brain tissues, spinal cord neurons and/or peripheral target tissues.

12. The method of claim 1, wherein the intrathecal administration of the formulation results in reduced intensity, severity, or frequency, or delayed onset of at least one symptom or feature of the Hunter Syndrome.

13. The method of claim 12, wherein the at least one symptom or feature of the Hunter Syndrome is cognitive impairment; white matter lesions; dilated perivascular spaces in the brain parenchyma, ganglia, corpus callosum, and/or brainstem; atrophy; and/or ventriculomegaly.

14. The method of claim 1, wherein the intrathecal administration takes place at an interval selected from once every two weeks, once every month, once every two months.

15. The method of claim 1, wherein the intrathecal administration is used in conjunction with intravenous administration.

16. The method of claim 1, wherein the intrathecal administration is used in absence of concurrent immunosuppressive therapy.

17. The method of claim 1, wherein the I2S protein is a synthetic, recombinant, gene-activated or natural enzyme.

18. The method of claim 1, wherein the I2S protein is present at a concentration of at least about 10 mg/ml.

19. The method of claim 1, wherein the I2S protein is present at a concentration of approximately 50 mg/ml.

20. The method of claim 1, wherein the formulation contains a phosphate concentration no greater than 10 mM.

21. The method of claim 9, wherein the GAG storage is reduced by at least 20% as compared to an untreated control.

22. The method of claim 11, wherein the I2S enzymatic activity is increased by at least 1-fold as compared to an untreated control.

23. The method of claim 11, wherein the increased I2S enzymatic activity is at least approximately 10 nmol/hr/mg.

24. The method of claim 11, wherein the I2S enzymatic activity is increased in the lumbar region.

25. The method of claim 4, wherein the target brain tissue is a deep brain tissue at least 4 mm below the surface of the cerebrum.

26. The method of claim 10, wherein the neurons comprise Purkinje cells.

27. The method of claim 1, wherein the formulation is administered in a volume of about 1-5 ml.

28. A method of treating Hunter Syndrome, comprising a step of
    administering intrathecally to a human subject in need of treatment a formulation comprising an iduronate-2-sulfatase (I2S) protein at a concentration at or greater than 5 mg/ml, salt at a concentration of approximately 0-300 mM, a polysorbate surfactant at a concentration of approximately 0-0.02%, and a pH of approximately 5.5-6.5; wherein
    the formulation is administered at a volume of about 1-5 ml.

29. The method of claim 1, wherein the intrathecal administration is sustained release.

30. A method of treating Hunter Syndrome comprising a step of
    administering intrathecally to a human subject in need of treatment a formulation comprising an iduronate-2-sulfatase (I2S) protein at a concentration at or greater than 5 mg/ml in a saline solution at a volume at or greater than 1 ml but less than 15 ml.

* * * * *

UNITED STATES PATENT AND TRADEMARK OFFICE
CERTIFICATE OF CORRECTION

PATENT NO. : 8,545,837 B2  
APPLICATION NO. : 13/168966  
DATED : October 1, 2013  
INVENTOR(S) : Zhu et al.

Page 1 of 1

It is certified that error appears in the above-identified patent and that said Letters Patent is hereby corrected as shown below:

On the Title page of the patent, in the left-hand column at item (75), under the heading "Inventors":

Delete inventor's name "Fahmer" and replace it with --Fahrner--.

Signed and Sealed this  
Third Day of December, 2013

Margaret A. Focarino  
*Commissioner for Patents of the United States Patent and Trademark Office*